(12) United States Patent
Laine et al.

(10) Patent No.: US 11,407,743 B2
(45) Date of Patent: Aug. 9, 2022

(54) AMPHIPHILIC AND MESOGENIC ORGANIC DYES FOR TAILOR-MADE REFLECTIVE LOW-DIMENSIONAL MATERIALS

(71) Applicants: Sorbonne Universite, Paris (FR); Centre National De La Recherche Scientifique, Paris (FR); Universite de Paris, Paris (FR)

(72) Inventors: Philippe Laine, Paris (FR); Laurélie Poulard, Aulnay-sous-Bois (FR); Grégory Dupeyre, La Queue en Brie (FR); Valerie Marvaud, Paris (FR)

(73) Assignees: Sorbonne Universite, Paris (FR); Centre National De La Recherche Scientifique, Paris (FR); Universite de Paris, Paris (FR)

( * ) Notice: Subject to any disclaimer, the term of this patent is extended or adjusted under 35 U.S.C. 154(b) by 0 days.

(21) Appl. No.: 17/257,031

(22) PCT Filed: Jul. 5, 2019

(86) PCT No.: PCT/EP2019/068151
§ 371 (c)(1),
(2) Date: Dec. 30, 2020

(87) PCT Pub. No.: WO2020/008052
PCT Pub. Date: Jan. 9, 2020

(65) Prior Publication Data
US 2021/0122742 A1  Apr. 29, 2021

(30) Foreign Application Priority Data

Jul. 5, 2018 (EP) .................................... 18305891

(51) Int. Cl.
| | | |
|---|---|---|
| *C07C 211/50* | (2006.01) | |
| *C07C 217/84* | (2006.01) | |
| *C07D 321/00* | (2006.01) | |
| *C07F 7/08* | (2006.01) | |
| *C07D 409/12* | (2006.01) | |
| *C09D 7/41* | (2018.01) | |
| *C07C 217/94* | (2006.01) | |
| *C09B 11/12* | (2006.01) | |
| *C09B 11/26* | (2006.01) | |
| *C09D 5/33* | (2006.01) | |

(52) U.S. Cl.
CPC .......... *C07D 409/12* (2013.01); *C07C 211/50* (2013.01); *C07C 217/84* (2013.01); *C07C 217/94* (2013.01); *C07D 321/00* (2013.01); *C07F 7/0816* (2013.01); *C09B 11/12* (2013.01); *C09B 11/26* (2013.01); *C09D 5/004* (2013.01); *C09D 7/41* (2018.01); *C07C 2603/18* (2017.05); *C07C 2603/24* (2017.05); *C07C 2603/32* (2017.05)

(58) Field of Classification Search
CPC ... C07C 211/50; C07C 217/84; C07D 321/00; C07D 333/20; C07F 7/0816
See application file for complete search history.

(56) References Cited

U.S. PATENT DOCUMENTS 4,812,141 A * 3/1989 Baumgartner .......... D06P 5/138
524/84

OTHER PUBLICATIONS

Aug. 13, 2019—(WO) International Search Report—Appl No. PCT/EP2019/068151.
Sorensen et al. "Synthesis and optical properties of trioxatriangulenium dyes with one and two periperal amino substituents" Journal of Organic Chemistry, vol. 75, No. 18, Aug. 26, 2010, pp. 6182-6190.
Kondo et al. "Gold-coloured organic crystals of an azobenzene derivative" Langmuir, vol. 30, No. 15, Apr. 1, 2014, pp. 4422-4426.
Evans et al. "(E)-5,5'-Di(thiophen-2-yl)-3,3'-bi[thiophen-3(2H)-ylidene]-2,2'-diones—from conspicuous blue impurities to "quasi-metallic" golden-bronze crystals" Organic & Biomolecular Chemistry, vol. 11, No. 23, May 8, 2013, pp. 3871-3879.

* cited by examiner

*Primary Examiner* — Noble E Jarrell
(74) *Attorney, Agent, or Firm* — Banner & Witcoff, Ltd.

(57) ABSTRACT

The present invention relates to a compound of the following formula (I):

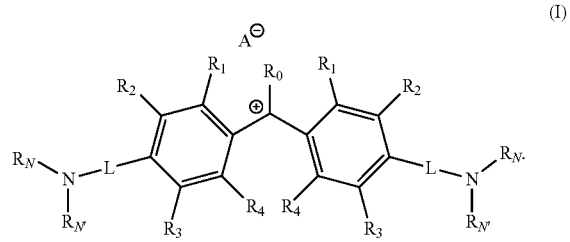

The invention also relates to uses thereof as dye or pigment, notably as a luster pigment. The invention relates also to a reflective or photonic or nanophotonic or optoelectronic device comprising a compound of the invention. The invention relates also to a metal-like reflective coating, a metal-like particle or an organic-based metal-like liquid film comprising a compound of the invention.

22 Claims, 13 Drawing Sheets

AMPHIPHILIC AND MESOGENIC ORGANIC DYES FOR TAILOR-MADE REFLECTIVE LOW-DIMENSIONAL MATERIALS

RELATED APPLICATION DATA

This application is a National Stage Application under 35 U.S.C. 371 of co-pending PCT application number PCT/EP2019/068151 designating the United States and filed Jul. 5, 2019; which claims the benefit of EP application number 18305891.6 and filed Jul. 5, 2018 each of which are hereby incorporated by reference in their entireties.

FIELD OF THE INVENTION

The present invention relates to sterically congested, V-shaped diarylcarbenium derivatives (that encompasses triarylcarbenium species comprised of only two main "electroactive arms" so that their overall key V-shaped topology is preserved), as well as their use as molecular chromophores of interest as such (e.g. dye molecules) and as components of pigments displaying special optical effects or of organic metal-like liquid films.

Indeed, said diarylcarbenium derivatives of tunable electronic features can serve as the building blocks of organized organic molecular materials exhibiting special optical properties including (1) metal-like reflection or (2) iridescence or pearl-luster effects, that are referred to as special optical effects that respectively originate from interaction of light with the material surface, in the former case (1), or with the bulk material, in the latter case (2).

BACKGROUND OF THE INVENTION

Carbocations represent key intermediates in organic chemistry that were thoroughly studied by G. A. Olah (Nobel prize laureate 1994), who continuously sought to form persistent types of these species, notably by manipulating them at low temperature in superacidic systems. [Olah, G. A. Angew. Chem., Int. Ed. Engl. 1995, 34, 1393-1405]

In this peculiar field of organic chemistry, there exists, however, some stable compounds of the triarylcarbenium type, some of them being of the utmost importance (e.g. for dye implementations), like triarylmethane dyes (methyl violet, malachite green and fuchsine dyes, phenol dyes, Victoria blue dyes) and xanthene dyes that are their bridged counterparts (among which rhodamine and fluorescein, for instance). On the other hand, diarylcarbeniums are usually just stable enough to be spectroscopically studied without being isolated in their pure form. Indeed, these are often generated in situ (in solution) via suitable precursors, and immediately reacted with proper nucleophilic species.

For example, diphenylcarbenium ions have been previously reported in the literature. Notably, Mayr et al. [Mayr et al. J. Am. Chem. Soc. 2001, 123(39), 9500-9512] have synthetized analogues of the well-known Michler's Hydrol Blue.

Mayr's diphenylcarbeniums have proved to be very useful reference compounds since they allowed establishing extensive electrophilicity and nucleophilicity scales, in spite of their disputable stability, especially in solution, that precludes any further utilization as such. Indeed, very scarce examples of stable diarylcarbenium have been published hitherto.

Diarylcarbeniums possessing a 3-guaiazulenyl (or azulen-1-yl) group have been synthesized by Takekuma et al. [Takekuma et al. Tetrahedron 2007, 63, 12058-12070], whereas Barbero et al. have recently reported the synthesis of bench-stable diarylcarbenium tetrafluoroborates bearing indolyl or pyrrolyl moieties (see [Barbero et al. J. Org. Chem. 2012, 77, 4278-4287] and [Barbero et al. J. Org. Chem. 2015, 80, 4791-4796]).

Interestingly, Sorensen et al. have described triazatriangulenium tetrafluoroborate salts, which constitute a specific class of triphenylcarbenium ions, which phenyl rings are bound together by means of nitrogen atoms [Sorensen et al. J. Mater. Chem. 2012, 22, 4797-4805]. The said triazatriangulenium molecules are electroactive dyes, and self-assemble to form highly ordered supramolecular structures. It has been shown that as an anisotropic polycrystalline thin film structure, they ensure an efficient exciton transport.

Specular reflection of light is generally related to electronic conduction (surface plasmon). However, the development of metal-free, non-conductive, reflective organic molecular materials, relying on excitonic processes would pave the way for a wide variety of applications in a broad spectrum of areas: from reflectors or mirrors to photonics, paints and coatings (including niche implementations for which co-existence of electronic conduction and light reflection is detrimental), security inks, cosmetics, optoelectronics and laser technology, amongst others.

Special effect pigments are nano- or meso-particulate materials that give additional color effects, such as angular color dependence (iridescence, luster) or texture. Also named "luster pigments", these pigments are subdivided in 2 classes: metal effect pigments and pearl luster pigments (see [Special Effect Pigments, G. Pfaff, 2008, $2^{nd}$ Rev. ed., Vincentz Network GmbH & Co. KG, Hannover/Germany] and [Metal Effect Pigments, Fundamentals and Applications, P. Wißling, 2006, Vincentz Network GmbH & Co. KG, Hannover/Germany]).

With the exception of examples of "effect pigments" based on organic structures, amongst which so-called "photonic crystals" mostly encountered in Nature (e.g. guanine platelets isolated from fish scales and certain liquid crystals), the industry of "effect pigments" relies almost exclusively on metallic particles and purposely-structured inorganic materials (e.g. crystalline $HgCl_2$ platelets, lead, arsenic or bismuth salts, platelet-shaped $PbHPO_4$, mica-$TiO_2$ combination, basic lead carbonate, bismuth oxychloride, aluminium platelets coated with $Fe_2O_3$, metal oxide-coated synthetic mica, iron oxides mica, chromium(III) oxide mica, $Al_2O_3$ flakes, $SiO_2$ flakes, borosilicate flakes).

Most of these pigments suffer from environmental and/or durability issues: for instance, mercury, lead, arsenic and chromium are considered to be highly toxic.

Hence, there is a need for organic iridescent/pearlescent pigments, environmentally benign and durable.

Hitherto, by definition, "metallic effect pigment" is a subfamily of the "metallic pigment" group that includes "metal pigments" (consisting of pure metals or metal alloys) and either inorganic or organic color pigments possessing at least one metal atom in their formula. Here we propose to use purely organic molecular materials as "metallic effect pigments".

Although conductive polymers are known to display a metallic luster (see [Tanaka et al. Bull. Chem. Soc. Jpn. 1980, 53, 3430-3435], [Morikita et al. Adv. Mater. 2001, 13, 1862-1864] and [Yamamoto et al. Macromolecules 2003, 36, 4262-4267]), very few low molecular weight materials exhibit such a behavior and none is of any significance for industry. Only scarce examples can be cited from the literature, such as 1-aryl-2-[5-(tricyanoethenyl)-2-thienyl]pyrroles, (E)-5,5'-di(thiophen-2-yl)-3,3'-bi[thiophen-3(2H)-ylidene]-2,2'-diones, bis[4-(2-dimethylaminoethoxy)phenyl]diazene and a donor-acceptor molecule bearing two boron(III) diketonate moieties (see [Ogura et al. Org. Biomol. Chem. 2003, 1, 3845-3850], [Ogura et al. Tetrahedron 2006, 62, 2484-2491], [Evans et al. Org. Biomol. Chem. 2013, 11, 3871-3879], [Kondo et al. Langmuir 2014, 30, 4422-4426] and [Poon et al. Angew. Chem. Int. Ed. 2016, 128, 3711-3715]). Those compounds are resulting from serendipity rather than from a specific molecular design, and most often, they are not fully characterized, including from the standpoint of the rationalization of their unusual optical properties.

Noteworthy, however, is the reported example of a polymeric material based on polyvinyl alcohol (PVA) and doped with J-aggregates of TDBC (5,6-dichloro-2-[[5,6-dichloro-1-ethyl-3-(4-sulphobutyl)-benzimidazol-2-ylidene]-propenyl]-1-ethyl-3-(4-sulphobutyl)benzimidazolium hydroxide, sodium salt), that displays metal-like optical properties (see [Gentile et al. Nano Lett. 2014, 14, 2339-2344] and [Gentile et al. J. Opt. 2016, 18, 015001]).

Therefore, there is a need for reflective organic materials alternative to inorganic and metal-based compounds. For this purpose, the present invention relies on the self-assembly of specifically-conceived chromophores that feature huge molar extinction coefficients and very sharp absorption bands.

In this context, there exists a strong interest in developing chromophoric building blocks featuring above-mentioned electronic features that are namely new stable diarylcarbenium derivatives of V-shaped topology. Indeed, on the one hand, the individual compounds are interesting by themselves, as highly efficient chromophores. On the other hand, these salts can self-assemble, allowing the formation of anisotropic organic supramolecular materials displaying "special optical effects", including liquid mirrors.

Since the mid-nineteenth century, research has been devoted to the design of liquid mirrors made of a rotating reflective liquid. Until recently, the liquid used prevalently consisted simply of mercury, which is the sole metal to display a sufficiently low melting point. Due to toxicity and high-density issues, gallium and its alloys tend to advantageously substitute mercury for a wide range of applications [U.S. Pat. No. 5,792,236] but are not exempt of drawbacks (melting point above room temperature, oxidation layer formed on surface, cost).

More recently, alternative strategies have been proposed. A first breakthrough was initiated by works published in two seminal papers that demonstrated the possibility to obtain highly reflective silver films—named MELLFs for Metal-Like Liquid Films—at the interface between two immiscible liquids by using simple chemical deposition techniques with a mixture composed of $AgNO_3$, a reducing agent and a surfactant (see [Yogev et al. J. Phys. Chem., 1988, 92, 5754-5760] and [Efrima, S. Crit. Rev. Surf. Chem. 1991, 1, 167-215]). Due to the particularly appealing optical properties of such films, efforts were devoted towards obtaining a reflective coating at an air-liquid interface, which constitutes the first surface to be encountered by the incoming light in an optical system. Some significant results were demonstrated by spreading silver nanoparticles coated with organic ligands on a liquid substrate where they self-assemble (see [Gordon et al. J. Phys. Chem., 1989, 93, 6814-6817], [Yockell-Lelievre et al. Appl. Opt., 2003, 42, 1882-1887] and [Gingras et al. Colloids Surf., 2006, 279, 79-86]). This constitutes a quite easiest way to deposit metal particles on liquids in comparison with previous methods involving high-vacuum conditions or using a helium stream carrying a gold vapor toward the liquid interface (see [Blackboron, J. R.; Young, D. Metal Vapor Synthesis in Organometallic Chemistry No. 9\ Springer-Verlag: Berlin, 1979] and [Halpern, B. L. J. Colloid Interface Sci., 1982, 86, 337]). The MEELF technology is now well established (see [U.S. Ser. No. 00/695,1398B2] and [Yen et al. ACS Appl. Mater. Interfaces, 2014, 6, 4292-4300]), so that it is considered, to date, as the best alternative to metal liquid films and not appealing simply for its optical properties but for numerous applications such as optoelectronics, sensing, catalysis, and surface-enhanced Raman spectroscopy [Lu et al. Chem. Mater., 2018, 30, 1989-1997].

The benefits of a liquid mirror, compared to a conventional solid one, are numerous: 1) access to a cheap very large reflective surface displaying a high numerical aperture (e. g. for astronomy, space debris observation, LIDAR systems) 2) easy access to a quasi-flawless reflective surface, easy to clean and able to self-healing, 3) access to a reflective surface easy to ship and assemble (e.g. in order to install a lunar telescope, see [Borra et al. Nature, 2007, 447, 979-981]), 4) remove of the perspective or parallax error produced by conventional lenses that requires a sensor with an optical aperture larger than the object itself (telecentric scanning lenses for increasing image quality and applications including metrology, gauging, CCD based measurement, or microlithography [Thibault et al. SPIE, 1997, 3100, 206-213]).

Moreover, the main drawback of the liquid mirror technology in astronomy: its compulsory horizontal position (due to the low viscosity of mercury) allowing solely zenithal observation tends to be circumvented thanks to new tiltable liquid mirrors made of a reflective layer deposited on a hydrophobic viscous liquid [Gagné et al. Astron. Astrophys., 2008, 479, 597-602].

Consequently, apart from applications yet attainable (even if more expensively) with solid mirrors, such a technology may address other needs. Liquid mirror may be shaped by rotation or by thermal or magnetic fields (see [Truong, L. et al. Appl. Opt., 2005, 44, 1595], [Déry et al. Chem. Mater., 2008, 20, 6420-6426] and [EP1361585]), or may enter in the composition of a reflective renewable fluid in a device submitted to highly damaging, extremely intense photon beams [US 20020135908].

Another of the most promising application is the electrical control of a metal nanoparticles-based reflecting surface at an interface between water and oil using the ITIES system (for Interface of Two Immiscible Electrolytic Solutions), that if controlled opens the way towards real-time electro-switchable smart mirrors for smart window applications, for example (see [Flatté et al. J. Phys. Chem. C, 2010, 114, 1735-1747] and [Montelongo et al. Nat. Mater., 2017, 16, 1127-1136]).

Due to the intrinsic anisotropy displayed by the molecules objects of the present invention, the decoration of their electron-donating termini with long hydrophobic chains makes them behaving as amphiphilic to mesogenic (liquid crystalline) dyes (depending on the nature and rigidity of extension groups), that render them particularly well suited for the design of a novel class of organic-based metal-like liquid films. Moreover, the chromophoric nature of the molecules, that originates in a particularly efficient inner charge transfer (characterized by both a high molar extinction coefficient and a sharp absorption band) induce the self-assembly of films or layered surfaces displaying highly reflective properties without resort to any metal, paving the way to inexpensive, environmentally benign and durable liquid mirrors (moreover possibly electroswitchable, given the reducible character of the carbenium here described).

SUMMARY OF THE INVENTION

The present invention relates thus to a compound of the following formula (I):

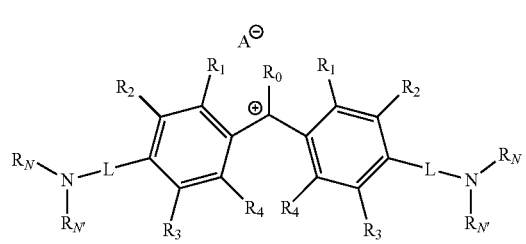
(I)

wherein:
$R_0$ represents a hydrogen atom, a halogen atom, a $(C_1$-$C_6)$alkyl, $(C_1$-$C_6)$haloalkyl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $OR_5$, $SR_6$, $NR_7R_8$, $PR_9R_{10}$, $COR_{11}$, $CO_2R_{12}$, $CONR_{13}R_{14}$, $SO_2R_{15}$, $SO_3H$, $CN$, $NO_2$, $OCOR_{16}$, $OCO_2R_{17}$, $NR_{18}COR_{19}$ or $NR_{20}SO_2R_{21}$ group, or is selected from the group consisting of:

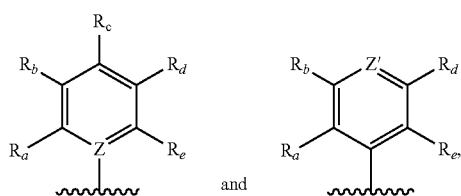
and wherein:
Z represents C or $N^+A_z^-$ and Z' represents N or $N^+$—$R_c'$ $A_z^-$, wherein
$A_z^-$ represents a monovalent organic or inorganic anion, and
$R_c'$ represents a hydrogen atom or a $(C_1$-$C_6)$alkyl group,
$R_a$ and $R_e$ each represent, independently of each other, a hydrogen atom, a halogen atom, a $(C_1$-$C_{20})$alkyl, $(C_1$-$C_{20})$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $OR_{22}$ or $SR_{23}$ group, and
$R_b$, $R_c$ and $R_d$ each represent, independently of each other, a hydrogen atom, a halogen atom or a $(C_1$-$C_{20})$alkyl, $(C_1$-$C_{20})$haloalkyl, cycloalkyl, cycloalkyl-$(C_1$-$C_6)$alkyl, heterocycle or heterocycle-$(C_1$-$C_6)$alkyl, $O(C_1$-$C_{20})$alkyl group;
$R_1$ represents a halogen atom, a $(C_1$-$C_{20})$alkyl, $(C_2$-$C_{12})$alkenyl, $(C_2$-$C_{12})$alkynyl, $(C_1$-$C_{20})$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;

$R_4$ represents a halogen atom, a $(C_1$-$C_{20})$alkyl, $(C_2$-$C_{12})$alkenyl, $(C_2$-$C_{12})$alkynyl, $(C_1$-$C_{20})$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $(CH_2)_mOR_{24}$, $(CH_2)_mSR_{25}$, $OR_{26}$, $SR_{27}$, $NR_{28}R_{29}$, $PR_{30}R_{31}$, $COR_{32}$, $CO_2R_{33}$, $CONR_{34}R_{35}$, $OCOR_{36}$, $OCO_2R_{37}$, $NR_{38}COR_{39}$, or $NR_{40}SO_2R_{41}$ group, wherein m and m' are, independently of each other, equal to 1, 2 or 3, preferably 1;
or
both $R_4$ groups form together a bond or a chain selected from the group consisting of —$C(R_{42}R_{43})$—, —$(CH_2)_n$—, —$Si(R_{44}R_{45})$—, —$(CH_2)_p$—Y —$(CH_2)_q$—, and —Y—$(CR_{46}R_{47})_r$—Y'—, wherein:
Y and Y' each represent, independently of each other, O, S or $NR_{48}$,
n is equal to 2 or 3,
p is equal to 1 or 2,
q is equal to 0 or 1,
r is equal to 1 or 2,
$R_{42}$ and $R_{43}$, each represent, independently of each other, a $(C_1$-$C_6)$alkyl or an aryl group,
$R_{44}$ and $R_{45}$ each represent, independently of each other, a $(C_1$-$C_6)$alkyl or an aryl group, and
$R_{46}$, $R_{47}$ and $R_{48}$ each represent, independently of each other, a hydrogen atom, a $(C_1$-$C_6)$alkyl or an aryl group;
L represents a bond, or a group selected from the group consisting of:

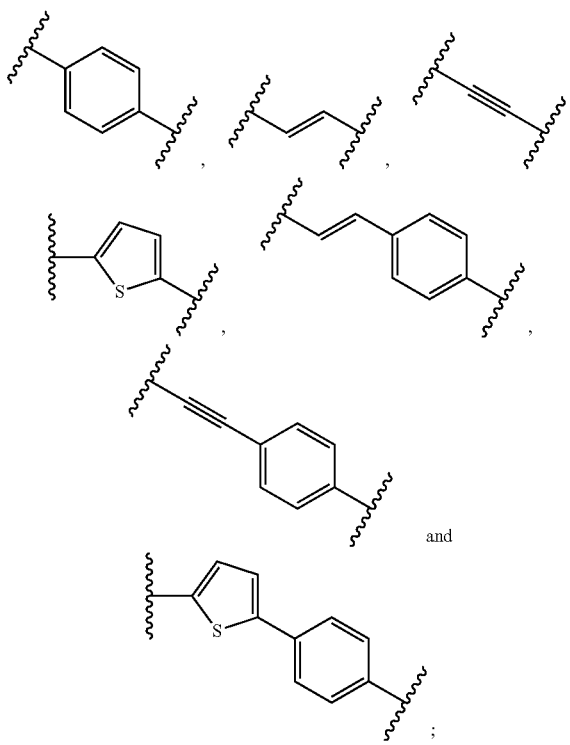
and

;

$R_2$ and $R_3$ each represent, independently of each other, a hydrogen atom, a halogen atom, a $(C_1$-$C_6)$alkyl, $(C_2$-$C_6)$alkenyl, $(C_2$-$C_6)$alkynyl, $(C_1$-$C_6)$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $OR_{49}$, $SR_{50}$, $NR_{51}R_{52}$, $COR_{53}$, $CO_2R_{54}$ or $CONR_{55}R_{56}$ group;

or

L represents:

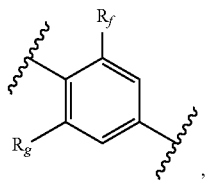

and $R_f$ and $R_2$, and $R_g$ and $R_3$ form together with the carbon atoms that carry them a cycloalkenyl or aryl group;

$R_N$ and $R_N'$ each represent, independently of each other, a $(C_7-C_{20})$alkyl or $(C_7-C_{20})$haloalkyl group, said group being optionally substituted by one or more groups selected from a $OR_{62}$, $SR_{63}$ and $NR_{64}R_{65}$, or a group selected from the group consisting of:

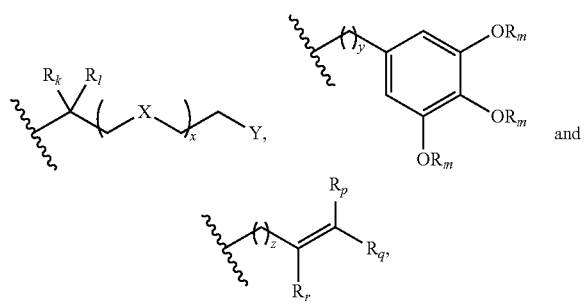

wherein:
X represents O, S or $NR_{57}$,
Y represents $OR_{58}$, $SR_{59}$ or $NR_{60}R_{61}$,
x is equal to 0, 1, 2 or 3,
y is equal to 0, 1, 2 or 3,
z is equal to 0, 1, 2 or 3,
$R_k$ and $R_l$ each represent, independently of each other, a hydrogen atom or a $(C_1-C_6)$alkyl group,
$R_m$ represents a $(C_1-C_{20})$alkyl group,
$R_r$ represents a hydrogen atom or a $(C_1-C_6)$alkyl group,
$R_p$ and $R_q$ each represent, independently of each other, a hydrogen atom, a $(C_1-C_6)$alkyl, an aryl or heteroaryl group,
$R_{57}$ to $R_{65}$ each represent, independently of each other, a hydrogen atom or a $(C_1-C_6)$alkyl group;

$R_5$ to $R_{21}$, $R_{24}$, $R_2$, $R_{28}$ to $R_{41}$ and $R_{49}$ to $R_{56}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, preferably a hydrogen atom or a $(C_1-C_6)$alkyl group, said group being optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group, wherein $R_{66}$ to $R_{69}$ each represent, independently of each other, a hydrogen atom or a $(C_1-C_6)$alkyl group;

$R_{22}$, $R_{23}$, $R_{26}$ and $R_{27}$ each represent, independently of each other a hydrogen atom, a $(C_1-C_{20})$alkyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, preferably a hydrogen atom or a $(C_1-C_{20})$alkyl, notably $(C_1-C_{12})$alkyl, in particular $(C_1-C_6)$alkyl group, said group being optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group, wherein $R_{66}$ to $R_{69}$ each represent, independently of each other, a hydrogen atom or a $(C_1-C_6)$alkyl group;

and $A^-$ represents a monovalent, organic or inorganic anion.

In particular, the present invention relates to a compound of the above formula (I), wherein:

$R_0$ represents a hydrogen atom, a halogen atom, a $(C_1-C_6)$alkyl, $(C_1-C_6)$haloalkyl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R_8$, $COR_{11}$, $CO_2R_{12}$, $CONR_{13}R_{14}$, $SO_2R_{15}$, CN or $NO_2$, group, or is selected from the group consisting of:

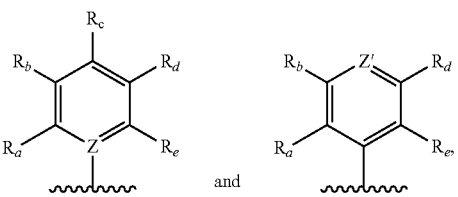

and wherein:
Z represents C or $N^+$ $A_z^-$ and Z' represents N or $N^+$—$R_c'$ $A_z^-$, wherein
$A_z^-$ represents a monovalent organic or inorganic anion, and
$R_c'$ represents a hydrogen atom or a $(C_1-C_6)$alkyl group,
$R_a$ and $R_e$ each represent, independently of each other, a hydrogen atom, a halogen atom, a $(C_1-C_{20})$alkyl, $(C_1-C_{20})$haloalkyl, aryl, heteroaryl, aryl-$(C_1-C_6)$alkyl, cycloalkyl, heterocycle, heterocycle-$(C_1-C_6)$alkyl, $OR_{22}$ or $SR_{23}$ group, and
$R_b$, $R_c$ and $R_d$ each represent, independently of each other, a hydrogen atom, a halogen atom or a $(C_1-C_{20})$alkyl, $(C_1-C_{20})$haloalkyl, cycloalkyl, heterocycle or $O(C_1-C_{20})$alkyl group;

$R_1$ represents a halogen atom, a $(C_1-C_{20})$alkyl, $(C_2-C_{12})$alkynyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3, preferably 1;

$R_4$ represents a halogen atom, a $(C_1-C_{20})$alkyl, $(C_2-C_{12})$alkynyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_mOR_{24}$, $(CH_2)_mSR_{25}$, $OR_{26}$, $SR_{27}$, $NR_{28}R_{29}$, $COR_{32}$, $OCOR_{36}$ or $NR_{38}COR_{39}$, group, wherein m and m' are, independently of each other, equal to 1, 2 or 3, preferably 1;

or both $R_4$ groups form together a bond or a chain selected from the group consisting of —$C(R_{42}R_{43})$—, —$(CH_2)_n$—, —$Si(R_{44}R_{45})$—, —$CH_2$—Y—$CH_2$—, and —Y—$CH_2$—$CH_2$—Y'—, wherein:

Y and Y' each represent, independently of each other, O, S or NH, n is equal to 2 or 3, R$_{42}$ and R$_{43}$, each represent, independently of each other, a (C$_1$-C$_6$)alkyl or an aryl group, and R$_{44}$ and R$_{45}$ each represent, independently of each other, a (C$_1$-C$_6$)alkyl or an aryl group;

L represents a bond, or a group selected from the group consisting of:

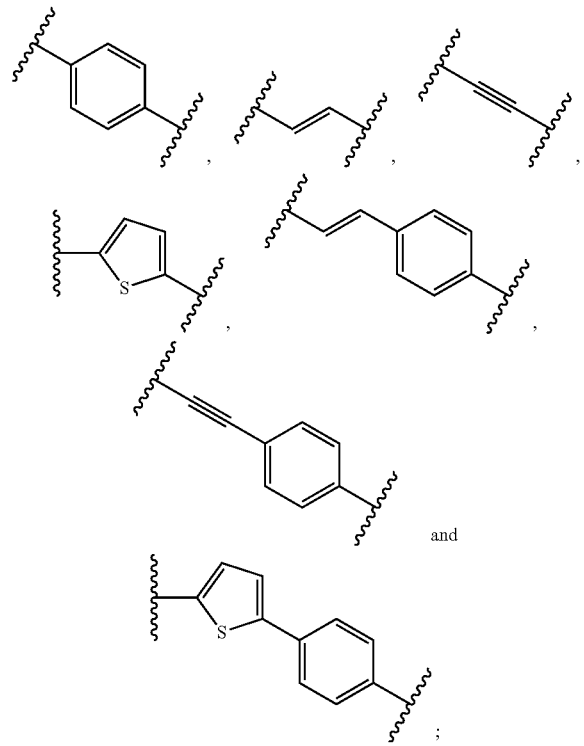

R$_2$ and R$_3$ each represent, independently of each other, a hydrogen atom, a halogen atom, a (C$_1$-C$_6$)alkyl, (C$_1$-C$_6$)haloalkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle, heterocycle-(C$_1$-C$_6$)alkyl, OR$_{49}$ or NR$_{51}$R$_{52}$, group;

or

L represents:

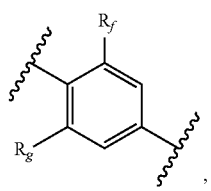

and

R$_f$ and R$_2$, and R$_g$ and R$_3$ form together with the carbon atoms that carry them a cycloalkenyl or aryl group;

R$_N$ and R$_N'$ each represent, independently of each other, a (C$_7$-C$_{20}$)alkyl or (C$_7$-C$_{20}$)haloalkyl group, said group being optionally substituted by one or more groups selected from OR$_{62}$, SR$_{63}$ and NR$_{64}$R$_{65}$ or a group selected from the group consisting of:

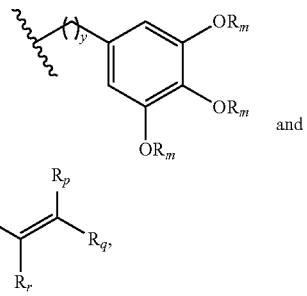

wherein:

X represents O, S or NR$_{57}$,

Y represents OR$_{58}$, SR$_{59}$ or NR$_{60}$R$_{61}$, x is equal to 0, 1, 2 or 3, preferably x is equal to 1, 2 or 3, y is equal to 0, 1, 2 or 3, z is equal to 0, 1, 2 or 3, R$_k$ and R$_l$ each represent, independently of each other, a hydrogen atom or a (C$_1$-C$_6$)alkyl group, R$_m$ represents a (C$_1$-C$_{20}$)alkyl group, R$_r$ represents a hydrogen atom or a (C$_1$-C$_6$)alkyl group, R$_p$ and R$_q$ each represent, independently of each other, a hydrogen atom, a (C$_1$-C$_6$)alkyl, an aryl or heteroaryl group, R$_{57}$ to R$_{65}$ each represent, independently of each other, a hydrogen atom or a (C$_1$-C$_6$)alkyl group;

R$_5$ to R$_8$, R$_{11}$ to R$_{15}$, R$_{24}$, R$_{25}$, R$_{28}$, R$_{29}$, R$_{32}$, R$_{36}$, R$_{38}$, R$_{39}$, R$_{49}$; R$_{51}$ and R$_{52}$ each represent, independently of each other, a hydrogen atom, a (C$_1$-C$_6$)alkyl, (C$_1$-C$_6$)haloalkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle or heterocycle-(C$_1$-C$_6$)alkyl group, preferably a hydrogen atom or a (C$_1$-C$_2$)alkyl, notably (C$_1$-C$_{12}$)alkyl, in particular (C$_1$-C$_6$)alkyl group, said group being optionally substituted by one or more groups selected from a halogen atom, a (C$_1$-C$_6$)alkyl, (C$_1$-C$_6$)haloalkyl, OR$_{64}$, SR$_{65}$ and NR$_{66}$R$_{67}$ group, wherein R$_{64}$ to R$_{67}$ each represent, independently of each other, a hydrogen atom or a (C$_1$-C$_6$)alkyl group;

R$_{22}$, R$_{23}$, R$_{26}$ and R$_{27}$ each represent, independently of each other a hydrogen atom, a (C$_1$-C$_{20}$)alkyl, (C$_1$-C$_{20}$)haloalkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle or heterocycle-(C$_1$-C$_6$)alkyl group, preferably a hydrogen atom or a (C$_1$-C$_6$)alkyl group, said group being optionally substituted by one or more groups selected from a halogen atom, a (C$_1$-C$_6$)alkyl, (C$_1$-C$_6$)haloalkyl, OR$_{66}$, SR$_{67}$ and NR$_{68}$R$_{69}$ group, wherein R$_{66}$ to R$_{69}$ each represent, independently of each other, a hydrogen atom or a (C$_1$-C$_6$)alkyl group;

and

A$^-$ represents a monovalent, organic or inorganic anion.

Advantageously, when R$_1$ and R$_4$ are the same, and R$_0$ is:

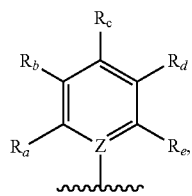

wherein Z represents C, at least one of $R_a$ and $R_e$ is not the same as $R_f$.

Definitions

The term "halogen" as used in the present invention refers to an atom of fluorine, bromine, chlorine or iodine. Advantageously, this is an atom of fluorine or bromine.

The term "$(C_1-C_{20})$alkyl" as used in the present invention refers to a saturated, linear or branched hydrocarbon chain comprising from 1 to 6 carbon atoms, including, but not limited to, methyl, ethyl, n-propyl, isopropyl, n-butyl, isobutyl, sec-butyl, tert-butyl, n-pentyl, n-hexyl and the like.

The term "$(C_1-C_{20})$alkyl" as used in the present invention refers to a saturated, linear or branched hydrocarbon chain comprising from 1 to 20 carbon atoms, including, but not limited to, the $(C_1-C_6)$alkyl groups enumerated above, and octyl, decyl, dodecyl, tetradecyl, hexadecyl, octadecyl, eicosyl and the like.

The term "$(C_1-C_6)$haloalkyl" as used in the present invention refers to any $(C_1-C_6)$alkyl group as defined above in which one or more hydrogen atoms have been each replaced with a halogen atom. It can be notably a trifluoromethyl group.

The term "$(C_1-C_{20})$haloalkyl" as used in the present invention refers to any $(C_1-C_{20})$alkyl group as defined above in which one or more hydrogen atoms have been each replaced with a halogen atom. It can be notably perfluorooctyl, 1H,1H,2H,2H-perfluorooctyl, perfluorodecyl, 1H,1H,2H,2H-perfluorodecyl, perfluoroeicosyl and the like.

The term "$(C_2-C_6)$alkenyl" as used in the present invention refers to a linear or branched hydrocarbon chain comprising at least one double bond and comprising from 2 to 6 carbon atoms including, but not limited to, ethenyl (e.g. vinyl), propenyl (e.g. allyl) and the like.

The term "$(C_2-C_6)$alkynyl" as used in the present invention refers to a linear or branched hydrocarbon chain comprising at least one triple bond and comprising from 2 to 6 carbon atoms including, but not limited to, ethynyl, propynyl and the like.

The term "cycloalkyl" as used in the present invention refers to a saturated hydrocarbon ring comprising from 3 to 7, advantageously from 5 to 7, carbon atoms including, but not limited to, cyclohexyl, cyclopentyl, cyclopropyl, cycloheptyl and the like.

The term "cycloalkenyl" as used in the present invention refers to an unsaturated hydrocarbon ring comprising from 3 to 7, advantageously from 5 to 6, carbon atoms, including, but not limited to, cyclopentenyl, cyclohexenyl, cyclopentadienyl, cyclohexadienyl and the like.

The term "heterocycle" as used in the present invention refers to a saturated or unsaturated non-aromatic monocycle or polycycle, comprising fused, bridged or spiro rings, preferably fused rings, advantageously comprising 3 to 10, notably 3 to 6, atoms in each ring, in which the atoms of the ring(s) comprise one or more, advantageously 1 to 3, heteroatoms selected from O, S and N, preferably O and N, the remainder being carbon atoms.

A saturated heterocycle is more particularly a 3-, 4-, 5- or 6-membered, even more particularly a 5- or 6-membered saturated monocyclic heterocycle such as an aziridine, an azetidine, a pyrrolidine, a tetrahydrofuran, a 1,3-dioxolane, a tetrahydrothiophene, a thiazolidine, an isothiazolidine, an oxazolidine, an isoxazolidine, an imidazolidine, a pyrazolidine, a triazolidine, a piperidine, a piperazine, a 1,4-dioxane, a morpholine or a thiomorpholine.

An unsaturated heterocycle is more particularly an unsaturated monocyclic or bicyclic heterocycle, each cycle comprising 5 or 6 members, such as 1H-azirine, a pyrroline, a dihydrofuran, a 1,3-dioxolene, a dihydrothiophene, a thiazoline, an isothiazoline, an oxazoline, an isoxazoline, an imidazoline, a pyrazoline, a triazoline, a dihydropyridine, a tetrahydropyridine, a dihydropyrimidine, a tetrahydropyrimidine, a dihydropyridazine, a tetrahydropyridazine, a dihydropyrazine, a tetrahydropyrazine, a dihydrotriazine, a tetrahydrotriazine, a 1,4-dioxene, an indoline, a 2,3-dihydrobenzofuran (coumaran), a 2,3-dihydrobenzothiophene, a 1,3-benzodioxole, a 1,3-benzoxathiole, a benzoxazoline, a benzothiazoline, a benzimidazoline, a chromane or a chromene.

The term "aryl", as used in the present invention, refers to an aromatic hydrocarbon group comprising preferably 6 to 14 carbon atoms and comprising one or more fused rings, such as, for example, a phenyl, naphthyl or anthracenyl group. Advantageously, it will be a phenyl group.

The term "heteroaryl" as used in the present invention refers to an aromatic heterocycle as defined above. It can be more particularly an aromatic monocyclic, bicyclic or tricyclic heterocycle, each cycle comprising 5 or 6 members, such as a pyrrole, a furan, a thiophene, a thiazole, an isothiazole, an oxazole, an isoxazole, an imidazole, a pyrazole, a triazole, a pyridine, a pyrimidine, an indole, a benzofuran, a benzothiophene, a benzothiazole, a benzoxazole, a benzimidazole, an indazole, a benzotriazole, a quinoline, an isoquinoline, a cinnoline, a quinazoline, a quinoxaline, a carbazole, or a julolidine.

The term "cycloalkyl-$(C_1-C_6)$alkyl" as used in the present invention refers to any cycloalkyl group as defined above, which is bound to the molecule by means of a $(C_1-C_6)$-alkyl group as defined above.

The term "heterocycle-$(C_1-C_6)$alkyl" as used in the present invention refers to a heterocycle group as defined above, which is bound to the molecule by means of a $(C_1-C_6)$-alkyl group as defined above.

The term "aryl-$(C_1-C_6)$-alkyl" as used in the present invention refers to any aryl group as defined above, which is bound to the molecule by means of a $(C_1-C_6)$-alkyl group as defined above. In particular, it can be a benzyl group.

The term "heteroaryl-$(C_1-C_6)$alkyl" as used in the present invention refers to a heteroaryl group as defined above, which is bound to the molecule by means of a $(C_1-C_6)$-alkyl group as defined above.

The expression "organic or inorganic anion" refers, within the sense of the present invention, to a negatively-charged counter-ion. It can be in particular a halide (fluoride, chloride, bromide, iodide), perchlorate, nitrate, sulfate, alkylsulfate, benzenesulfonate, p-toluene sulfonate, chlorosulfonate, fluorosulfonate, trifluorosulfonate, methanesulfonate, benzenesulfinate, tetrafluoroborate, tetraphenylborate, tetrakis(pentafluorophenyl)borate, tris(tetrachlorobenzenediolato)phosphate(V) (TRISPHAT), (1,1'-binaphthalene-2,2'diolato)(bis(tetrachloro-1,2-benzenediolato)phosphate(V) (BINPHAT), acetate, trifluoroacetate, propionate, benzoate, oxalate, succinate, oleate, stearate, citrate, 4-hydroxyphenolate, 2,3,5,6-tetrachloro-4-hydroxyphenolate, 2,3-dichloro-5,6-dicyano-4-hydroxyphenolate (DDQH$^-$), hydrogenophosphate, dihydrogenophosphate or hexafluorophosphate anion. Preferably, it is a hexafluorophosphate, 2,3-dichloro-5,6-dicyano-4-hydroxyphenolate (DDQH$^-$), tetrafluoroborate, halide or triflate anion, more preferably a 2,3-dichloro-5,6-dicyano-4-hydroxyphenolate (DDQH$^-$) or hexafluorophosphate anion, notably a hexafluorophosphate anion.

In the context of the present invention, "C+" refers to the trivalent carbon atom that is linked to $R_0$.

In the context of the present invention, the terms "precursor" or "intermediate" are used indifferently.

DETAILED DESCRIPTION AND ADDITIONAL EMBODIMENTS

According to a particular embodiment, $R_0$ represents a hydrogen atom, a halogen atom, a $(C_1-C_6)$alkyl, $(C_1-C_6)$haloalkyl, such as $CF_3$, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R$, CN or $NO_2$ group, or is selected from the group consisting of:

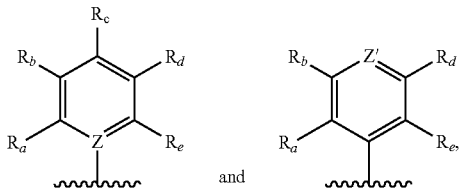

and wherein:
Z represents C or $N^+ A_z^-$ and Z' represents N or $N^+$—$R_c'$ $A_z^-$, wherein
$A_z^-$ represents a monovalent organic or inorganic anion, and
$R_c'$ represents a hydrogen atom or a $(C_1-C_6)$alkyl group,
$R_a$ and $R_e$ each represent, independently of each other, a hydrogen atom, a halogen atom, a $(C_1-C_{20})$alkyl, notably $(C_1-C_6)$alkyl, $(C_1-C_{20})$haloalkyl, notably $(C_1-C_6)$haloalkyl, aryl, heteroaryl, cycloalkyl, heterocycle, $OR_{22}$ or $SR_{23}$ group, and
$R_b$, $R_c$ and $R_d$ each represent, independently of each other, a hydrogen atom, a halogen atom or a $(C_1-C_{20})$alkyl, notably $(C_1-C_6)$alkyl, $(C_1-C_{20})$haloalkyl, notably $(C_1-C_6)$haloalkyl, cycloalkyl, heterocycle or $O(C_1-C_{20})$alkyl group.

According to another particular embodiment, $R_0$ represents a hydrogen atom, a halogen atom, a $(C_1-C_6)$alkyl, $(C_1-C_6)$haloalkyl, such as $CF_3$, cycloalkyl, heterocycle, $OR_5$, $SR_6$, $NR_7R_8$, CN, or $NO_2$ group, or is selected from the group consisting of:

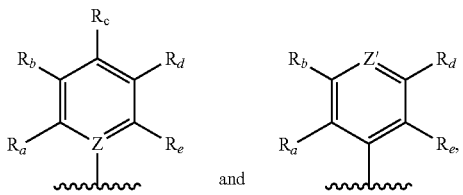

and wherein:
Z represents C or $N^+ A_z^-$ and Z' represents N or $N^+$—$R_c'$ $A_z^-$, wherein
$A_z^-$ represents a monovalent organic or inorganic anion, and
$R_c'$ represents a hydrogen atom or a $(C_1-C_6)$alkyl group,
$R_a$ and $R_e$ each represent, independently of each other, hydrogen atom, a halogen atom, a $(C_1-C_6)$alkyl, $(C_1-C_6)$haloalkyl, $OR_{22}$ or $SR_{23}$ group, and $R_b$, $R_c$ and $R_d$ each represent, independently of each other, a hydrogen atom, a halogen atom or a $(C_1-C_6)$alkyl or $(C_1-C_6)$haloalkyl group.

According to still another particular embodiment, $R_0$ represents a hydrogen atom, a halogen atom, a $(C_1-C_6)$alkyl, $(C_1-C_6)$haloalkyl, such as $CF_3$, CN, $NR_7R_8$, cycloalkyl, heterocycle or $NO_2$ group, or is:

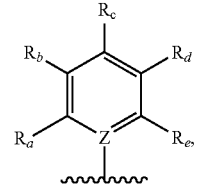

wherein:
Z represents C,
$R_a$ and $R_e$ each represent, independently of each other, hydrogen atom, a halogen atom, a $(C_1-C_{20})$alkyl, notably $(C_1-C_6)$alkyl, $(C_1-C_{20})$haloalkyl, notably $(C_1-C_6)$haloalkyl, cycloalkyl or $OR_{22}$ group, and
$R_b$, $R_c$ and $R_d$ each represent a hydrogen atom, a $(C_1-C_{20})$alkyl, notably $(C_1-C_6)$alkyl, $(C_1-C_{20})$haloalkyl, notably $(C_1-C_6)$haloalkyl or $O(C_1-C_{20})$alkyl group.

According to yet another particular embodiment, $R_0$ represents a hydrogen atom, a halogen atom, a $(C_1-C_6)$alkyl, $(C_1-C_6)$haloalkyl, such as $CF_3$, cycloalkyl, heterocycle, $OR_5$, $SR_6$, $NR_7R_8$, CN or $NO_2$ group, or is:

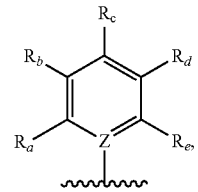

wherein:
Z represents C,
$R_a$ and $R_e$ each represent, independently of each other a hydrogen atom, a halogen atom, a $(C_1-C_6)$alkyl, $(C_1-C_6)$haloalkyl, $OR_{22}$ or $SR_{23}$ group, and
$R_b$, $R_c$ and $R_d$ each represent, independently of each other, a hydrogen atom, a halogen atom or a $(C_1-C_6)$alkyl or $(C_1-C_6)$haloalkyl group.

According to still another particular embodiment, $R_0$ represents a hydrogen atom, a halogen atom, a $(C_1-C_6)$alkyl, $(C_1-C_6)$haloalkyl, such as $CF_3$, CN or $NO_2$ group, or is:

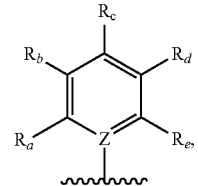

wherein:
Z represents C,
$R_a$ and $R_e$ each represent, independently of each other, a hydrogen atom, a halogen atom, a $(C_1-C_6)$alkyl or $(C_1-C_6)$haloalkyl group, and $R_b$, $R_c$ and $R_d$ each represent a hydrogen atom.

In the above embodiments, $R_a$ and $R_e$ are preferably the same.

In the above embodiments, $R_b$, $R_c$ and $R_d$ are preferably the same.

In a particular embodiment, $R_0$ represents a hydrogen atom, a halogen atom, a $(C_1-C_6)$alkyl, $(C_1-C_6)$haloalkyl, such as $CF_3$, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R_8$, CN or $NO_2$ group.

In another particular embodiment, $R_0$ represents a hydrogen atom, a halogen atom, a $(C_1-C_6)$alkyl, $(C_1-C_6)$haloalkyl, such as $CF_3$, cycloalkyl, heterocycle, $OR_5$, $SR_6$, $NR_7R_8$, CN, or $NO_2$ group, notably a hydrogen atom, a halogen atom, a $(C_1-C_6)$alkyl, $(C_1-C_6)$haloalkyl, such as $CF_3$, CN, $NR_7R_8$, cycloalkyl, heterocycle or $NO_2$ group, advantageously a hydrogen atom, a halogen atom, a $(C_1-C_6)$alkyl, $(C_1-C_6)$haloalkyl, such as $CF_3$, CN or $NO_2$ group.

In a preferred embodiment, $R_0$ represents a hydrogen atom, a $(C_1-C_6)$alkyl or a CN group, notably a hydrogen atom or a CN group, advantageously a hydrogen atom.

According to a particular embodiment, $R_1$ represents a halogen atom, a $(C_1-C_{20})$alkyl, notably $(C_1-C_{12})$alkyl, in particular $(C_1-C_6)$alkyl, $(C_1-C_{20})$haloalkyl, notably $(C_1-C_{12})$haloalkyl, in particular $(C_1-C_6)$haloalkyl, aryl, heteroaryl, cycloalkyl, heterocycle, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1.

According to another particular embodiment, $R_1$ represents a halogen atom, a $(C_1-C_{20})$alkyl, $(C_1-C_{20})$haloalkyl, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1.

According to still another particular embodiment, $R_1$ represents a halogen atom, a $(C_1-C_{12})$alkyl, notably $(C_1-C_6)$alkyl, $(C_1-C_{12})$haloalkyl, notably $(C_1-C_6)$haloalkyl, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1.

According to yet another particular embodiment, $R_1$ represents a halogen atom, a $(C_1-C_{20})$alkyl, notably $(C_1-C_{12})$alkyl, in particular $(C_1-C_{12})$alkyl, $(C_1-C_{20})$haloalkyl, notably $(C_1-C_{12})$haloalkyl, in particular $(C_1-C_6)$haloalkyl, $CH_2-OR_{24}$ or $OR_{26}$ group, preferably a $(C_1-C_6)$alkyl, $CH_2-OR_{24}$ or $OR_{26}$ group, notably a $(C_1-C_6)$alkyl or $OR_{26}$ group.

According to a particular embodiment, $R_4$ represents a halogen atom, a $(C_1-C_{20})$alkyl, notably $(C_1-C_{12})$alkyl, in particular $(C_1-C_{12})$alkyl, $(C_1-C_{20})$haloalkyl, notably $(C_1-C_{12})$haloalkyl, in particular $(C_1-C_6)$haloalkyl, aryl, heteroaryl, cycloalkyl, heterocycle, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1;

or both $R_4$ groups form together a bond or a chain selected from the group consisting of $-C(R_{42}R_{43})-$, $-(CH_2)_n-$, $-Si(R_{44}R_{45})-$ and $-Y-CH_2-CH_2-Y'-$, wherein:

Y and Y' each represent, independently of each other, O, S or NH, n is equal to 2 or 3, $R_{42}$ and $R_{43}$, each represent, independently of each other, a $(C_1-C_6)$alkyl or an aryl group, preferably a $(C_1-C_6)$alkyl group, and $R_{44}$ and $R_{45}$ each represent, independently of each other, a $(C_1-C_6)$alkyl or an aryl group, preferably a $(C_1-C_6)$alkyl group.

According to another particular embodiment, $R_4$ represents a halogen atom, a $(C_1-C_{20})$alkyl, notably $(C_1-C_{12})$alkyl, in particular $(C_1-C_{12})$alkyl, $(C_1-C_{20})$haloalkyl, notably $(C_1-C_{12})$haloalkyl, in particular $(C_1-C_6)$haloalkyl, $(CH_2)_mOR_{24}$, $(CH_2)_{m'}SR_{25}$, $OR_{26}$, $SR_{27}$ or $NR_{28}R_{29}$ group wherein m and m' are, independently of each other, equal to 1, 2 or 3, preferably 1;

or both $R_4$ groups form together a bond or a chain selected from the group consisting of $-C(R_{42}R_{43})-$, $-CH_2-CH_2-$, $-Si(R_{44}R_{45})-$ and $-O-CH_2-CH_2-$, wherein $R_{42}$ to $R_{45}$, each represent, independently of each other, a $(C_1-C_6)$alkyl group.

According to a particular embodiment, $R_4$ represents a halogen atom, a $(C_1-C_{20})$alkyl, notably $(C_1-C_{12})$alkyl, in particular $(C_1-C_6)$alkyl, $(C_1-C_{20})$haloalkyl, notably $(C_1-C_{12})$haloalkyl, in particular $(C_1-C_6)$haloalkyl, aryl, heteroaryl, cycloalkyl, heterocycle, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1.

According to another particular embodiment, $R_4$ represents a halogen atom, a $(C_1-C_{20})$alkyl, $(C_1-C_{20})$haloalkyl, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1.

According to still another particular embodiment, $R_4$ represents a halogen atom, a $(C_1-C_{12})$alkyl, notably $(C_1-C_6)$alkyl, $(C_1-C_{12})$haloalkyl, notably $(C_1-C_6)$haloalkyl, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1.

According to yet another particular embodiment, $R_4$ represents a halogen atom, a $(C_1-C_{20})$alkyl, notably $(C_1-C_{12})$alkyl, in particular $(C_1-C_{12})$alkyl, $(C_1-C_{20})$haloalkyl, notably $(C_1-C_{12})$haloalkyl, in particular $(C_1-C_6)$haloalkyl, $CH_2-OR_{24}$ or $OR_{26}$ group, preferably a $(C_1-C_6)$alkyl, $CH_2-OR_{24}$ or $OR_{26}$ group, notably a $(C_1-C_6)$alkyl or $OR_{26}$ group.

In a preferred embodiment, $R_1$ and $R_4$ are the same, and are as defined in any of the above embodiments.

Advantageously, when $R_1$ and $R_4$ are the same, and $R_0$ is:

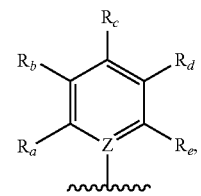

wherein Z represents C, at least one of $R_a$ and $R_e$ is not the same as $R_1$.

According to a particular embodiment, L represents a bond, or a group selected from the group consisting of:

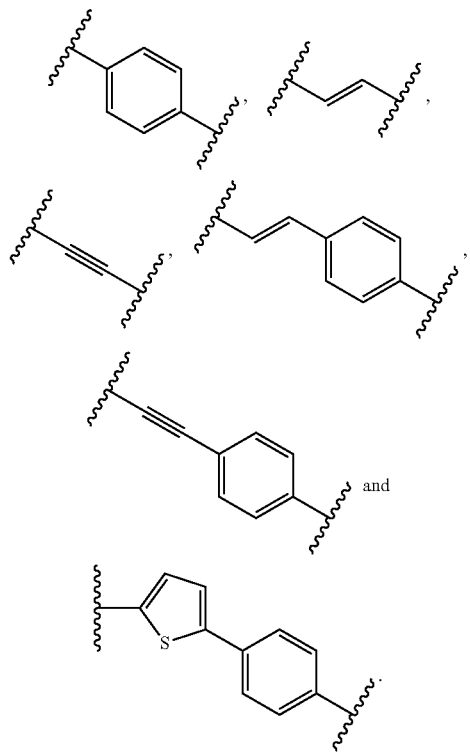

According to another particular embodiment, L represents a bond, or a group selected from the group consisting of:

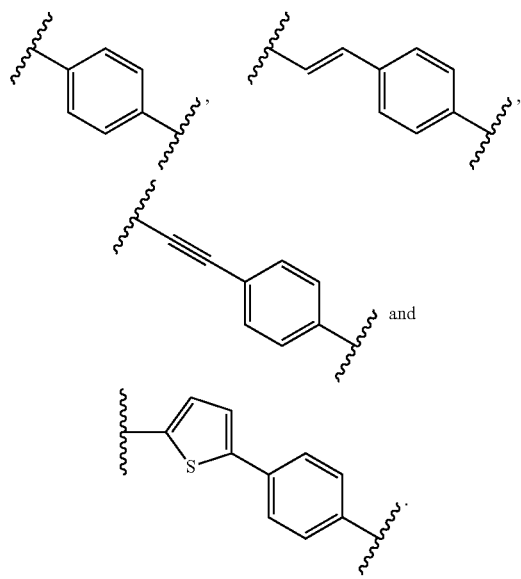

In a preferred embodiment, L represents a bond.

According to a particular embodiment, $R_2$ and $R_3$ each represent, independently of each other, a hydrogen atom, a halogen atom, a $(C_1$-$C_6)$alkyl or $(C_1$-$C_6)$haloalkyl group, or L represents:

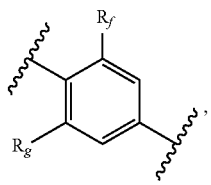

and $R_f$ and $R_2$, and $R_g$ and $R_3$ form together with the carbon atoms that carry them a cycloalkenyl or aryl group.

According to another particular embodiment $R_2$ and $R_3$ each represent, independently of each other, a hydrogen atom or a $(C_1$-$C_6)$alkyl group, preferably a hydrogen atom, or L represents:

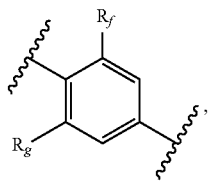

and $R_f$ and $R_2$, and $R_g$ and $R_3$ form together with the carbon atoms that carry them a cycloalkenyl or aryl group.

According to yet another particular embodiment, $R_2$ and $R_3$ each represent, independently of each other, a hydrogen atom, a halogen atom, a $(C_1$-$C_6)$alkyl or $(C_1$-$C_6)$haloalkyl group, notably a hydrogen atom or a $(C_1$-$C_6)$alkyl group, preferably $R_2$ and $R_3$ both represent a hydrogen atom.

Preferably, in the above embodiments, $R_2$ and $R_3$ are the same and are as defined in any of the above embodiments.

According to a particular embodiment, $R_N$ and $R_{N'}$ each represent, independently of each other, a $(C_7$-$C_{20})$alkyl or $(C_7$-$C_{20})$haloalkyl group, notably a $(C_7$-$C_{14})$alkyl or $(C_7$-$C_{14})$haloalkyl group, said group being optionally substituted by one or more groups selected from $OR_{62}$, $SR_{63}$ and $NR_{64}R_{65}$, or a group selected from the group consisting of:

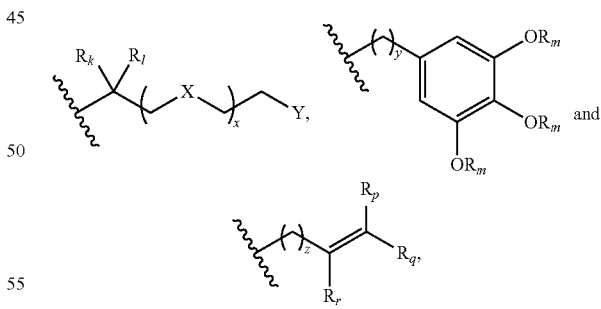

wherein:
X represents O, S or $NR_{57}$,
Y represents $OR_{58}$, $SR_{59}$ or $NR_{60}R_{61}$,
x is equal to 0, 1 or 2, preferably x is equal to 1 or 2,
y is equal to 0 or 1, 2 or 3,
z is equal to 1, 2 or 3,
$R_k$ and $R_l$ each represent, independently of each other, a hydrogen atom or a $(C_1$-$C_6)$alkyl group,
$R_m$ represents a $(C_1$-$C_{20})$alkyl group,
$R_r$ represents a hydrogen atom or a $(C_1$-$C_6)$alkyl group, $R_p$ and $R_q$ each represent, independently of each other, a hydrogen atom or a $(C_1-C_6)$alkyl group, $R_{57}$ to $R_{65}$ each represent, independently of each other, a hydrogen atom or a $(C_1-C_6)$alkyl group.

According to another particular embodiment, $R_N$ and $R_N'$ each represent, independently of each other, a $(C_7-C_{20})$alkyl or $(C_7-C_{20})$haloalkyl group, notably a $(C_7-C_{14})$alkyl or $(C_7-C_{14})$haloalkyl group, said group being optionally substituted by one or more groups selected from $OR_{62}$, $SR_{63}$ and $NR_{64}R_{65}$, or a group selected from the group consisting of:

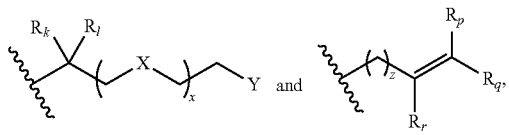

wherein:
X represents O, S or $NR_{57}$,
Y represents $OR_{58}$, $SR_{59}$ or $NR_{60}R_{61}$,
x is equal to 0, 1 or 2, preferably x is equal to 1 or 2,
z is equal to 1, 2 or 3,
$R_k$ and $R_l$ each represent, independently of each other, a hydrogen atom or a $(C_1-C_6)$alkyl group,
$R_r$ represents a hydrogen atom or a $(C_1-C_6)$alkyl group,
$R_p$ and $R_q$ each represent, independently of each other, a hydrogen atom or a $(C_1-C_6)$alkyl group,
$R_{57}$ to $R_{65}$ each represent, independently of each other, a hydrogen atom or a $(C_1-C_6)$alkyl group.

In a particular embodiment, $R_N$ and $R_N'$ each represent, independently of each other,

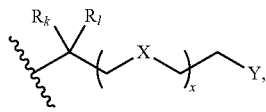

wherein:
$R_k$ and $R_l$ both represent a hydrogen atom,
x is equal to 0, and
Y is selected from the group consisting of OH, $OCH_3$, $NH_2$, $NHCH_3$ and $N(CH_3)_2$.

In a preferred embodiment, $R_N$ and $R_N'$ are the same, and are as defined in any of the above embodiments.

In all of the above embodiments:
$R_5$ to $R_8$, $R_{11}$ to $R_{15}$, $R_{24}$, $R_{25}$, $R_{28}$, $R_{29}$, $R_{32}$, $R_{36}$, $R_{38}$, $R_{39}$, $R_{49}$; $R_{51}$ and $R_{52}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, preferably a hydrogen atom or a $(C_1-C_6)$alkyl group, said group being optionally substituted by one or more groups selected from a halogen atom, a $(C_1-C_6)$alkyl, $(C_1-C_6)$haloalkyl, $OR_{64}$, $SR_{65}$ and $NR_{66}R_{67}$ group, wherein $R_{64}$ to $R_{67}$ each represent, independently of each other, a hydrogen atom or a $(C_1-C_6)$alkyl group;
in particular, $R_5$ to $R_8$, $R_{11}$ to $R_{15}$, $R_{24}$, $R_{25}$, $R_{28}$, $R_{29}$, $R_{32}$, $R_{36}$, $R_{38}$, $R_{39}$, $R_{49}$; $R_{51}$ and $R_{52}$ each represent, independently of each other, a $(C_1-C_6)$alkyl group; and
$R_{22}$, $R_{23}$, $R_{26}$ and $R_{27}$ each represent, independently of each other a hydrogen atom, a $(C_1-C_{20})$alkyl, notably $(C_1-C_{12})$alkyl, in particular $(C_1-C_6)$alkyl, $(C_1-C_{20})$haloalkyl, notably $(C_1-C_{12})$haloalkyl, in particular $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, preferably a hydrogen atom or a $(C_1-C_{20})$alkyl, notably $(C_1-C_{12})$alkyl, in particular $(C_1-C_6)$alkyl group, said group being optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group, wherein $R_{66}$ to $R_{69}$ each represent, independently of each other, a hydrogen atom or a $(C_1-C_6)$alkyl group; in particular, $R_{22}$, $R_{23}$, $R_{26}$ and $R_{27}$ each represent, independently of each other a $(C_1-C_{20})$alkyl, notably $(C_1-C_{12})$alkyl, in particular $(C_1-C_6)$alkyl group.

In particular, the invention relates to a compound of formula (I), wherein:

$R_0$ represents a hydrogen atom, a halogen atom, a $(C_1-C_6)$alkyl, $(C_1-C_6)$haloalkyl, such as $CF_3$, cycloalkyl, heterocycle, $OR_5$, $SR_6$, $NR_7R_8$, CN or $NO_2$ group, or is:

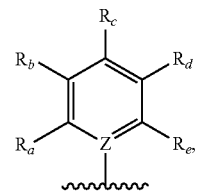

wherein:
Z represents C,
$R_a$ and $R_e$ are the same and represent a hydrogen atom, a halogen atom, a $(C_1-C_{20})$alkyl, notably $(C_1-C_6)$alkyl, $(C_1-C_{20})$haloalkyl, notably $(C_1-C_6)$haloalkyl, $OR_{22}$ or $SR_{23}$ group, and
$R_b$, $R_c$ and $R_d$ each represent, independently of each other, a hydrogen atom, a halogen atom or a $(C_1-C_6)$alkyl, $(C_1-C_6)$haloalkyl or $O(C_1-C_{20})$alkyl group, preferably $R_b$, $R_c$ and $R_d$ are the same;

$R_1$ and $R_4$ are the same and represent a halogen atom, a $(C_1-C_{20})$alkyl, notably $(C_1-C_{12})$alkyl, in particular $(C_1-C_6)$alkyl, $(C_1-C_{20})$haloalkyl, notably $(C_1-C_{12})$haloalkyl, in particular $(C_1-C_6)$haloalkyl, aryl, heteroaryl, cycloalkyl, heterocycle, $(CH_2)_mOR_{24}$, $(CH_2)_mSR_{25}$, $OR_{26}$, $SR_{27}$ or $NR_{28}R_{29}$ group, wherein m and m' are, independently of each other, equal to 1, 2 or 3, preferably 1;

L represents a bond, or a group selected from the group consisting of:

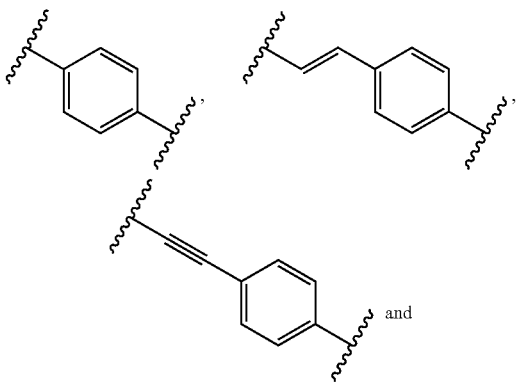

-continued

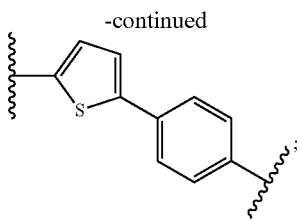

$R_N$ and $R_{N'}$ are the same and represent a $(C_7-C_{20})$alkyl or $(C_7-C_{20})$haloalkyl group, notably a $(C_7-C_{14})$alkyl or $(C_7-C_{14})$haloalkyl group, said group being optionally substituted by one or more groups selected from $OR_{62}$, $SR_{63}$ and $NR_{64}R_{65}$, or a group selected from the group consisting of:

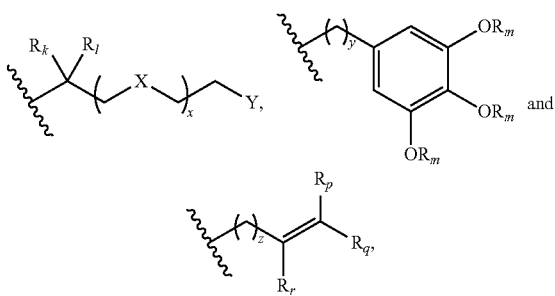

wherein:
X represents O, S or $NR_{57}$,
Y represents $OR_{58}$, $SR_{59}$ or $NR_{60}R_{61}$,
x is equal to 0, 1 or 2, preferably x is equal to 1 or 2,
y is equal to 0 or 1, 2 or 3,
z is equal to 1, 2 or 3,
$R_k$ and $R_l$ each represent, independently of each other, a hydrogen atom or a $(C_1-C_6)$alkyl group,
$R_m$ represents a $(C_1-C_{20})$alkyl group,
$R_r$ represents a hydrogen atom or a $(C_1-C_6)$alkyl group,
$R_p$ and $R_q$ each represent, independently of each other, a hydrogen atom or a $(C_1-C_6)$alkyl group,
$R_{57}$ to $R_{65}$ each represent, independently of each other, a hydrogen atom or a $(C_1-C_6)$alkyl group.

Notably, the invention relates to a compound of formula (I), wherein:
$R_0$ represents a hydrogen atom, a halogen atom, a $(C_1-C_6)$alkyl, $(C_1-C_6)$haloalkyl, such as $CF_3$, CN or $NO_2$ group, or is:

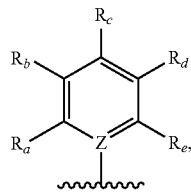

wherein:
Z represents C,
$R_a$ and $R_e$ are the same and represent a hydrogen atom, a halogen atom, a $(C_1-C_6)$alkyl or $(C_1-C_6)$haloalkyl group, and
$R_b$, $R_c$ and $R_d$ each represent a hydrogen atom;

$R_1$ and $R_4$ are the same and represent a halogen atom, a $(C_1-C_{20})$alkyl, notably $(C_1-C_{12})$alkyl, in particular $(C_1-C_6)$alkyl, $(C_1-C_{20})$haloalkyl, notably $(C_1-C_{12})$haloalkyl, in particular $(C_1-C_6)$haloalkyl, aryl, heteroaryl, cycloalkyl, heterocycle, $(CH_2)_mOR_{24}$, $(CH_2)_mSR_{25}$, $OR_{26}$, $SR_{27}$ or a halogen atom, a $(C_1-C_{20})$alkyl, notably $(C_1-C_{12})$alkyl, in particular $(C_1-C_{12})$alkyl, $(C_1-C_{20})$haloalkyl, notably $(C_1-C_{12})$haloalkyl, in particular $(C_1-C_6)$haloalkyl, $CH_2$—$OR_{24}$ or $OR_{26}$ group, preferably a $(C_1-C_6)$alkyl, $CH_2$—$OR_{24}$ or $OR_{26}$ group, notably a $(C_1-C_6)$alkyl or $OR_{26}$ group;

L represents a bond;

$R_N$ and $R_{N'}$ are the same and represent a $(C_7-C_{20})$alkyl or $(C_7-C_{20})$haloalkyl group, notably a $(C_7-C_{14})$alkyl or $(C_7-C_{14})$haloalkyl group, said group being optionally substituted by one or more groups selected from $OR_{62}$, $SR_{63}$ and $NR_{64}R_{65}$, or a group selected from the group consisting of:

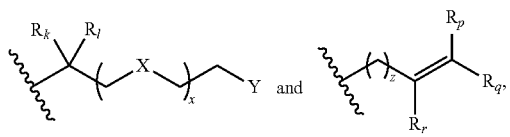

wherein:
X represents O, S or $NR_{57}$,
Y represents $OR_{58}$, $SR_{59}$ or $NR_{60}R_{61}$,
x is equal to 0, 1 or 2, preferably x is equal to 1 or 2,
z is equal to 1, 2 or 3,
$R_k$ and $R_l$ each represent, independently of each other, a hydrogen atom or a $(C_1-C_6)$alkyl group,
$R_r$ represents a hydrogen atom or a $(C_1-C_6)$alkyl group,
$R_p$ and $R_q$ each represent, independently of each other, a hydrogen atom or a $(C_1-C_6)$alkyl group,
$R_{57}$ to $R_{65}$ each represent, independently of each other, a hydrogen atom or a $(C_1-C_6)$alkyl group.

Preferably, in the above embodiments, when $R_0$ is:

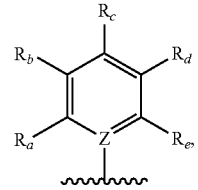

wherein Z represents C, $R_a$ is not the same as $R_1$.

In a particular embodiment, the invention relates to a compound of formula (I), wherein:
$R_0$ represents a hydrogen atom, a halogen atom, a $(C_1-C_6)$alkyl, $(C_1-C_6)$haloalkyl, such as $CF_3$, cycloalkyl, heterocycle, $OR_5$, $SR_6$, $NR_7R_8$, CN, or $NO_2$ group, notably a hydrogen atom, a halogen atom, a $(C_1-C_6)$alkyl, $(C_1-C_6)$haloalkyl, such as $CF_3$, CN, $NR_7R_8$, cycloalkyl, heterocycle or $NO_2$ group, advantageously a hydrogen atom, a halogen atom, a $(C_1-C_6)$alkyl, $(C_1-C_6)$haloalkyl, such as $CF_3$, CN or $NO_2$ group;

$R_1$ and $R_4$ are the same and represent a halogen atom, a $(C_1-C_{20})$alkyl, notably $(C_1-C_{12})$alkyl, in particular $(C_1-C_6)$alkyl, $(C_1-C_{20})$haloalkyl, notably $(C_1-C_{12})$haloalkyl, in particular $(C_1-C_6)$haloalkyl, aryl, heteroaryl, cycloalkyl, heterocycle, $(CH_2)_mOR_{24}$, $(CH_2)_mSR_2$, OR$_{26}$, SR$_{27}$ or NR$_{28}$R$_{29}$ group, wherein m and m' are, independently of each other, equal to 1, 2 or 3, preferably 1;

L represents a bond, or a group selected from the group consisting of:

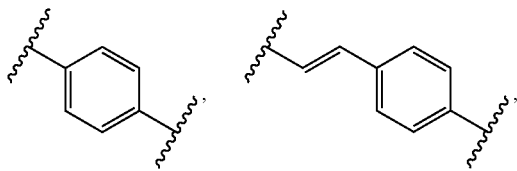

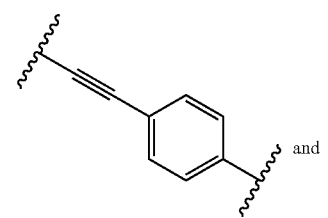

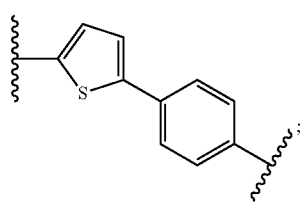

R$_N$ and R$_N$' are the same and represent a (C$_7$-C$_{20}$)alkyl or (C$_7$-C$_{20}$)haloalkyl group, notably a (C$_7$-C$_{14}$)alkyl or (C$_7$-C$_{14}$)haloalkyl group, said group being optionally substituted by one or more groups selected from OR$_{62}$, SR$_{63}$ and NR$_{64}$R$_{65}$, or a group selected from the group consisting of:

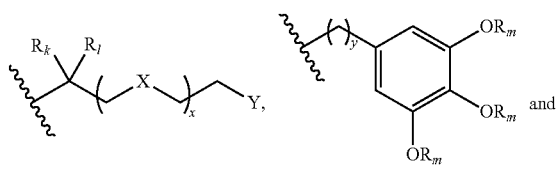

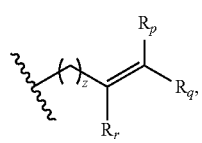

wherein:
X represents O, S or NR$_{57}$,
Y represents OR$_{58}$, SR$_{59}$ or NR$_{60}$R$_{61}$,
x is equal to 0, 1 or 2, preferably x is equal to 1 or 2,
y is equal to 0 or 1, 2 or 3,
z is equal to 1, 2 or 3,
R$_k$ and R$_l$ each represent, independently of each other, a hydrogen atom or a (C$_1$-C$_6$)alkyl group,
R$_m$ represents a (C$_1$-C$_{20}$)alkyl group,
R$_r$ represents a hydrogen atom or a (C$_1$-C$_6$)alkyl group,
R$_p$ and R$_q$ each represent, independently of each other, a hydrogen atom or a (C$_1$-C$_6$)alkyl group,
R$_{57}$ to R$_{65}$ each represent, independently of each other, a hydrogen atom or a (C$_1$-C$_6$)alkyl group.

In another particular embodiment, the invention relates to a compound of formula (I), wherein:

R$_0$ represents a hydrogen atom, a (C$_1$-C$_6$)alkyl or a CN group, notably a hydrogen atom or a CN group, advantageously a hydrogen atom;

R$_1$ and R$_4$ are the same and represent a halogen atom, a (C$_1$-C$_{20}$)alkyl, notably (C$_1$-C$_{12}$)alkyl, in particular (C$_1$-C$_{12}$)alkyl, (C$_1$-C$_{20}$)haloalkyl, notably (C$_1$-C$_{12}$)haloalkyl, in particular (C$_1$-C$_6$)haloalkyl, CH$_2$—OR$_{24}$ or OR$_{26}$ group, preferably a (C$_1$-C$_6$)alkyl, CH$_2$—OR$_{24}$ or OR$_{26}$ group, notably a (C$_1$-C$_6$)alkyl or OR$_{26}$ group;

L represents a bond;

R$_N$ and R$_N$' are the same and represent a (C$_7$-C$_{20}$)alkyl or (C$_7$-C$_{20}$)haloalkyl group, notably a (C$_7$-C$_{14}$)alkyl or (C$_7$-C$_{14}$)haloalkyl group, said group being optionally substituted by one or more groups selected from OR$_{62}$, SR$_{63}$ and NR$_{64}$R$_{65}$, or a group selected from the group consisting of:

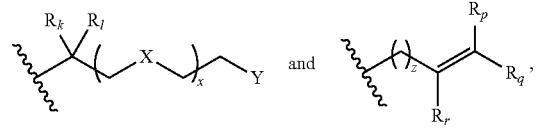

wherein:
X represents O, S or NR$_{57}$,
Y represents OR$_{58}$, SR$_{59}$ or NR$_{60}$R$_{61}$,
x is equal to 0, 1 or 2, preferably x is equal to 1 or 2,
z is equal to 1, 2 or 3,
R$_k$ and R$_l$ each represent, independently of each other, a hydrogen atom or a (C$_1$-C$_6$)alkyl group,
R$_r$ represents a hydrogen atom or a (C$_1$-C$_6$)alkyl group,
R$_p$ and R$_q$ each represent, independently of each other, a hydrogen atom or a (C$_1$-C$_6$)alkyl group,
R$_{57}$ to R$_{65}$ each represent, independently of each other, a hydrogen atom or a (C$_1$-C$_6$)alkyl group;

In all of the above embodiments, R$_5$ to R$_8$, R$_{11}$ to R$_{15}$, R$_{22}$ to R$_{29}$, R$_{32}$, R$_{36}$, R$_{38}$, R$_{39}$, R$_{49}$; R$_{51}$ and R$_{52}$ are as defined above. In particular, R$_5$ to R$_8$, R$_{11}$ to R$_{15}$, R$_{24}$, R$_{25}$, R$_{28}$, R$_{29}$, R$_{32}$, R$_{36}$, R$_{38}$, R$_{39}$, R$_{49}$; R$_{51}$ and R$_{52}$ each represent, independently of each other, a (C$_1$-C$_6$)alkyl group; and R$_{22}$, R$_{23}$, R$_{26}$ and R$_{27}$ each represent, independently of each other a (C$_1$-C$_{20}$)alkyl, notably (C$_1$-C$_{12}$)alkyl, in particular (C$_1$-C$_6$) alkyl group.

In another particular embodiment, a compound of the present invention is chosen among the following compounds:

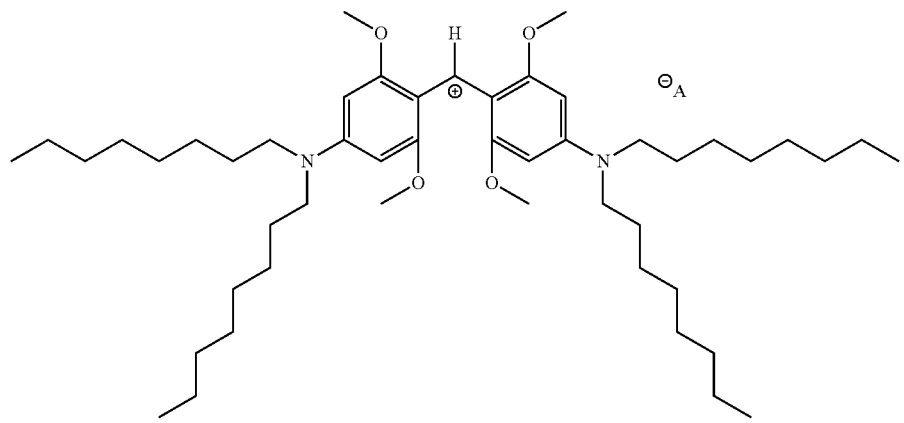
1
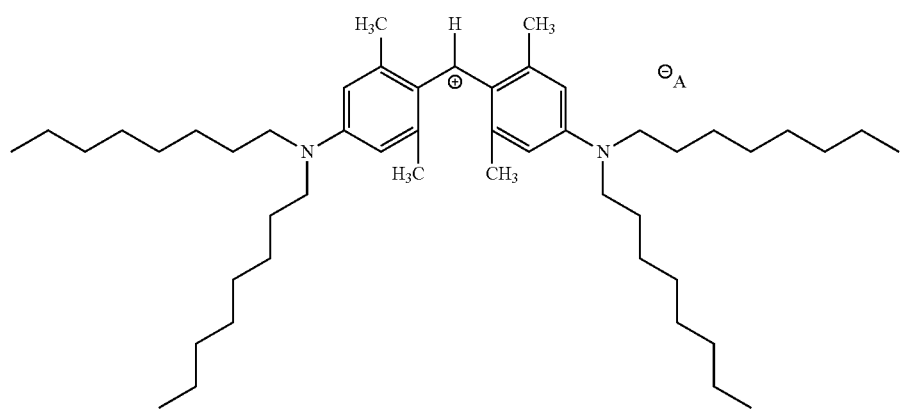
2
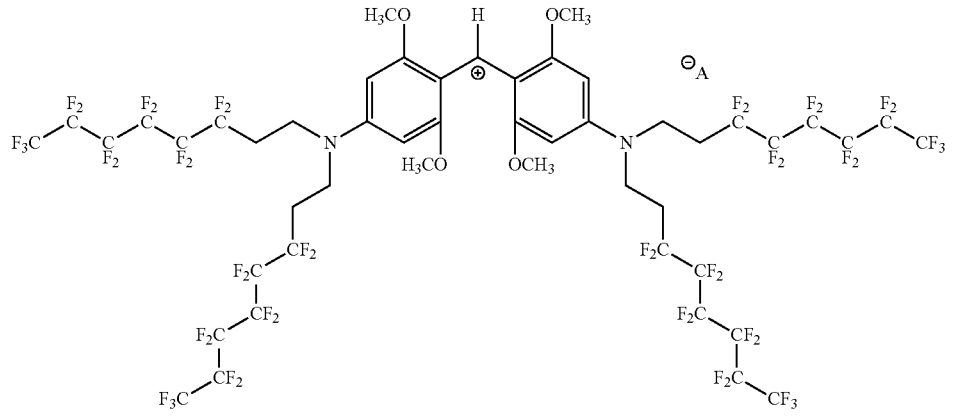
3
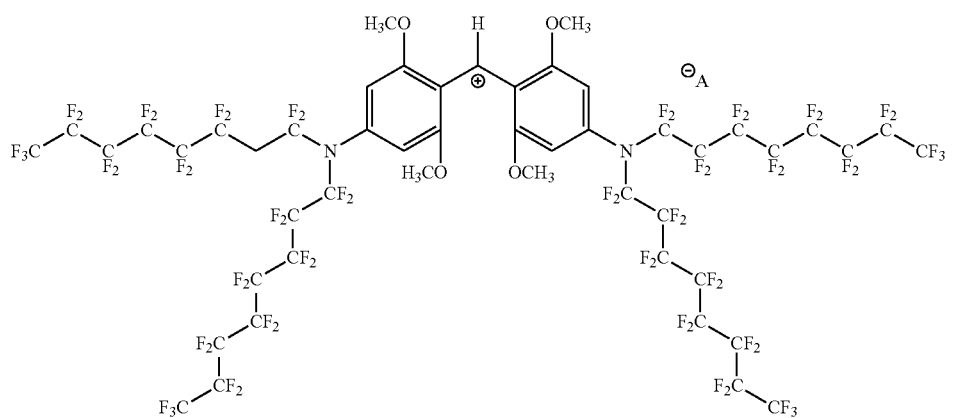
4

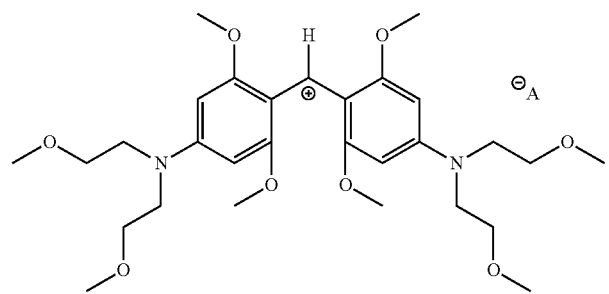
5
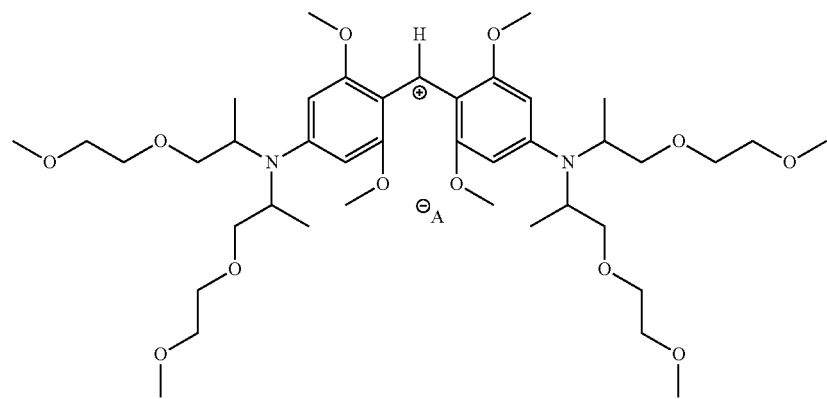
6
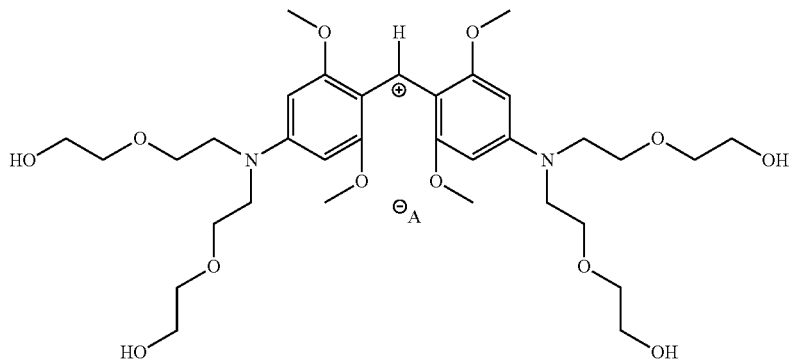
7
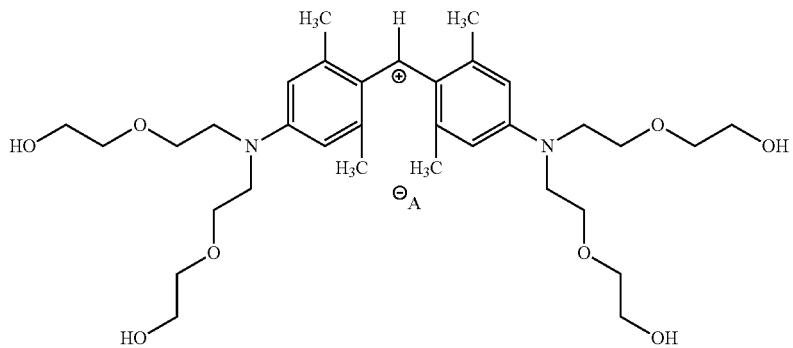
8

-continued
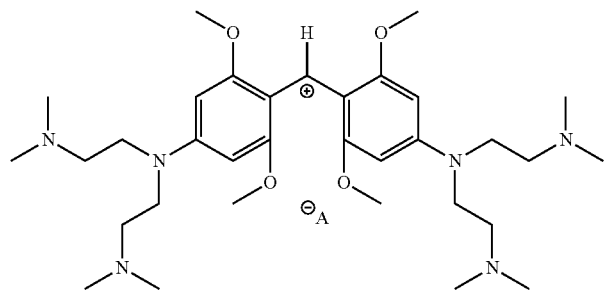
9
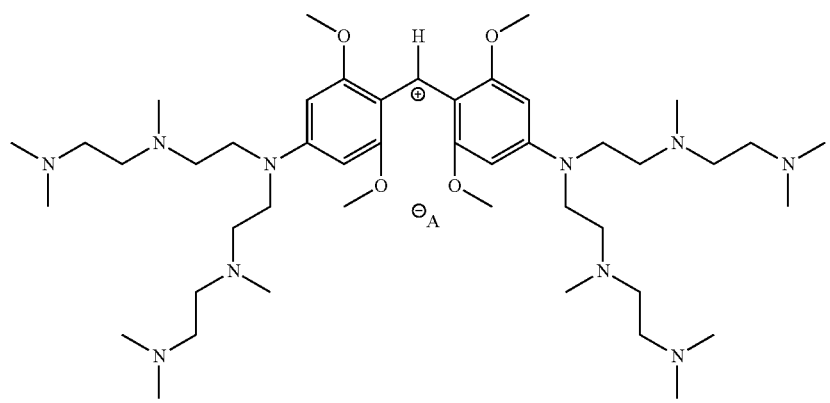
10
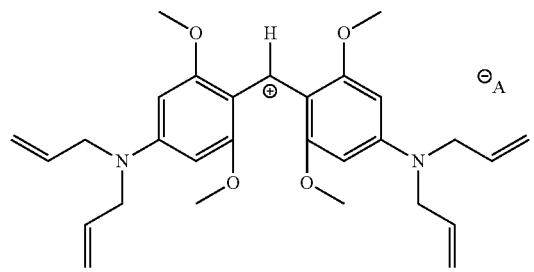
11
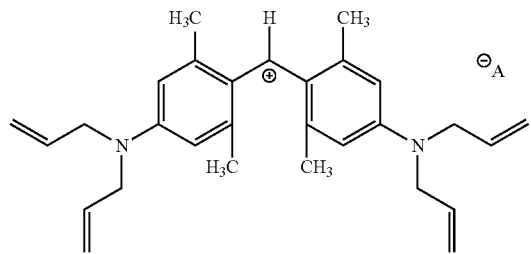
12
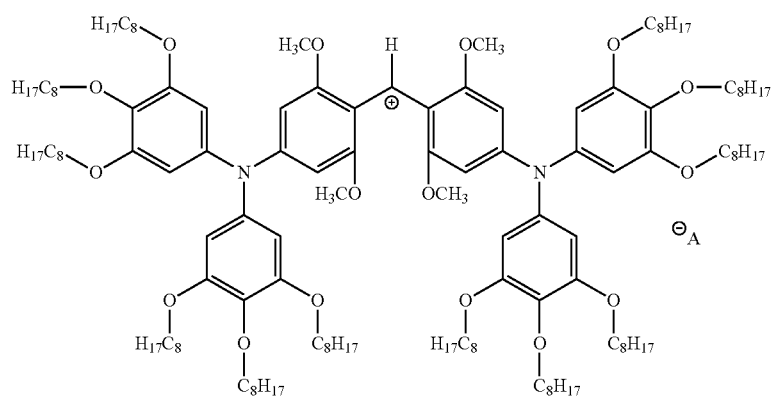
13

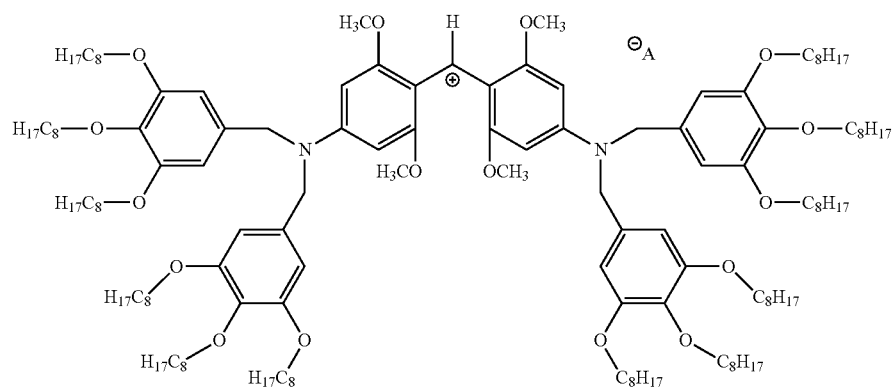
14
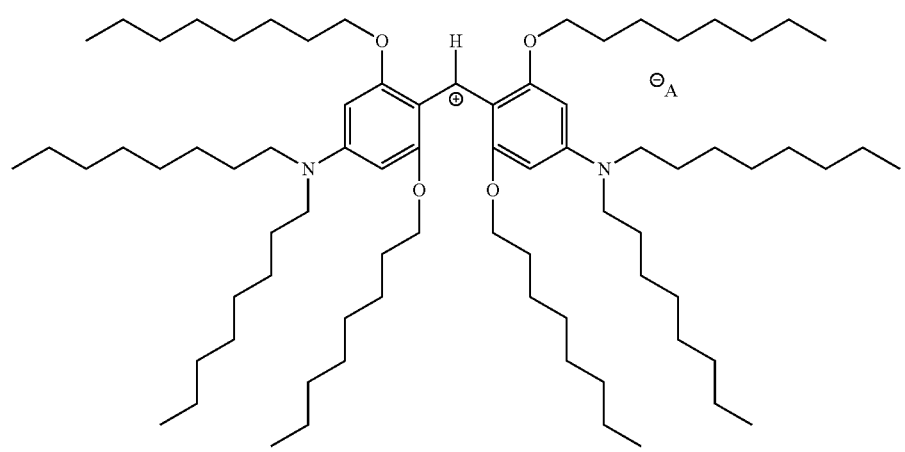
15
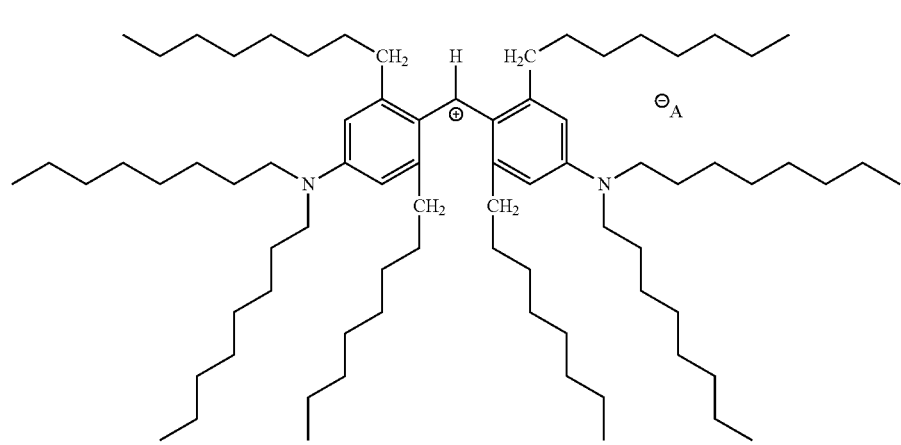
16

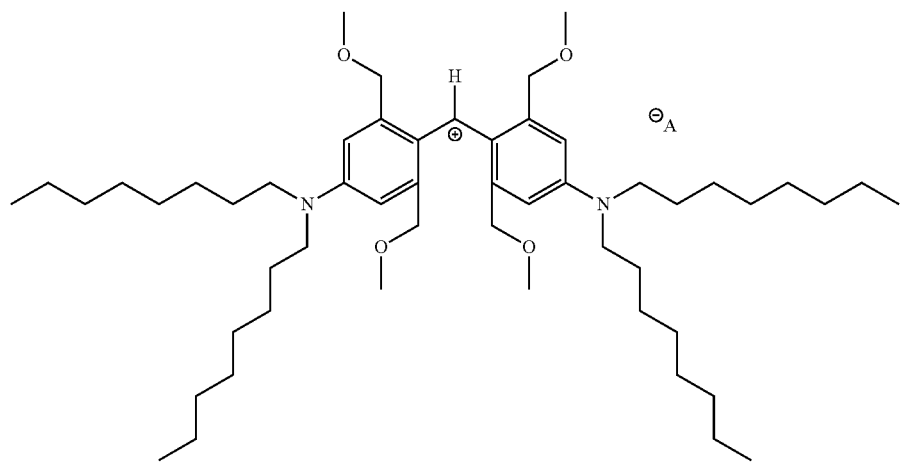
17
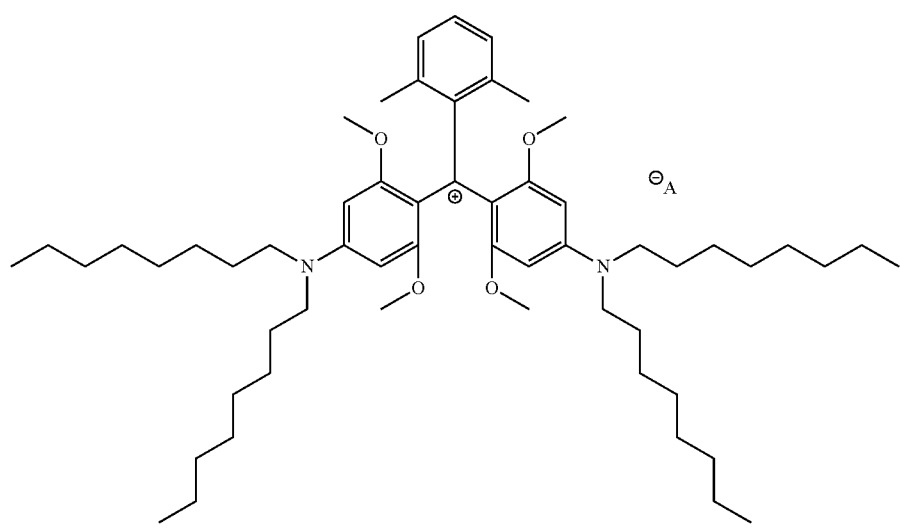
18
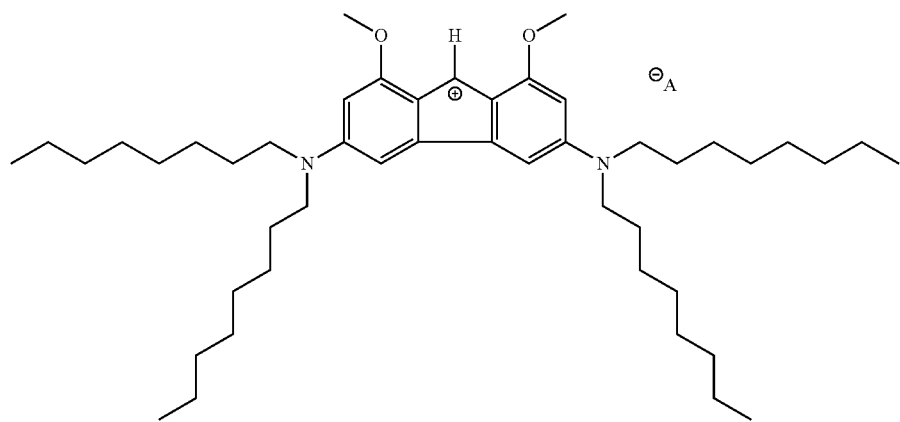
19

-continued
20
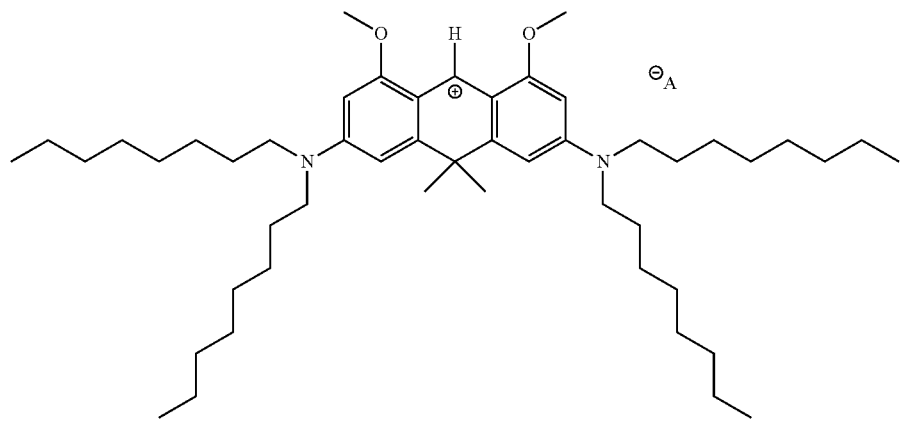
21
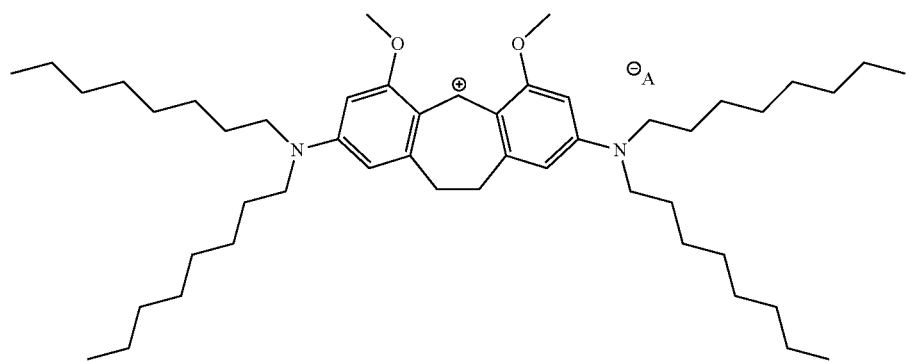
22
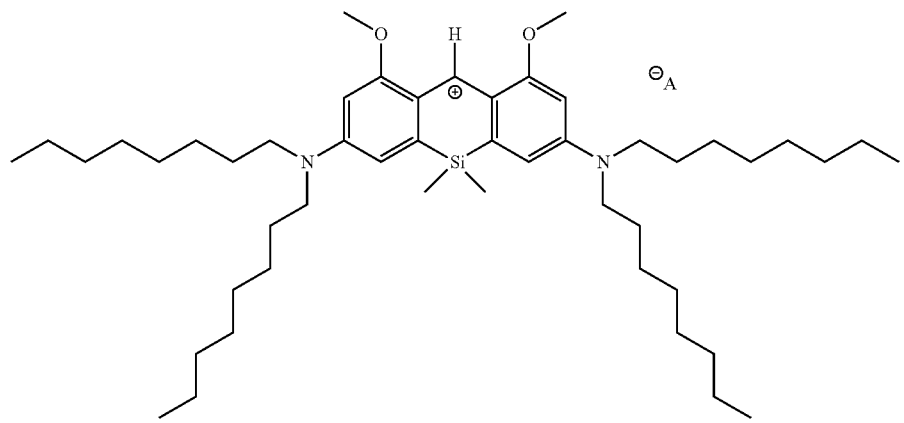
23
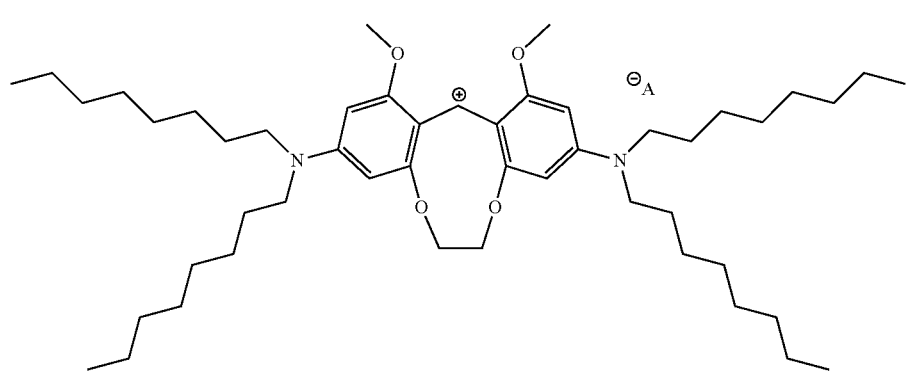

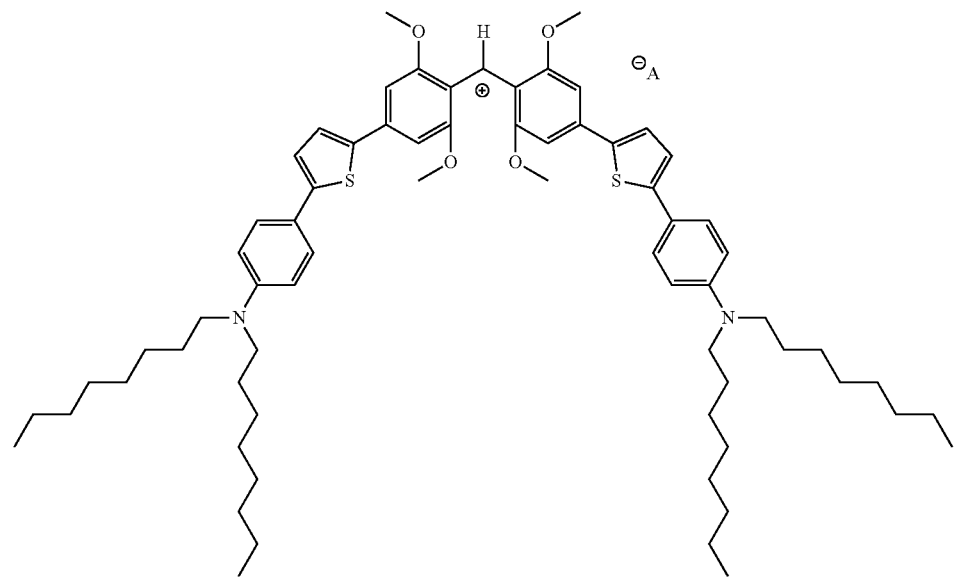
24
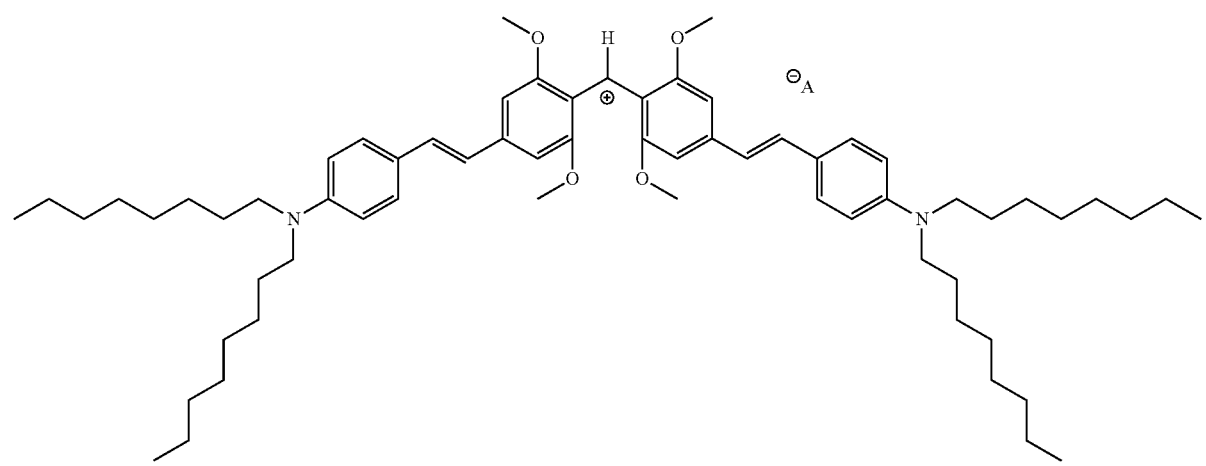
25
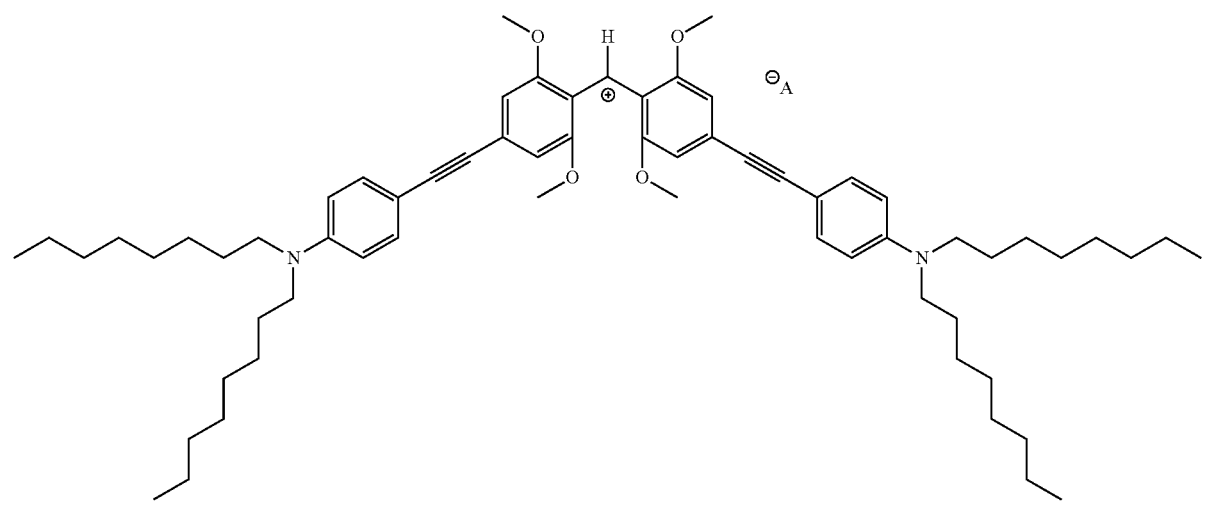
26

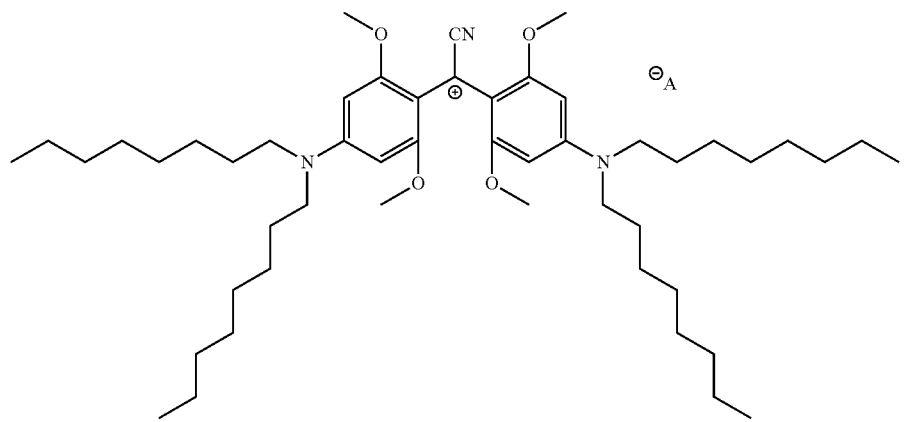
27
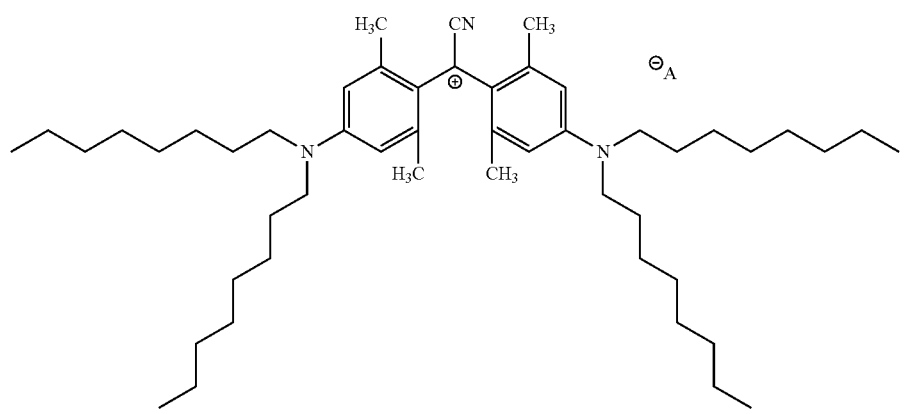
28
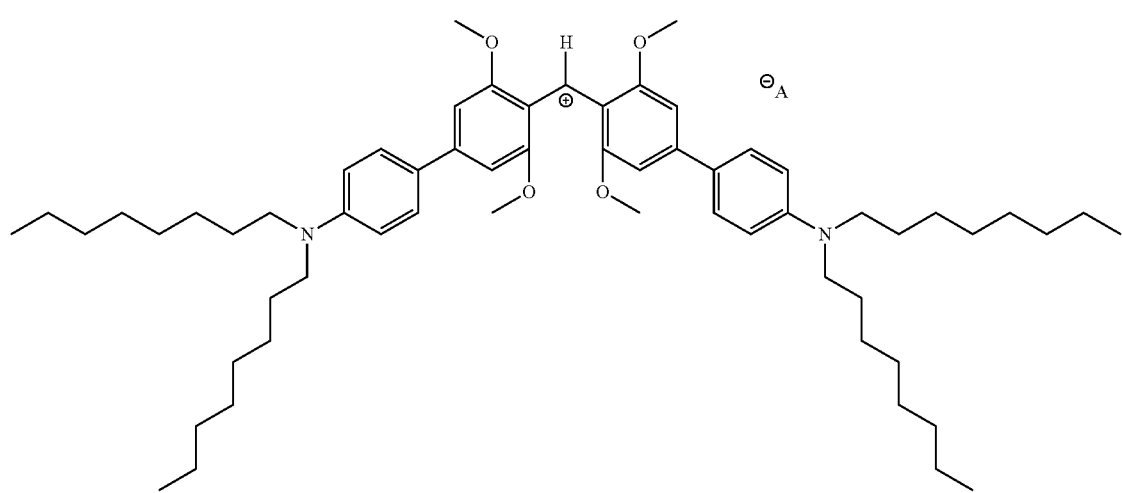
29

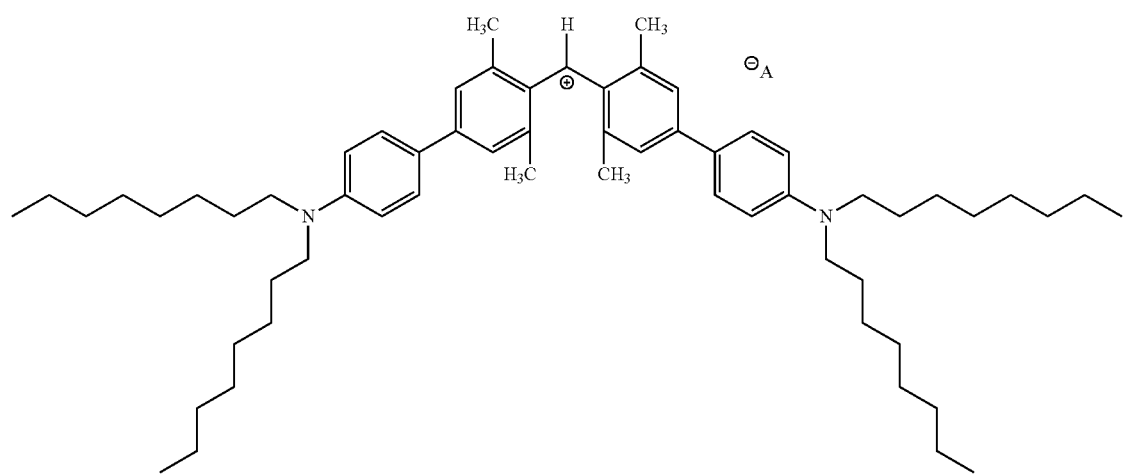
30
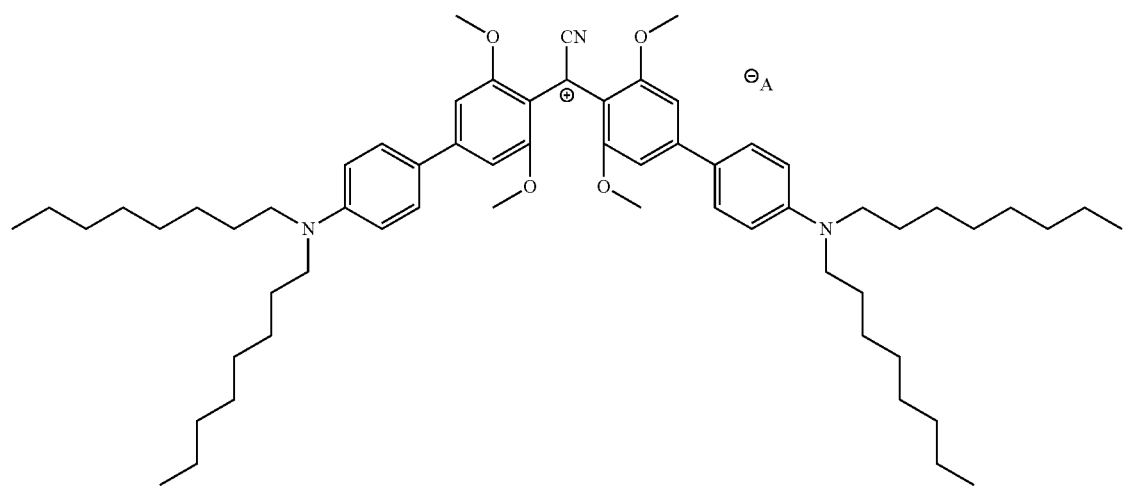
31
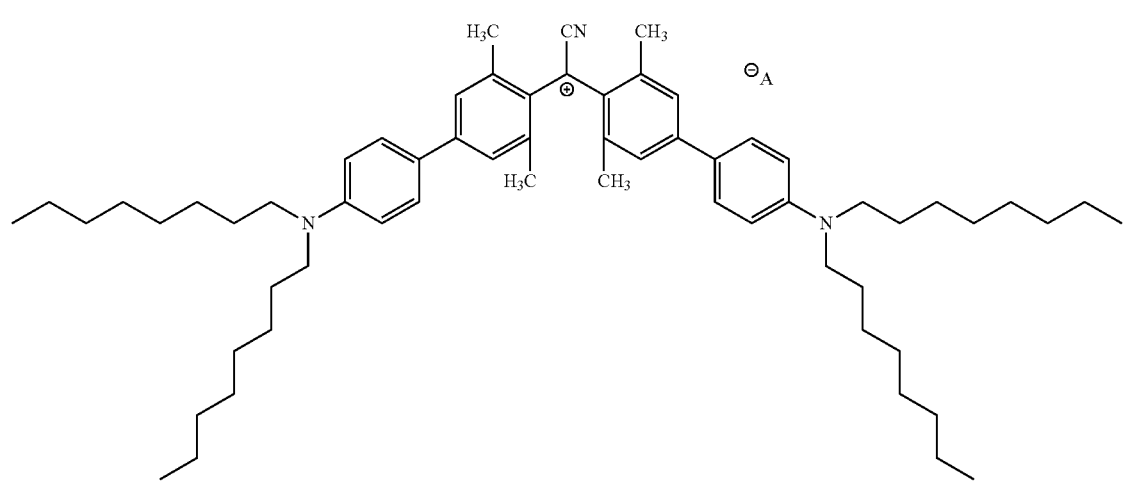
32

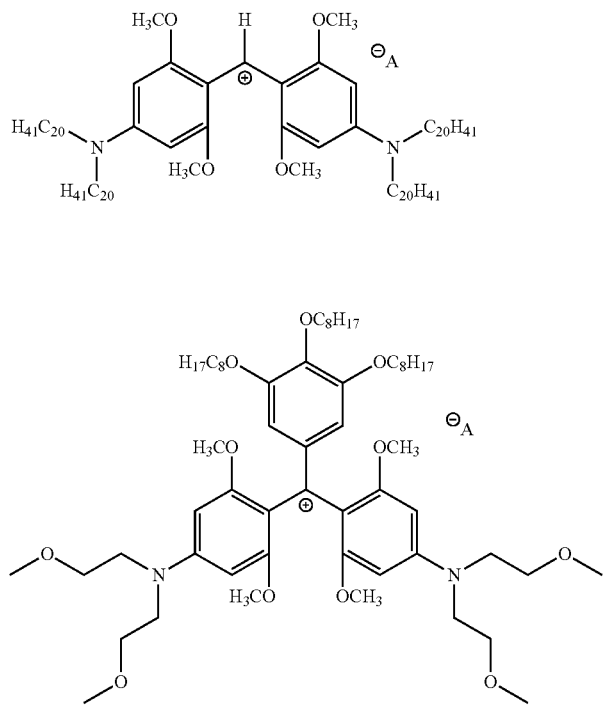

Notably, a compound of the present invention is chosen among compounds 1, 4, 5, 9, 11 to 13, 27, 33, and 35, in particular among compounds 1, 4, 5, 9, 11, 12, 33, 34 and $\overrightarrow{35}$ advantageously among compounds 1, 5, 11, 12, 33, 34 and 35.

In all of the above embodiments and compounds, A⁻ represents a monovalent, organic or inorganic anion. In particular, A⁻ represents a hexafluorophosphate, tetrafluoroborate, tetraphenylborate, 2,3-dichloro-5,6-dicyano-4-hydroxyphenolate (DDQH⁻), halide or triflate anion, preferably a DDQH⁻ or hexafluorophosphate anion.

The invention also relates to the use of a compound according to the invention as a chromophore.

The term "chromophore" here refers to a molecule whose electronic absorption is at least situated in the spectral range of visible light (between ca. 400 nm and 700 nm), which is not exclusive of absorption in the near-UV and near-infrared domains.

As regards molecular chromophores, possible applications span from bioimaging purposes, notably as a dye to stain cells, tissues or fibrillar structures like those associated with a variety of neurodegenerative diseases, among which Alzheimer's disease, to the conception of new high performance optical limiter devices relying on non-linear optical properties displayed by compounds objects of the invention.

The invention also relates to a material comprising at least one compound according to the invention.

As it has been previously mentioned, the compounds according to the invention tend to self-assemble and form supramolecular materials.

Said materials can be in the form of crystals, thin films, flakes, platelets or layers and other forms of low-dimensional materials (interfacial film) that may result from self-assembly of chromophores.

Said supramolecular materials can be a pigment, advantageously a pigment of interest for its special optical effect(s).

Accordingly, the invention relates to the use of the compounds (or said supramolecular materials) according to the invention as a pigment or a dye.

More particularly, as exemplified in the experimental section, because of their special optical effect(s), said compounds are useful as a luster pigment; even more specifically as a metal effect pigment and/or a pearl luster pigment.

The invention also relates to a metal-like particle that comprises at least one compound according to the invention. Said particle might be embedded within a matrix, including but not limited to, polymers, plastics, glass, coating or cosmetic formulation, ceramics, enamels.

The invention also relates to a reflective, photonic, nanophotonic or optoelectronic device, that comprises at least one compound according to the invention.

In the context of the present invention, a reflective device can notably be a solid or a liquid mirror.

The term "mirror" here refers to a reflective surface and includes, but is not limited to, a large mirror (e.g. for astronomy or LIDAR technologies), a smart mirror (displaying one or several of the following features: flexibility, transportability, switchability) or an organic-based metal-like liquid film.

The term "organic-based metal-like liquid film" or OMELLF here refers to an organic molecule able to self-assemble to display a reflective surface either at a liquid/liquid interface or at an air/liquid interface by analogy with the reflective surfaces obtained with a low-melting point metal/metal alloy or with an aqueous colloidal preparation of metallic nanoparticles in presence of an appropriate ligand.

The invention also relates to an organic-based metal-like liquid film (OMELLF) that comprises at least one compound according to the invention.

Liquid mirrors can notably be easily achieved notably by simple drop-casting or spraying of pure compound (dissolved in a suitable deposition medium) onto a stirred suitable fluid (e.g. pure water, an aqueous ion-saturated solution, ethylene glycol or another hydrophilic viscous fluid, silicone oil or another hydrophobic viscous fluid, ionic liquids) or by subsequent transfer of such a self-assembled reflective film.

The invention also relates to metal-like reflective coating that comprises at least one compound according to the invention.

Metal-like reflective coatings can be easily achieved notably by simple drop-casting, doctor-blade coating, bar-coating, spin-coating, dip-coating or vacuum deposition of pure compound dissolved or suspended in a suitable deposition medium.

Reflectance spectra can be recorded with dedicated equipment in order to evaluate quantitatively the efficiency of the thin film to reflect light as a function of wavelength and incidence angle.

The invention also relates to metal-like glittering surface that comprises at least one compound according to the invention Metal-like glittering surfaces can be easily achieved notably by incorporating pure compound particles (of variable size) in a non-solubilizing suitable medium (e.g. in a lacquer or in plastics).

The range of application media for the pigments with special optical effects (and in some cases for their constitutive chromophores) according to the invention includes notably paints, coatings, printing inks, cosmetic formulations (e.g. nail lacquers) as well as implementations in the recreational and artistic (e.g. enamel) fields.

Another possible application is the design of pigments for conception of new security inks that enter for example in the fabrication of banknotes, official identity documents, postage stamps, tax banderoles, security labels or product markings.

Another possible application is the design of pigments and/or materials for the conception of new optical reflectors that enter for example in the fabrication of small mirrors for optics/microscopy/interferometry, sensors, very small mirrors for lasers (optical cavity) or mirrors for nomad and transportable devices.

Another possible application is the design of pigments, materials and/or inks for the conception of VCSEL (vertical-cavity surface-emitting laser) or optical waveguides to be included in printed and/or integrated photonic circuits and/or devices, or excitonic nanostructures.

Another possible application is the design of large liquid mirrors for astronomy (e.g. as part of a telescope on earth or in space) or meteorology/atmospheric sciences (e.g. as part of a LIDAR for "LIght Detection And Ranging»).

Another possible application is the design of a liquid mirror for metrology and precision calibration purposes (e.g. as part of a telecentric scanning lens).

Another possible application is the design of a smart mirror (displaying one or several of the following features: flexibility, transportability, switchability), or of a smart window.

Another possible application is the design of a renewable liquid mirror for applications where high-power pulses of radiation able to create permanent damages to classical solid mirrors are used).

The range of application media for mirror according to the invention includes notably reflective surfaces for the photonic industry, used for example inside equipment for telecommunication applications such as transceivers for data centers. The invention may be also used for larger mirrors used for example in solar electricity production.

FIGURES

FIG. 1 represents the absorption spectra of compounds $5\text{-PF}_6^-$, $11\text{-PF}_6^-$ and $12\text{-PF}_6^-$ in solution in acetonitrile.

FIG. 2 corresponds to a picture of a magenta-colored liquid mirror obtained by dropwise addition of an acetonitrile solution of compound $1\text{-DDQH}^-$, into a stirred saturated aqueous solution of $KPF_6$.

FIG. 3 corresponds to a picture of a magenta-colored mirror of compound $1\text{-PF}_6^-$ that forms on the glass wall of a container, resulting from evaporation of a concentrated acetonitrile solution of chromophoric compound $1\text{-PF}_6^-$.

Figure 7:
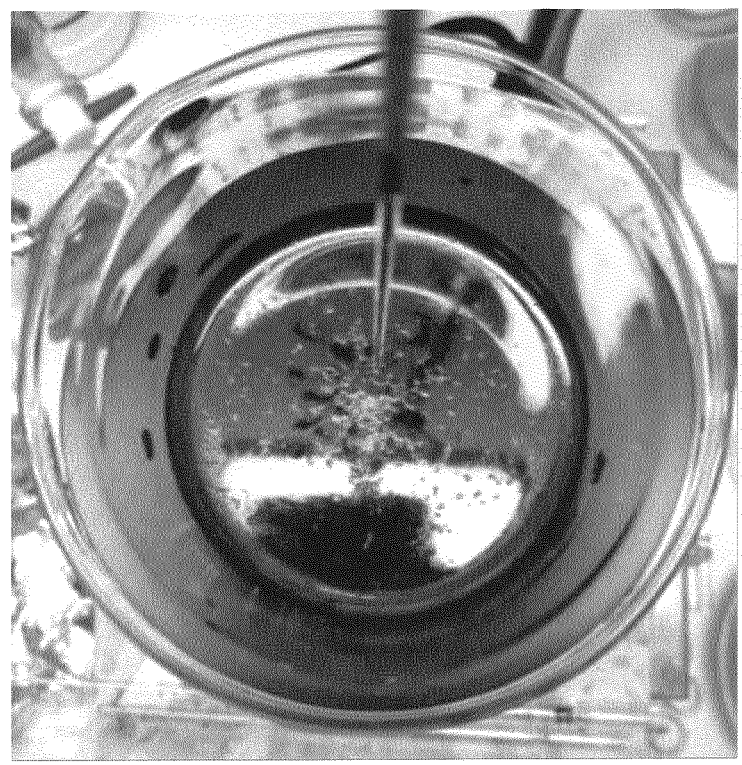

FIG. 7 corresponds to a picture of a gold-like liquid mirror obtained by dropwise addition of an acetonitrile solution of compound $5\text{-DDQH}^-$ into a stirred saturated aqueous solution of $KPF_6$.

Figure 8:
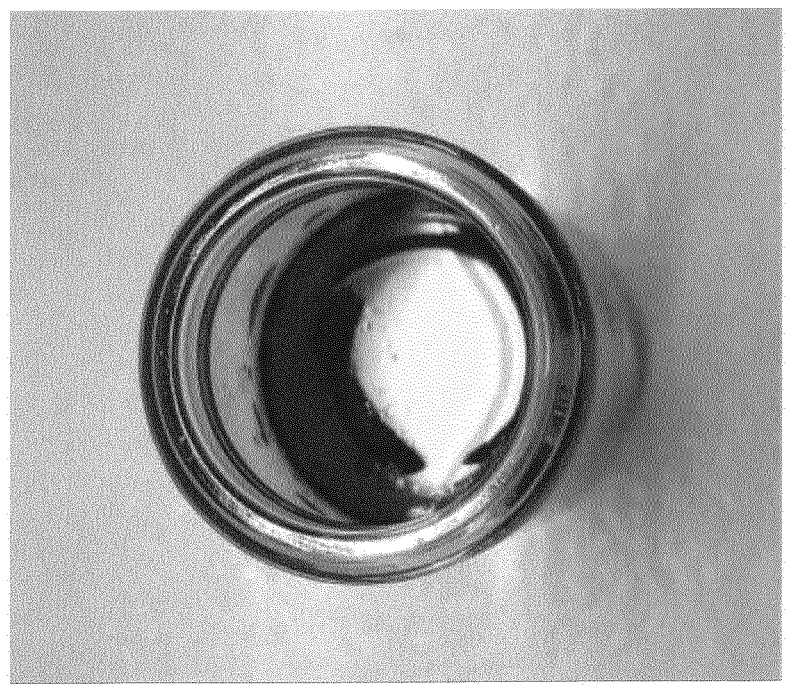

FIG. 8 corresponds to a picture of a self-assembled gold-like liquid mirror observed few minutes after dropwise addition of an acetonitrile solution of compound $5\text{-PF}_6^-$ onto the surface of a saturated aqueous solution of NaCl.

Figure 9:
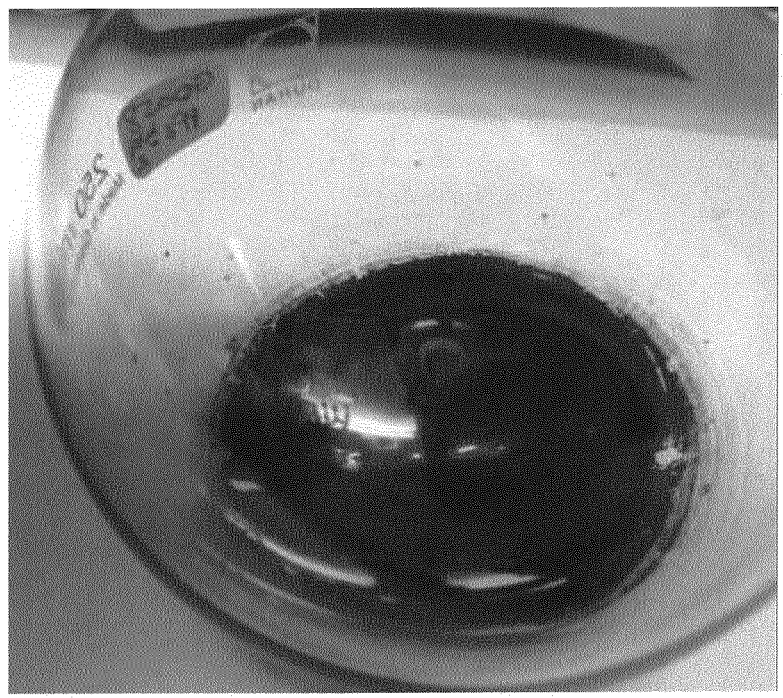

FIG. 9 corresponds to a picture of a copper/gold-like mirror of compound $5\text{-PF}_6^-$ that forms on the wall of a round-bottom flask, resulting from the evaporation under reduced pressure of a concentrated acetonitrile solution of chromophoric compound $5\text{-PF}_6^-$.

Figure 10:
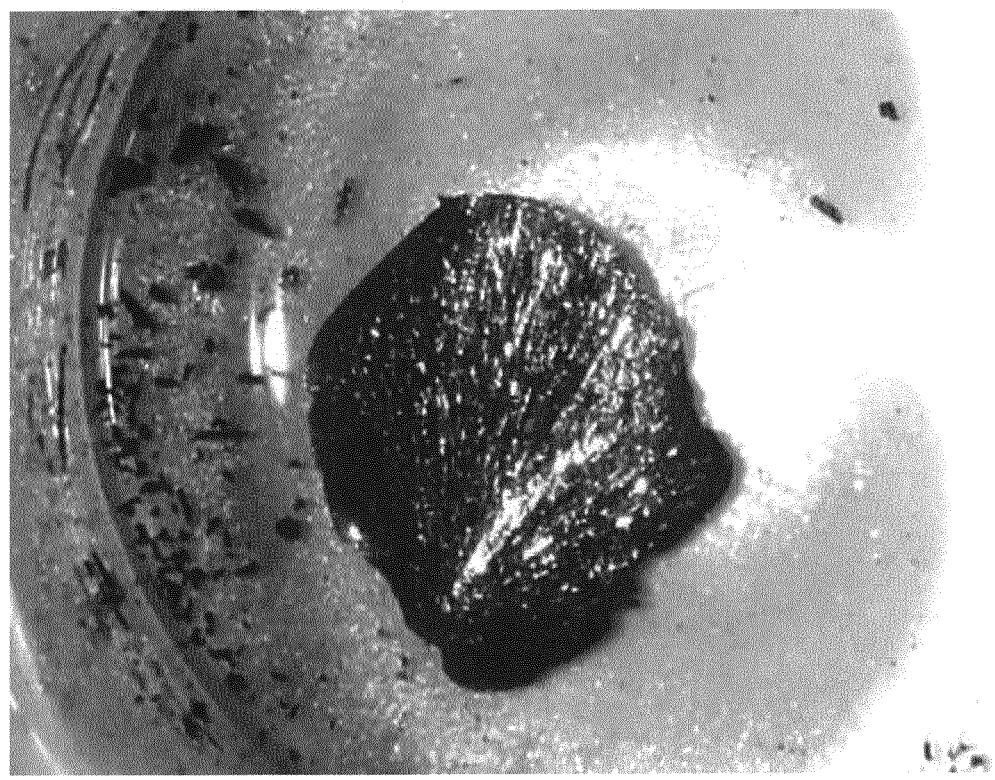

FIG. 10 represents a macroscopic view of compound $5\text{-PF}_6^-$ in its polycrystalline form, characterized by its green metallic luster appearance.

Figure 11:
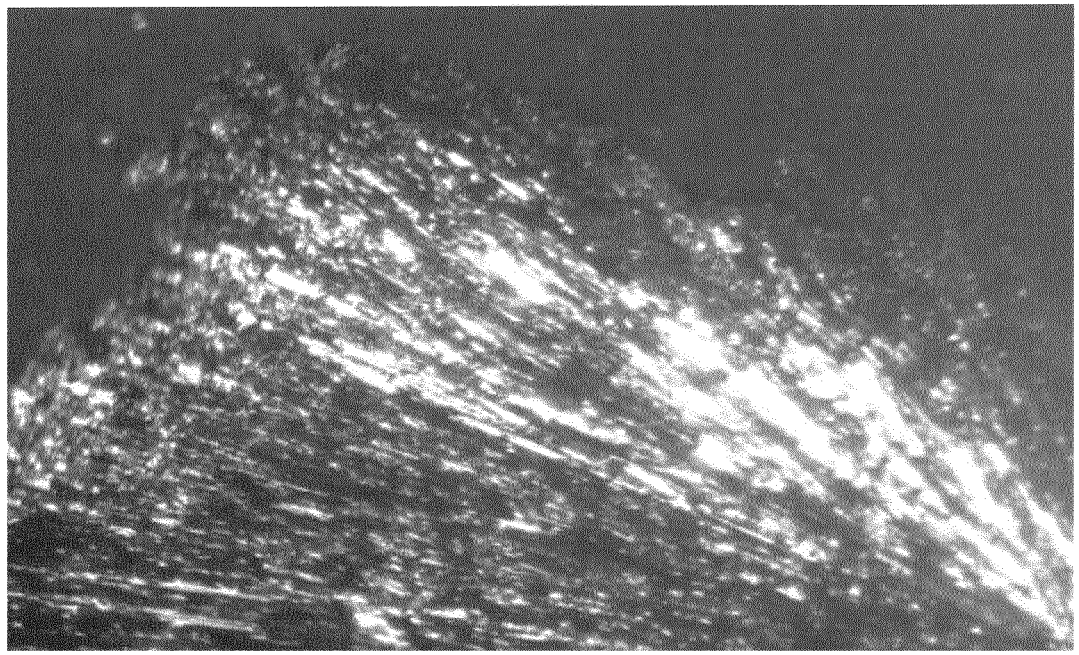

FIG. 11 represents a microscopic view of compound $5\text{-PF}_6^-$ in its polycristalline form, obtained with a Zeiss-Stemi 2000-C microscope.

Figure 12:
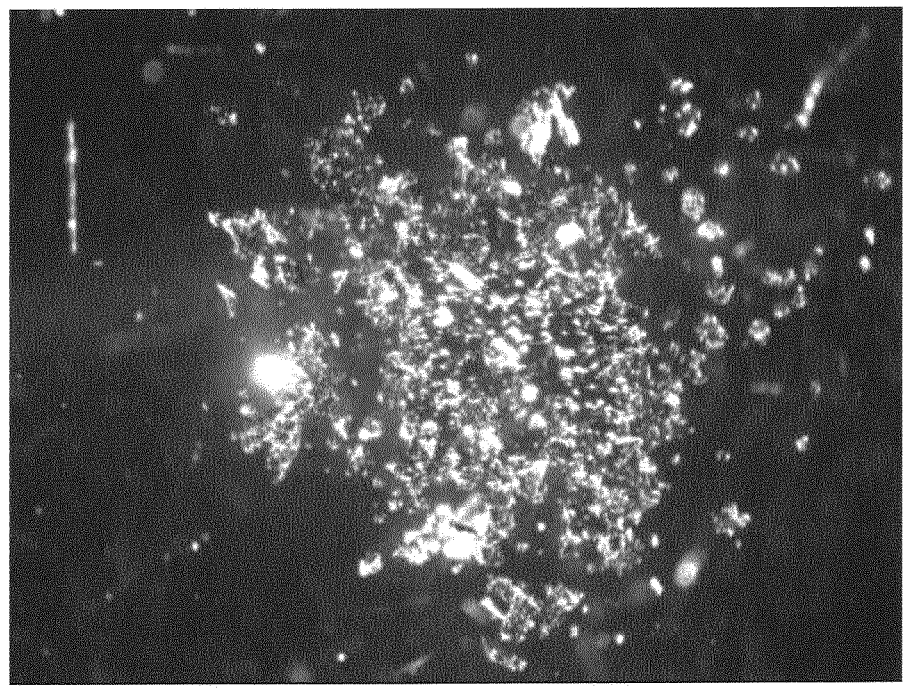

FIG. 12 displays a microscopic view of compound $11\text{-PF}_6^-$ in its microcrystallized form, characterized by its dual metallic (copper/gold & bronze/green) appearance, obtained with a Zeiss-Stemi 2000-C microscope.

Figure 13:
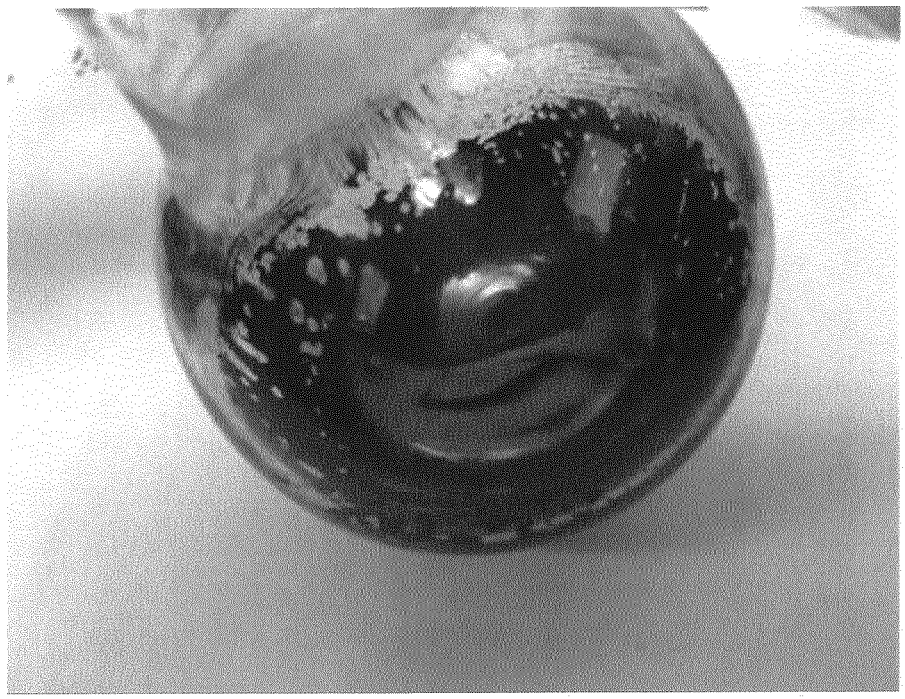

FIG. 13 corresponds to a picture of a copper/gold-like mirror of compound $11\text{-PF}_6^-$ that forms on the inner-wall of a round-bottom flask, resulting from the evaporation under reduced pressure of a concentrated acetonitrile solution of chromophoric compound $11\text{-PF}_6^-$.

Figure 14:
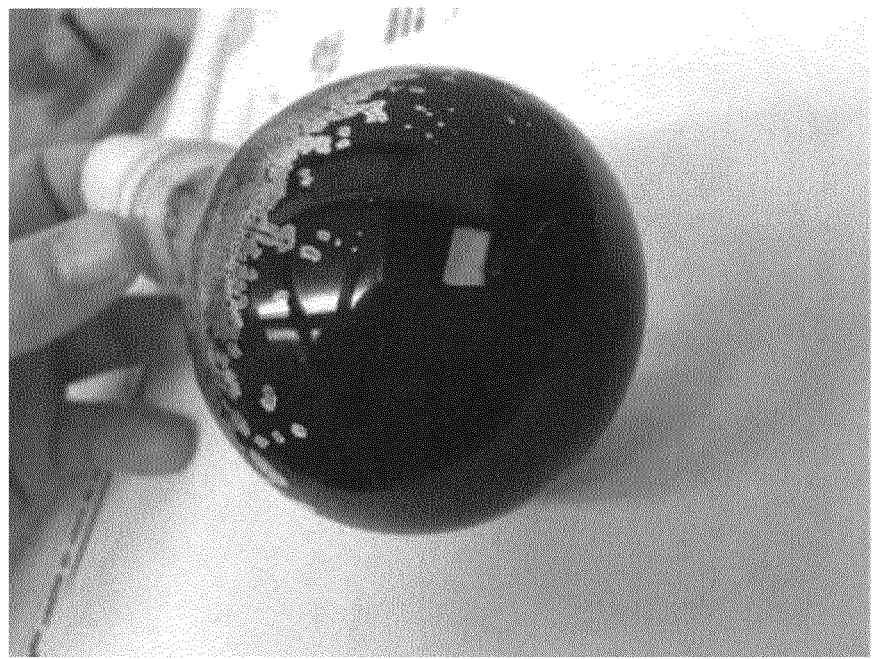

FIG. 14 corresponds to a picture of the outside view of a bronze-like mirror of compound $11\text{-PF}_6^-$ that forms on the inner-wall of a round-bottom flask, resulting from the evaporation under reduced pressure of a concentrated acetonitrile solution of chromophoric compound $11\text{-PF}_6^-$.

Figure 15:
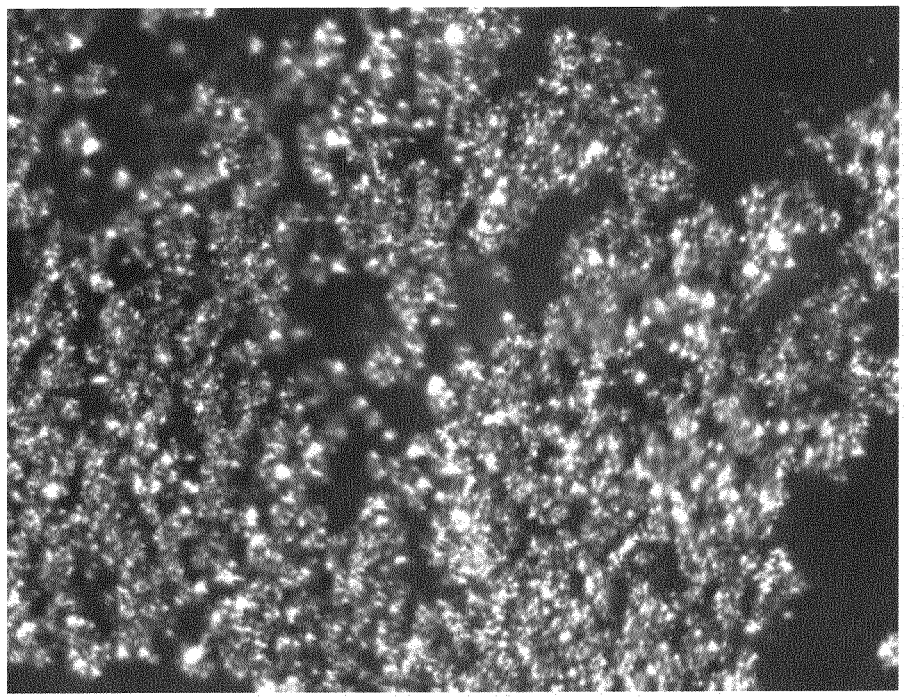

FIG. 15 displays a microscopic view of compound $11\text{-DDQH}^-$ in its microcrystallized form, characterized by its greenish gold luster appearance, obtained with a Zeiss-Stemi 2000-C microscope.

Figure 16:

FIG. 16 displays a macroscopic view of compound $12\text{-PF}_6^-$ in its solid form, characterized by its dual magenta/copper luster appearance.

Figure 17:
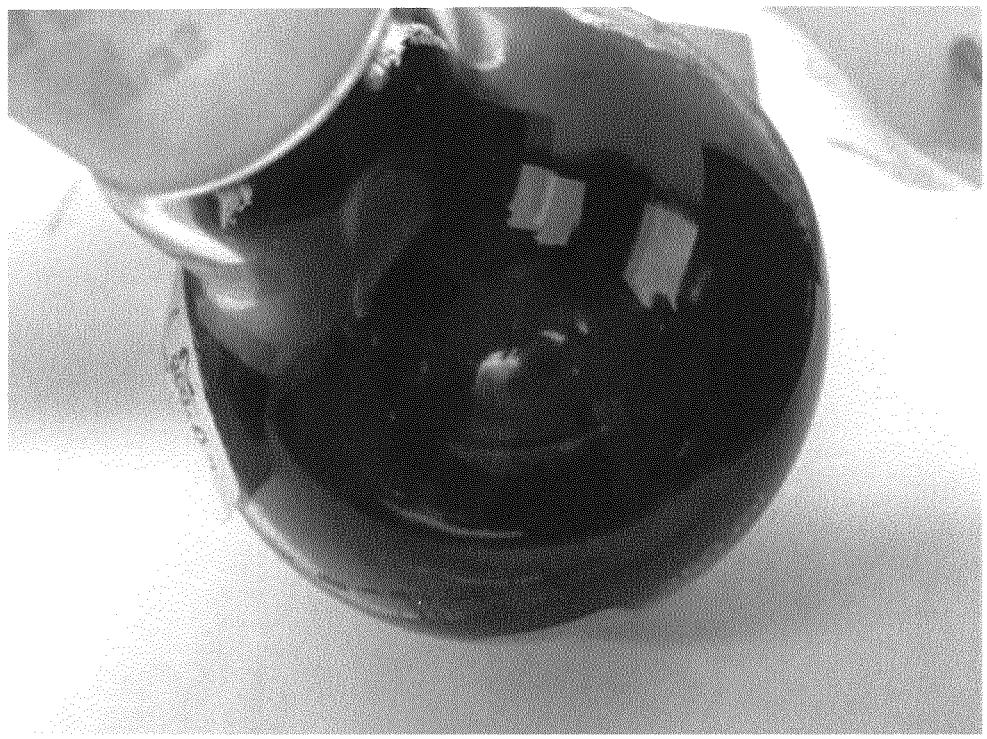

FIG. 17 corresponds to a picture of a magenta-like mirror of compound $12\text{-PF}_6^-$ that forms on the inner-wall of a round-bottom flask, resulting from the evaporation under reduced pressure of a concentrated acetonitrile solution of chromophoric compound $12\text{-PF}_6^-$.

Figure 18:
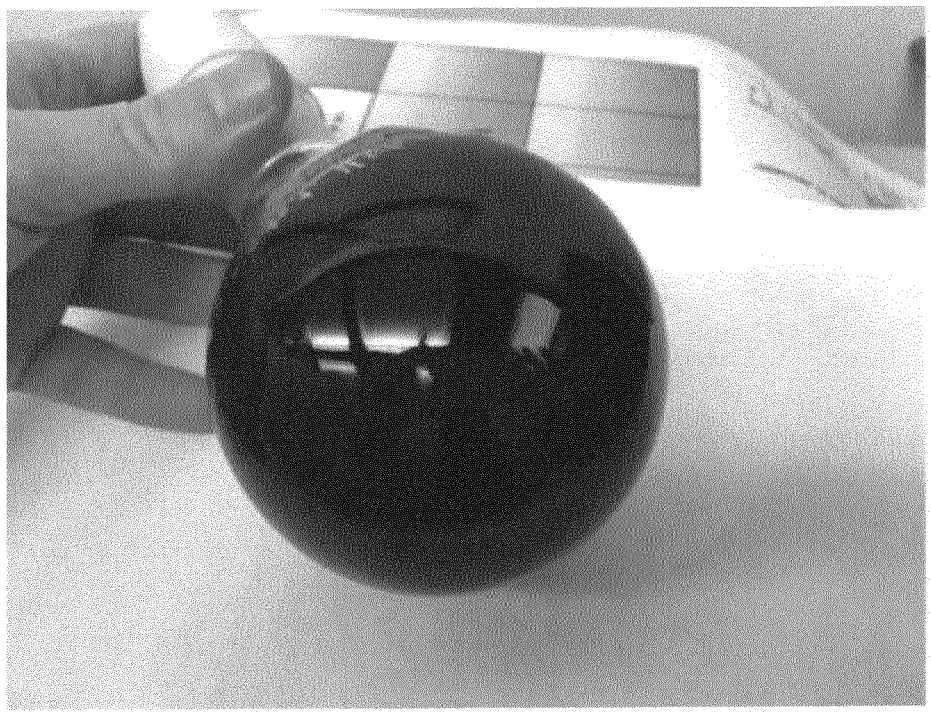

FIG. 18 corresponds to a picture of the outside view of a copper-like mirror of compound 12-$PF_6^-$ that forms on the inner-wall of a round-bottom flask, resulting from the evaporation under reduced pressure of a concentrated acetonitrile solution of chromophoric compound 12-$PF_6^-$.

Figure 19:

FIG. 19 corresponds to a picture of a purple liquid mirror obtained by dropwise addition of an acetonitrile solution of compound 33-$DDQH^-$, into a stirred saturated aqueous solution of $KPF_6$.

Figure 20:

FIG. 20 represents a macroscopic view of compound 34-$DDQH^-$ in form of a metallic pink lacquer.

Figure 21:
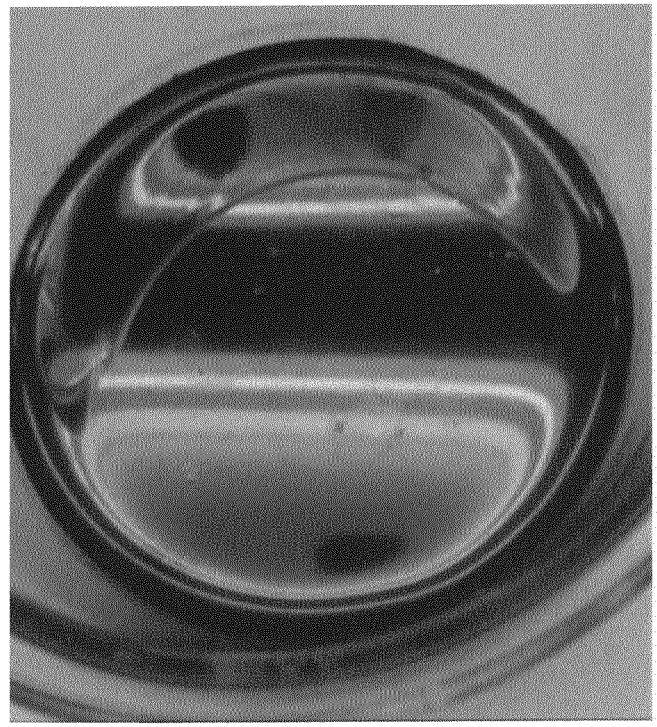

FIG. 21 corresponds to a picture of a magenta/pink-colored liquid mirror obtained by dropwise addition of an acetonitrile solution of compound 34-$DDQH^-$, into a stirred saturated aqueous solution of $KPF_6$.

Figure 22:
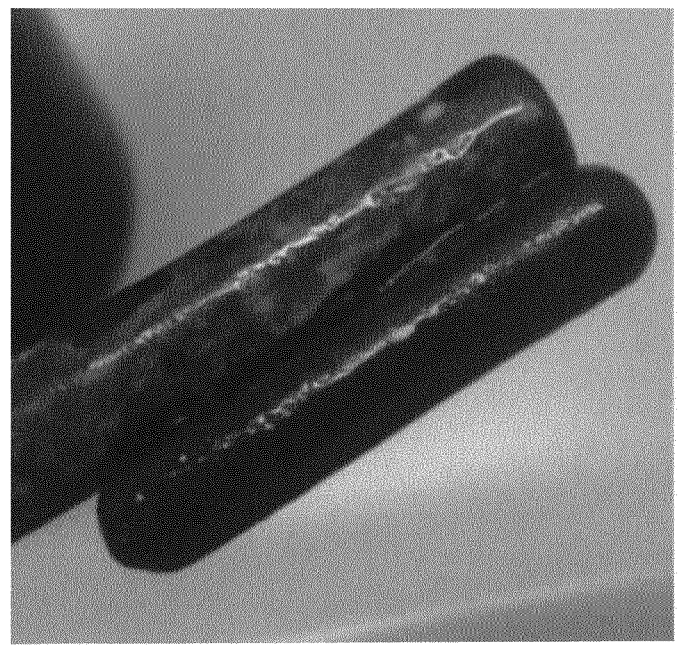

FIG. 22 represents a photograph of a magenta/pink reflective film covering a PTFE magnetic stir bar and its retriever after dipping into the solution displaying at the air-liquid interface the liquid mirror illustrated in FIG. 21.

Figure 23:
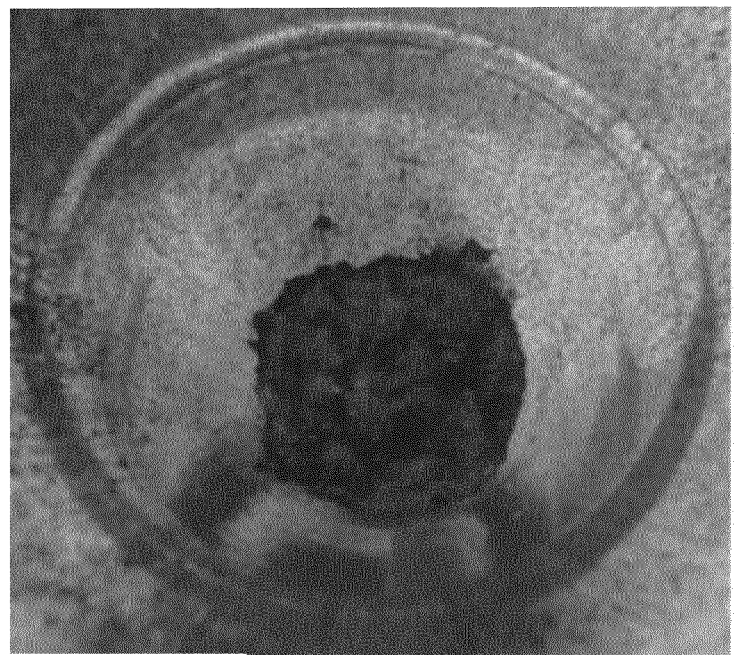

FIG. 23 represents a macroscopic view of compound 34-$PF_6^-$ in its solid form, characterized by its reddish copper flakes appearance.

Figure 24:
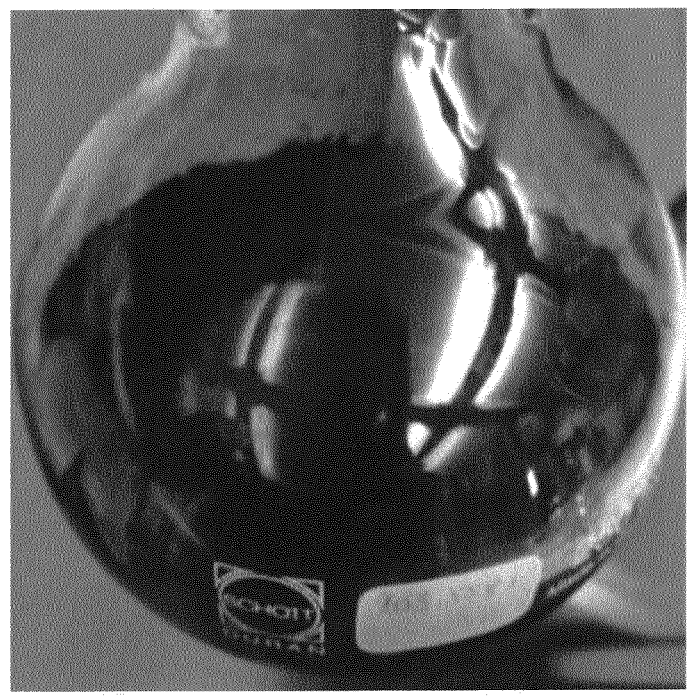

FIG. 24 corresponds to a picture of a magenta/blue-like mirror of compound 34-$PF_6^-$ that forms on the inner-wall of a round-bottom flask, resulting from the evaporation under reduced pressure of a concentrated acetonitrile solution of chromophore compound 34-$PF_6^-$.

Figure 25:

FIG. 25 corresponds to a picture of the outside view of a copper-like mirror of compound 34-$PF_6^-$ that forms on the inner-wall of a round-bottom flask, resulting from the evaporation under reduced pressure of a concentrated acetonitrile solution of chromophoric compound 34-$PF_6^-$.

Figure 26:

FIG. 26 corresponds to a picture of a reflective layer of compound 35-$PF_6^-$ that forms on the inner-wall of a round-bottom flask, resulting from the evaporation under reduced pressure of a concentrated dichloromethane solution of chromophore compound 35-$PF_6^-$.

The examples that follow illustrate the invention without limiting its scope in any way.

EXAMPLES

The following abbreviations have been used:
Ac: Acetyl ($COCH_3$)
All: Allyl
Bn: Benzyl ($CH_2Ph$)
Bu: Butyl ($CH_2CH_2CH_2CH_3$)
ca.: circa
DDQ: 2,3-Dichloro-5,6-dicyano-1,4-benzoquinone
DCM: Dichloromethane
DMF: Dimethylformamide
equiv.: equivalent
ESI: Electrospray ionisation
Et: Ethyl ($CH_2CH_3$)
LAH: Lithium aluminium hydride
Me: Methyl ($CH_3$)
MS: Mass Spectroscopy
NBS: N-Bromosuccinimide
NIR: Near Infra Red
NMR: Nuclear Magnetic Resonance
Ph: Phenyl ($C_6H_5$)
PPA: Polyphosphoric acid
PTFE: Polytetrafluoroethylene
$Tf_2O$: Triflic anhydride
THF: Tetrahydrofuran
TMSI: Trimethylsilyl iodide
vis: visible
wt: weight I—Synthesis of the Compounds According to the Invention I-1. General Procedures General Procedure A:

Compounds of the formula A (para-amino ortho-substituted diphenylcarbenium) can be prepared by the following Reaction Scheme 1:

Reaction Scheme 1

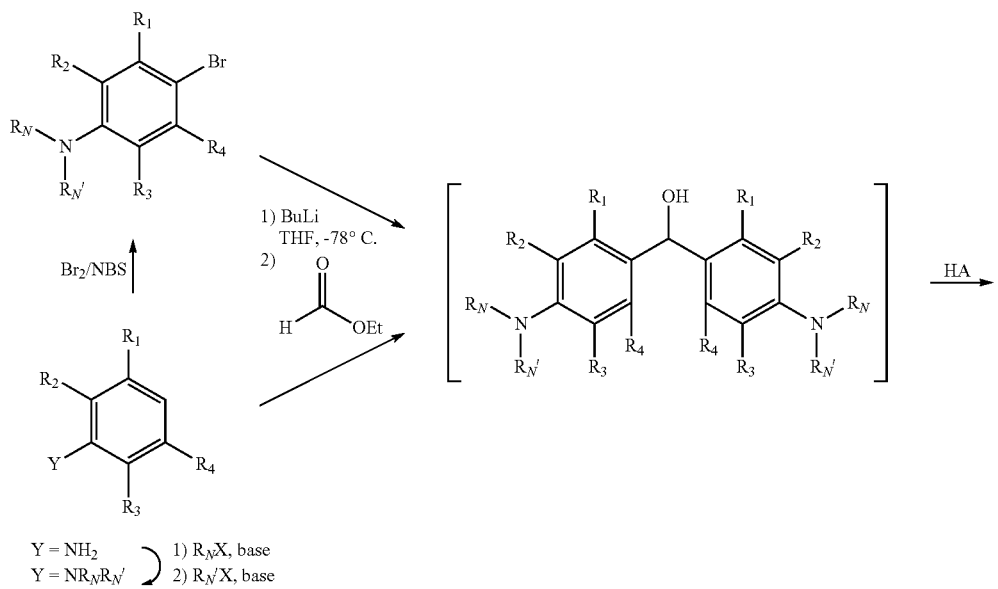

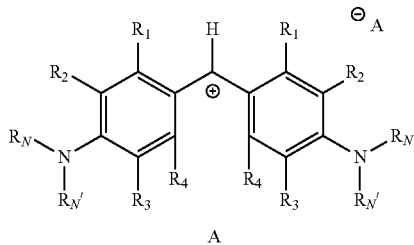

A

A meta-disubstituted N,N-disubstituted aniline precursor (either commercially available or not) is engaged in a lithiation reaction. Depending on the nature of the starting material, a prior step of para bromination may be necessary, employing either $Br_2$ or NBS as reactive species [Zysman2009]. The lithiated intermediate is quenched with ethyl formate yielding a carbinol intermediate [Patents], itself easily dehydrated to produce the desired carbenium when reacted with acidic species (HA), the nature of which determines the identity of carbenium counteranion ($A^-$). The latter can be changed afterward by anion metathesis.

General Procedure Abis:

Compounds of the formula A (para-amino ortho-substituted diphenylcarbenium) can also be prepared by the following Reaction Scheme 2 as a one pot reaction (Scheme 2 a)) or as a two-step reaction (Scheme 2b)):

Reaction Scheme 2

2a)

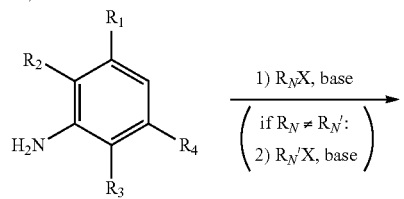

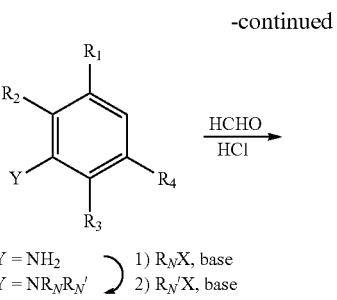

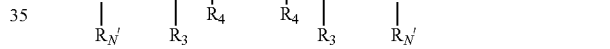

2b)

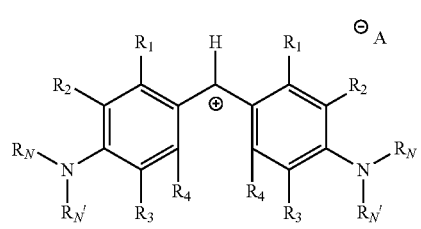

A

A meta-disubstituted N,N-disubstituted aniline precursor (either commercially available or not) is engaged in a formaldehyde-mediated dimerization reaction [Takahashi2002]. The resulting methylene, that often easily crystallizes is then oxidized with DDQ (or another suitable oxidant, which is here more particularly a hydride abstraction reagent) to directly produce the desired carbenium. A final step of metathesis may optionally be required to obtain the desired counteranion ($A^-$).

General Procedure B:

Compounds of the formula B ((polyalkoxyphenyl)-para-amino ortho-substituted diphenylcarbenium) can be prepared by the following Reaction Scheme 3:

Reaction Scheme 3

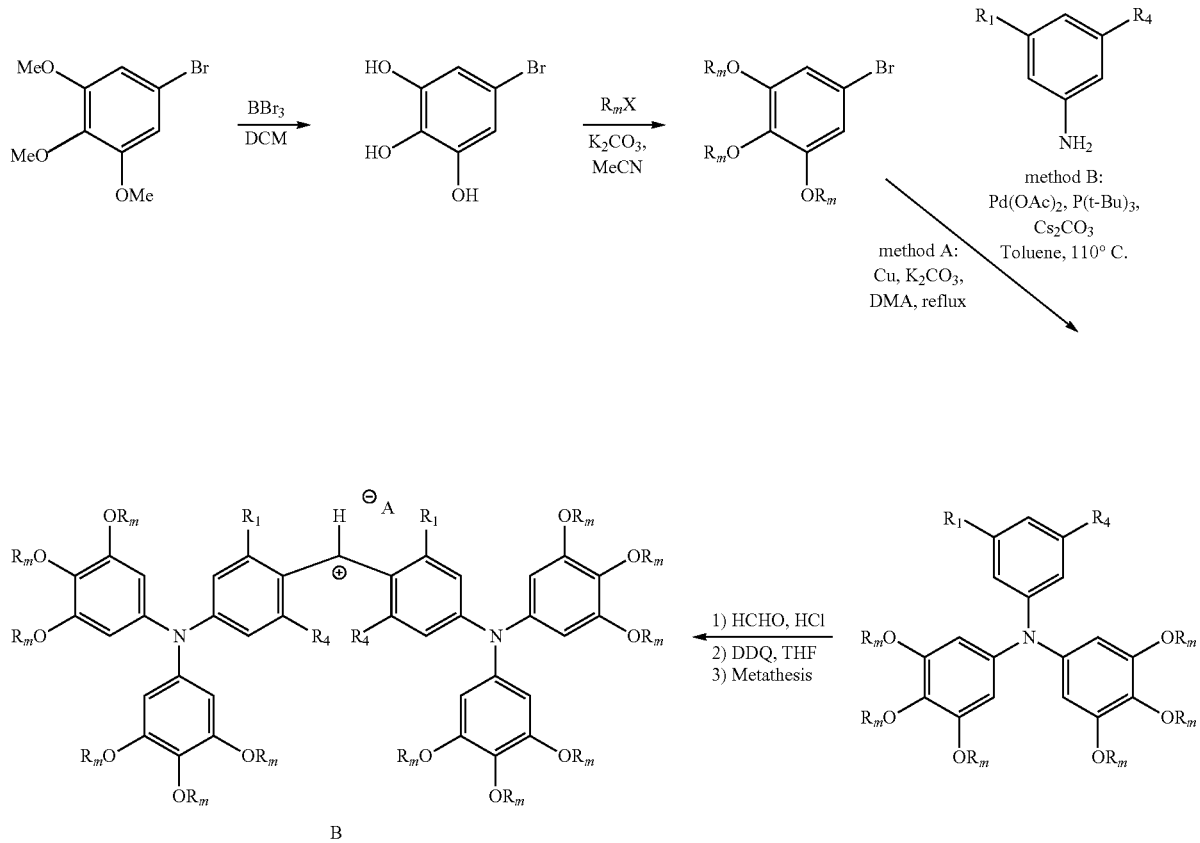

Commercially available 5-bromo-1,2,3-trimethoxybenzene is engaged in a demethylation reaction mediated by $BBr_3$ to give 5-bromo-1,2,3-triol. This trihydroxybenzene is then engaged in a Williamson etherification with alkyl halides of desired length. Resulting bromotrialkoxybenzene is coupled with an adequately substituted aniline either under Ullmann [Velasco2009] or Buchwald-Hartwig [Rajan2012] conditions. This precursor can then be engaged in a formaldehyde-mediated dimerization reaction [Takahashi2002]. The resulting methylene is then oxidized with DDQ (or another suitable oxidant, which is here more particularly a hydride abstraction reagent) to directly produce the desired carbenium. A final step of metathesis may optionally be required to obtain the desired counteranion ($A^-$).

General Procedure Bbis:

Compounds of the formula B ((polyalkoxyphenyl)-para-amino ortho-substituted diphenylcarbenium) can also be prepared by the following Reaction Scheme 3bis:

Reaction Scheme 3bis

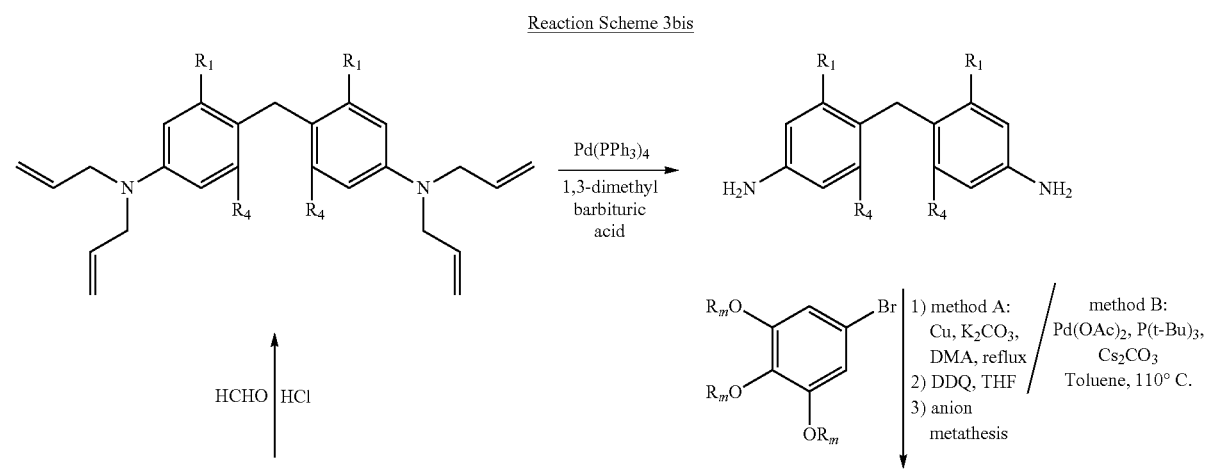

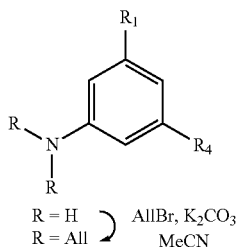

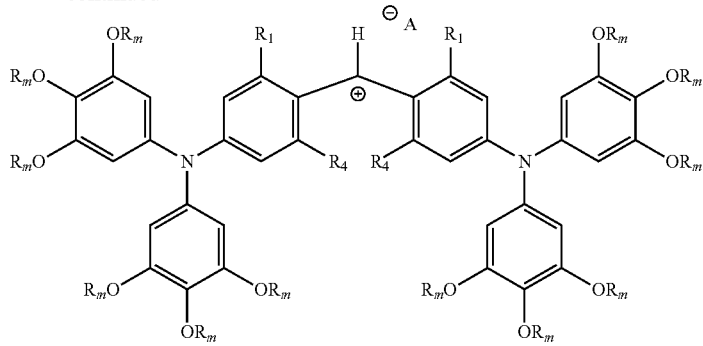

B

A meta-disubstituted aniline (either commercially available or not) is engaged in a diallylation step [Egawa2011]. This protected aniline can then be engaged in a formaldehyde-mediated dimerization reaction [Takahashi2002], before deprotection of the allyl groups (e.g. by using a palladium catalyst in presence of 1,3-dimethylbarbituric acid) [Egawa2011]. The resulting diaminophenyl methylene is then coupled with a bromotrialkoxybenzene compound either under Ullmann [Velasco2009] or Buchwald-Hartwig [Rajan2012] conditions. The resulting methylene is then oxidized with DDQ (or another suitable oxidant, which is here more particularly a hydride abstraction reagent) to directly produce the desired carbenium. A final step of metathesis may optionally be required to obtain the desired counteranion (A⁻).

General Procedure C:

Compounds of the formula C ((polyalkoxybenzyl)-para-amino ortho-substituted diphenylcarbenium) can also be prepared by the following Reaction Scheme 4:

Commercially available methyl gallate is engaged in a Williamson etherification with alkyl halides of desired length. Resulting trialkoxyphenylester is reduced (e.g. with lithium aluminium hydride) into the corresponding benzylic alcohol. This latter is then chlorinated in presence of $SOCl_2$ [Balagurusamy1997], before its coupling, under basic conditions, with an adequately substituted aniline. This precursor can then be engaged in a formaldehyde-mediated dimerization reaction [Takahashi2002]. The resulting methylene is then oxidized with DDQ (or another suitable oxidant, which is here more particularly a hydride abstraction reagent) to directly produce the desired carbenium. A final step of metathesis may optionally be required to obtain the desired counteranion (A⁻).

General Procedure Cbis:

Compounds of the formula C ((polyalkoxybenzyl)-para-amino ortho-substituted diphenylcarbenium) can be prepared by the following Reaction Scheme 4bis:

Reaction Scheme 4

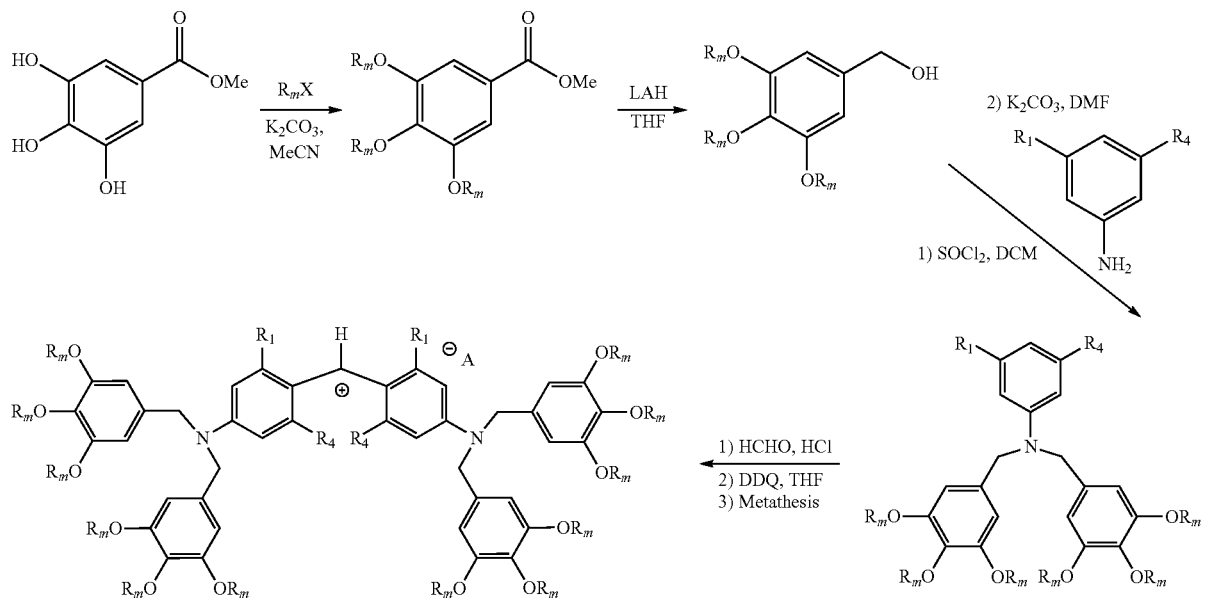

C

Reaction Scheme 4bis

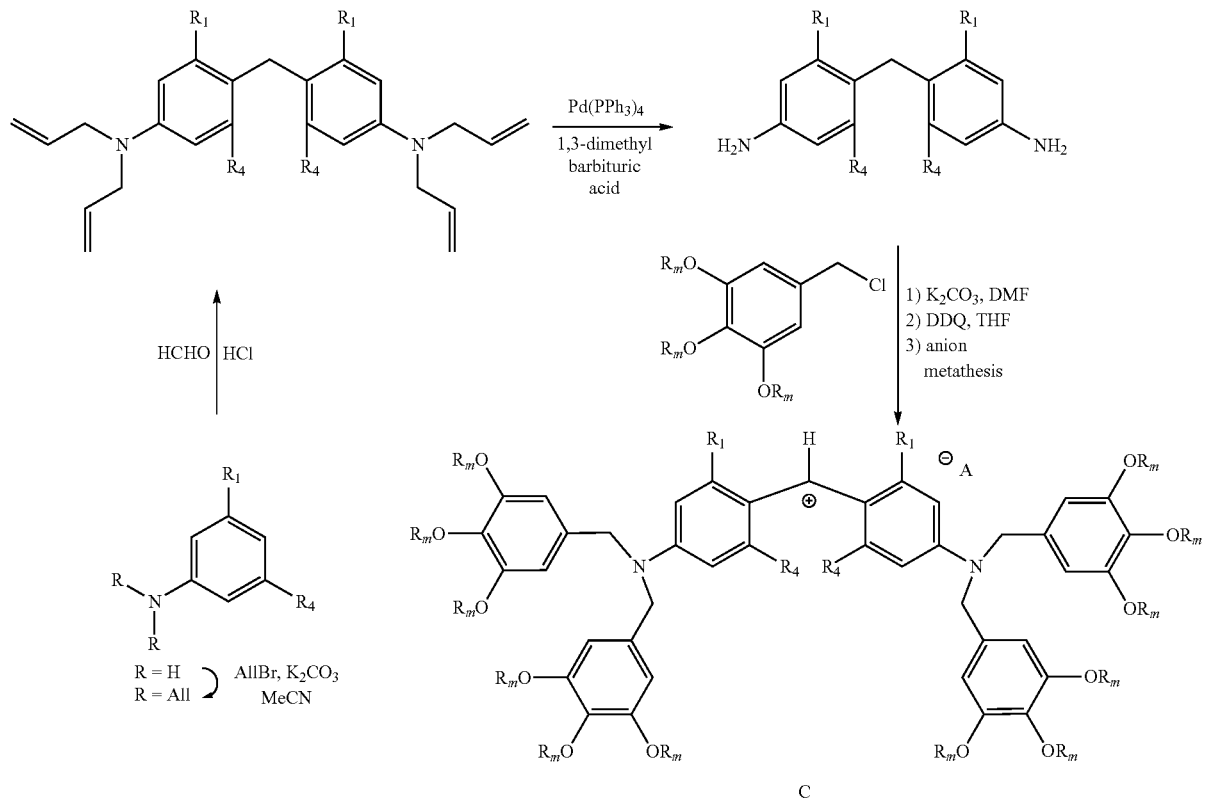

A meta-disubstituted aniline (either commercially available or not) is engaged in a diallylation step [Egawa2011]. This protected aniline can then be engaged in a formaldehyde-mediated dimerization reaction [Takahashi2002], before deprotection of the allyl groups (e.g. by using a palladium catalyst in presence of 1,3-dimethylbarbituric acid) [Egawa2011]. The resulting diaminophenyl methylene is then coupled with a trialkoxybenzyl chloride compound under basic conditions. The resulting methylene is then oxidized with DDQ (or another suitable oxidant, which is here more particularly a hydride abstraction reagent) to directly produce the desired carbenium. A final step of metathesis may optionally be required to obtain the desired counteranion (A⁻).

General Procedure D:

Compounds of the formula D can be obtained from the key benzophenone (KB) precursor prepared by the following Reaction Scheme 5:

Reaction Scheme 5

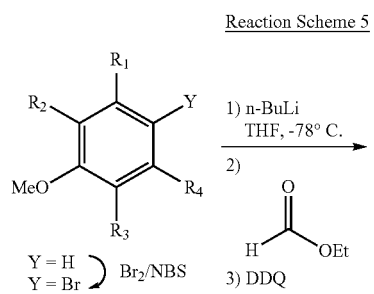

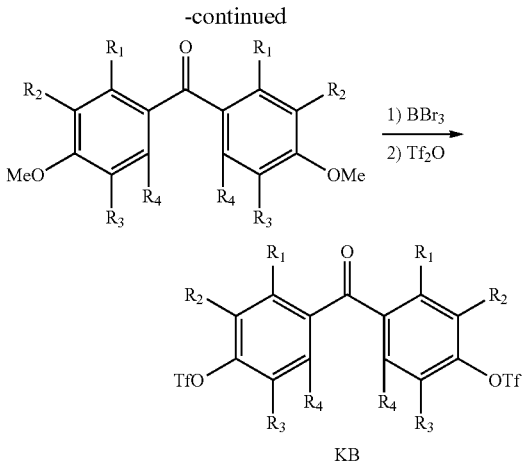

A meta-disubstituted anisole (either commercially available or not) is para-brominated according to a classical procedure employing either $Br_2$ or NBS as reactive species [Zysman2009]. The resulting bromoanisole is then engaged in a lithiation reaction, and the intermediate is quenched with ethyl formate yielding a carbinol intermediate, [Patents] which is subsequently oxidized to the corresponding ketone by using DDQ [Torricelli2013]. The methoxy groups of this benzophenone are demethylated by using $BBr_3$ and the resulting phenol moieties are then reacted with triflic anhydride to give the desired key benzophenone derivatives, KB.

Compounds of the formula D (para-(aryl-extended amino) ortho-substituted diphenylcarbenium) can then be prepared by the following Reaction Scheme 6:

Reaction Scheme 6

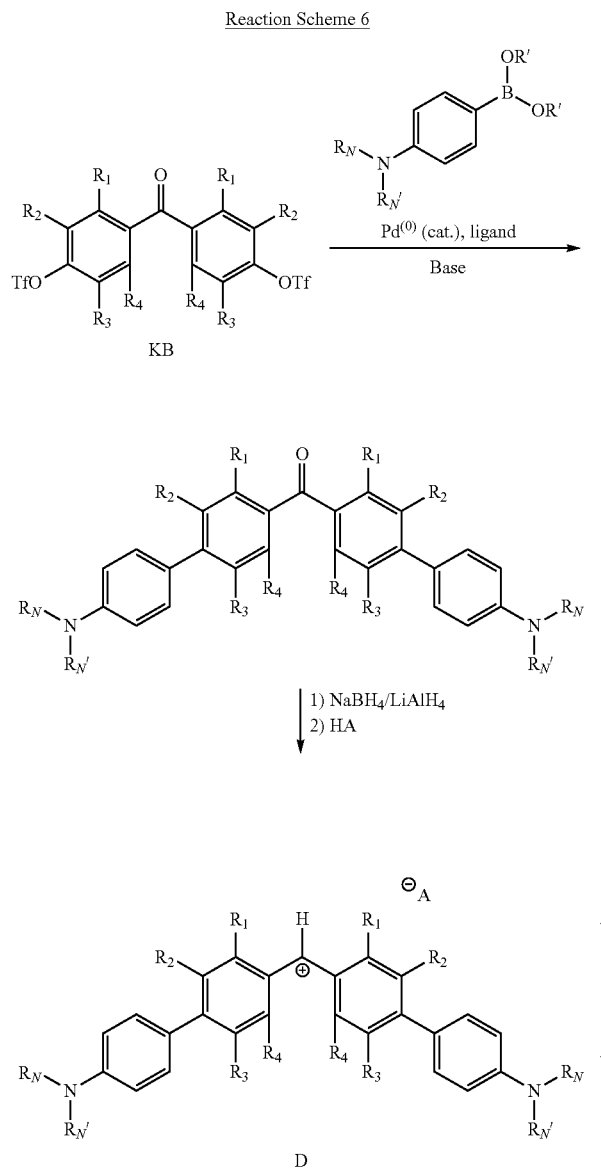

Reaction Scheme 7

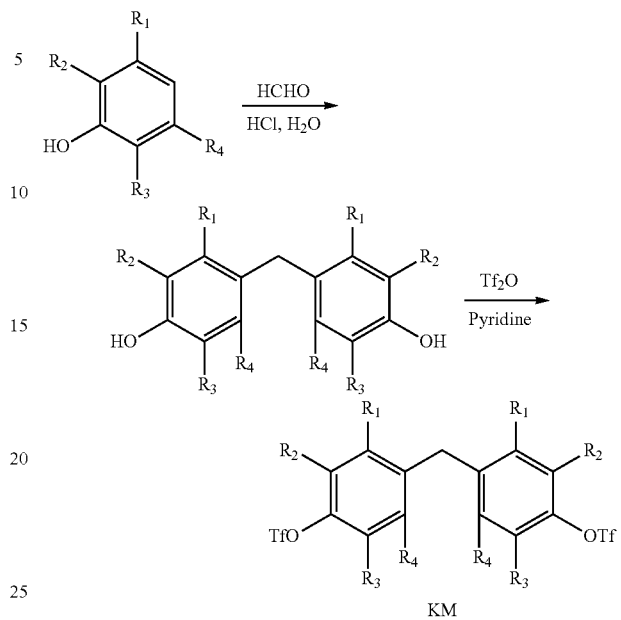

A meta-disubstituted phenol (either commercially available or not) is dimerized at its para position, in the presence of formaldehyde either under basic or under acidic conditions (notably HCl, $H_2SO_4$ or AcOH), to give a diphenolmethane. Both hydroxy groups of the resulting compound are then triflated with triflic anhydride in the presence of pyridine to give the desired key methylene derivatives, KM.

Compounds of the formula D (para-(aryl-extended amino) ortho-substituted diphenylcarbenium) can be prepared from KM precursors by the following Reaction Scheme 6bis:

Reaction Scheme 6bis

The previously described key benzophenone KB precursors may be engaged in a double Suzuki cross-coupling by reacting with a para-aminophenylboronic acid/ester (either commercially available or not) in presence of a base and a palladium catalyst. The resulting extended benzophenone can then be reduced (by either $NaBH_4$ or $LiAlH_4$) yielding the corresponding carbinol intermediate that can be itself easily dehydrated to produce the desired carbenium when reacted with acidic species (HA), the nature of which determines the identity of carbenium counteranion ($A^-$). The latter can be changed afterward by anion metathesis.

General Procedure Dbis:

Compounds of the formula D can also be obtained from the key methylene (KM) precursors prepared by the following Reaction Scheme 7:

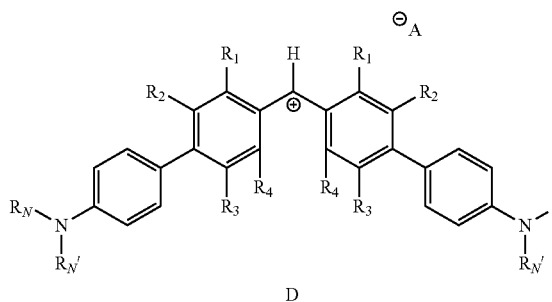

D

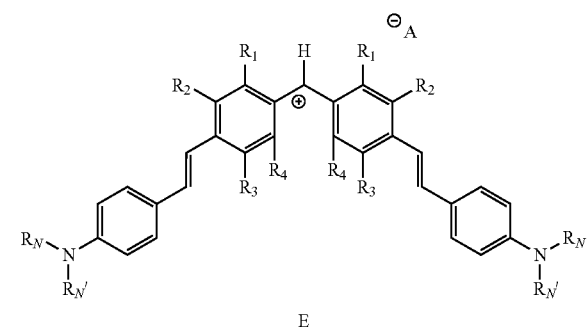

E

The previously described key methylene KM precursors may be engaged in a double Suzuki cross-coupling by reacting with a para-aminophenylboronic acid/ester (either commercially available or not) in the presence of a base and a palladium catalyst. The resulting extended methylene can then be oxidized with DDQ (or another suitable oxidant, which is here more particularly a hydride abstraction reagent) to directly produce the desired carbenium. A final step of metathesis may optionally be required to obtain the desired counteranion ($A^-$).

General Procedure E:

Compounds of the formula E can be obtained from the key benzophenone (KB) precursors prepared by the previously detailed Reaction Scheme 5.

Compounds of the formula E (para-(styryl-extended amino) ortho-substituted diphenylcarbenium) can be prepared by the following Reaction Scheme 8:

The key benzophenone KB precursors may be engaged in a double Heck coupling by reacting with a para-aminostyryl precursor (either commercially available or not) in presence of a base and a palladium catalyst. The resulting extended benzophenone can then be reduced (by either $NaBH_4$ or $LiAlH_4$) yielding the corresponding carbinol intermediate that can be itself easily dehydrated to produce the desired carbenium when reacted with acidic species (HA), the nature of which determines the identity of carbenium counteranion ($A^-$). The latter can be changed afterward by anion metathesis.

General Procedure Ebis:

Compounds of the formula E can also be obtained from the key methylene (KM) precursors prepared by the previously detailed Reaction Scheme 7.

Compounds of the formula E (para-(styryl-extended amino) ortho-substituted diphenylcarbenium) can then be prepared by the following Reaction Scheme 8bis:

Reaction Scheme 8

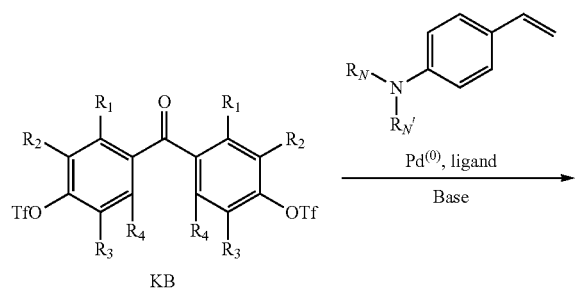

Reaction Scheme 8bis

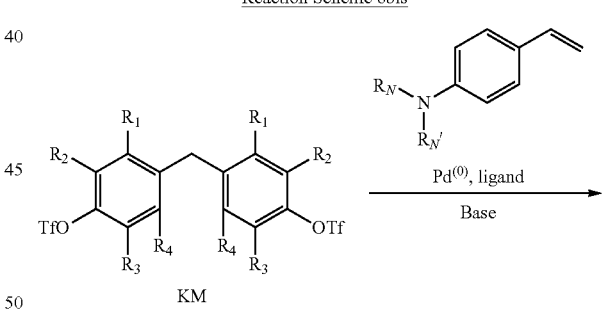

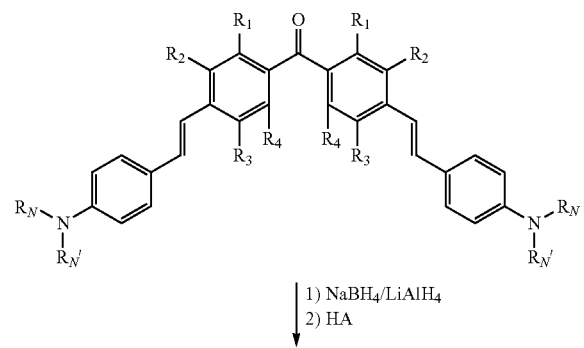

1) $NaBH_4/LiAlH_4$
2) HA

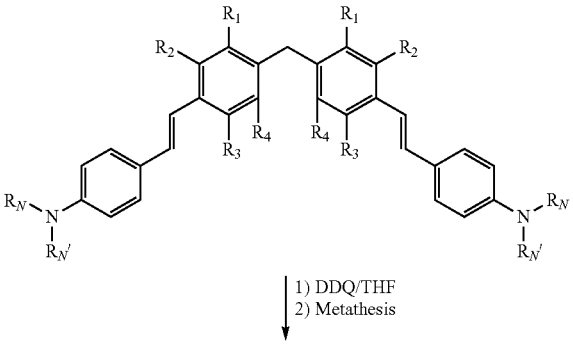

1) DDQ/THF
2) Metathesis

-continued

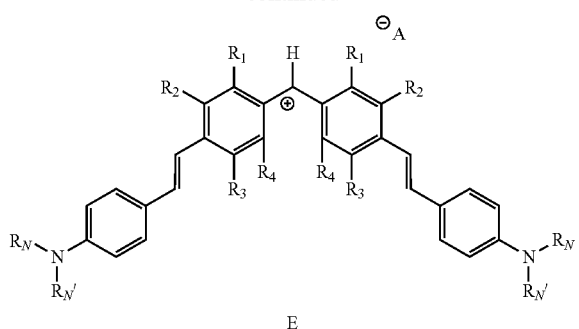

E

The key methylene KM may be engaged in a double Heck coupling by reacting with a para-aminostyryl precursor (either commercially available or not) in the presence of a base and a palladium catalyst. The resulting extended methylene can then be oxidized with DDQ (or another suitable oxidant, which is here more particularly a hydride abstraction reagent) to directly produce the desired carbenium. A final step of metathesis may optionally be required to obtain the desired counteranion ($A^-$).

General Procedure F:

Compounds of the formula F can be obtained from the key benzophenone (KB) precursors prepared by the previously detailed Reaction Scheme 5.

Compounds of the formula F (para-(phenylethynyl-extended amino) ortho-substituted diphenylcarbenium) can be prepared by the following Reaction Scheme 9:

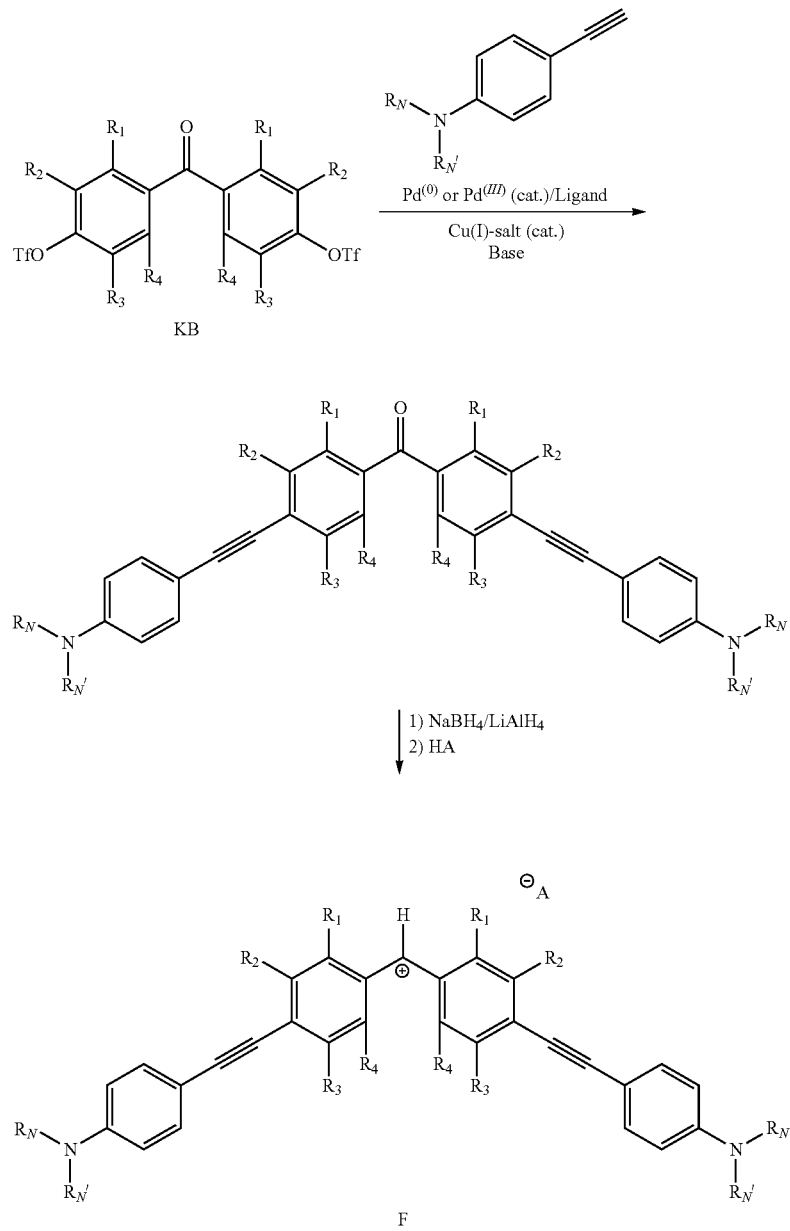

The key benzophenone KB precursors may be engaged in a double Sonogashira cross-coupling by reacting with a para-aminophenethynyl precursor (either commercially available or not) in presence of a base, Cu(I)-salt and a palladium catalyst. The resulting extended benzophenone can then be reduced (by either NaBH$_4$ or LiAH$_4$) yielding the corresponding carbinol intermediate that can be itself easily dehydrated to produce the desired carbenium when reacted with acidic species (HA), the nature of which determines the identity of carbenium counteranion (A$^-$). The latter can be changed afterward by anion metathesis.

General Procedure Fbis:

Compounds of the formula F can also be obtained from the key methylene (KM) precursors prepared by the previously detailed Reaction Scheme 7.

Compounds of the formula F (para-(phenylethynyl-extended amino) ortho-substituted diphenylcarbenium) can be prepared by the following Reaction Scheme 9bis:

The key methylene KM may be engaged in a double Sonogashira cross-coupling by reacting with a para-aminophenethynyl precursor (either commercially available or not) in presence of a base, Cu(I)-salt and a palladium catalyst. The resulting extended methylene can then be oxidized with DDQ (or another suitable oxidant, which is here more particularly a hydride abstraction reagent) to directly produce the desired carbenium. A final step of metathesis may optionally be required to obtain the desired counteranion (A$^-$).

General Procedure G:

Compounds of the formula G (hindered ipso-aryl para-amino ortho-substituted diphenylcarbenium) can be prepared by the following Reaction Scheme 10:

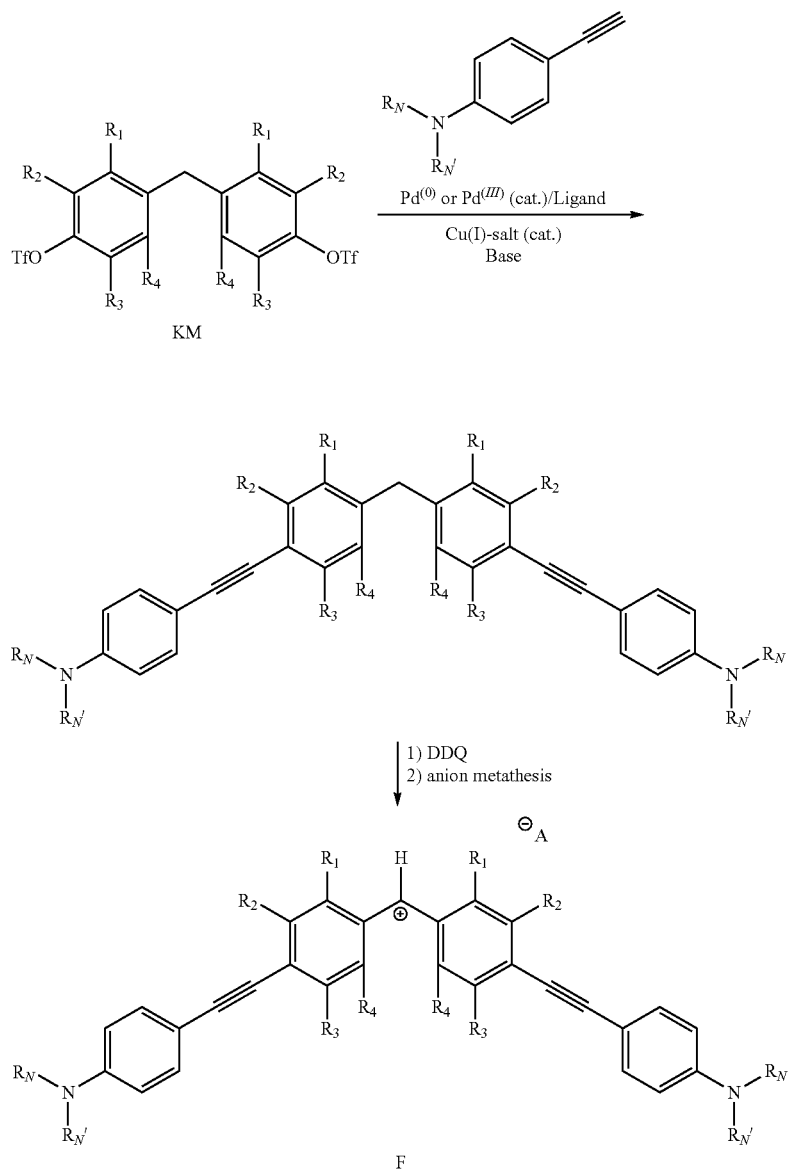

Reaction Scheme 9bis

Reaction Scheme 10

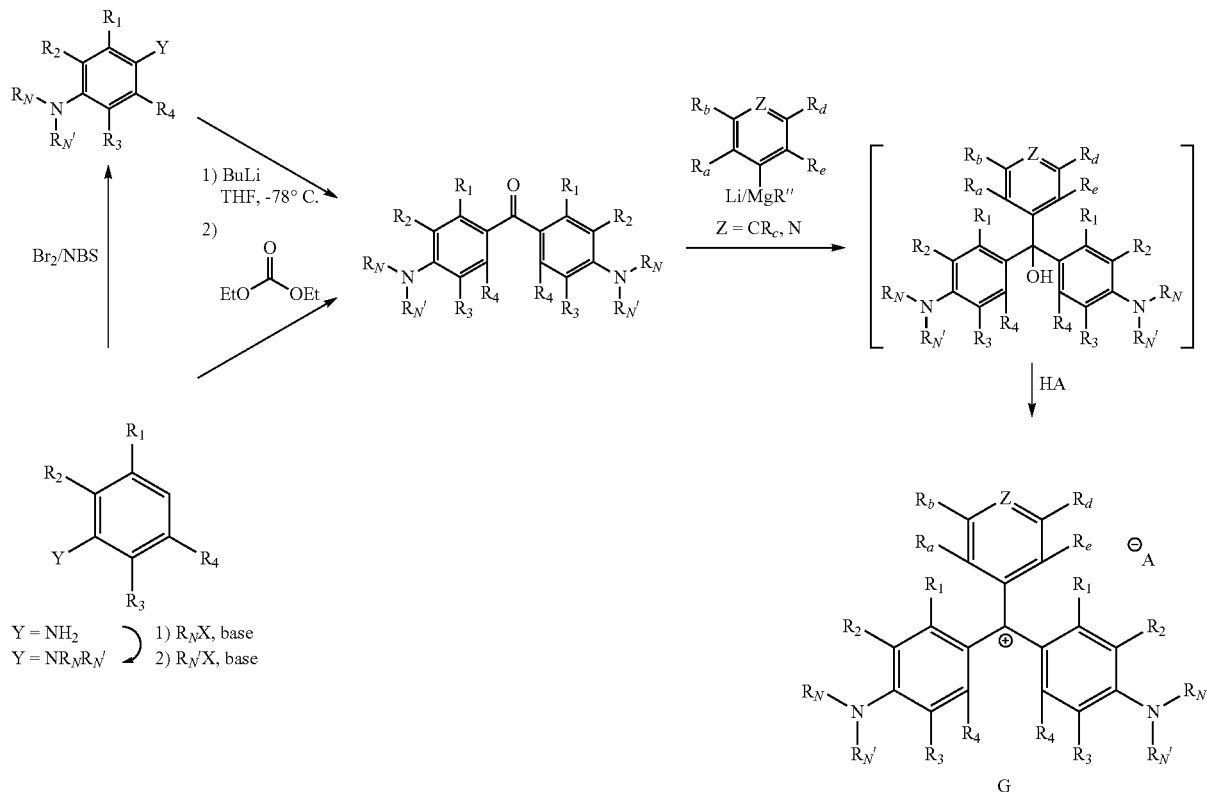

A meta-disubstituted N,N-disubstituted aniline precursor (either commercially available or not) is engaged in a lithiation reaction. Depending on the nature of the starting material, a prior step of para bromination may be necessary, employing either $Br_2$ or NBS as reactive species [Zysman2009]. The lithiated intermediate is quenched with diethyl carbonate yielding a benzophenone which is further engaged in presence of a hindered organolithium/Grignard reactant [Wu2008]. The tertiary alcohol intermediate thus obtained is itself easily dehydrated to produce the desired carbenium when reacted with acidic species (HA), the nature of which determines the identity of carbenium counteranion ($A^-$). The latter can be changed afterward by anion metathesis.

General Procedure Gbis:

Compounds of the formula G (hindered ipso-aryl para-amino ortho-substituted diphenylcarbenium) can alternatively be prepared by the following Reaction Scheme 10bis:

Reaction Scheme 10bis

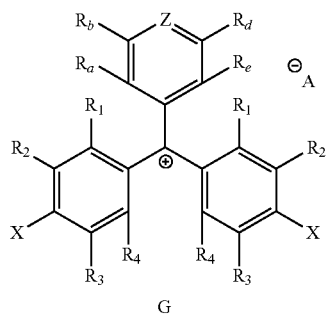

A meta-disubstituted N,N-disubstituted aniline precursor (either commercially available or not) is engaged in a lithiation reaction. Depending on the nature of the starting material, a prior step of para bromination may be necessary, employing either $Br_2$ or NBS as reactive species [Zysman2009]. The lithiated intermediate is further engaged in presence of a conveniently substituted aryl ester. The tertiary alcohol intermediate thus obtained is itself easily dehydrated to produce the desired carbenium when reacted with acidic species (HA), the nature of which determines the identity of carbenium counteranion ($A^-$). The latter can be changed afterward by anion metathesis.

General Procedure H:

Compounds of the formula H ($SiR_2$-bridged para-amino ortho-substituted diphenylcarbenium) can be prepared by the following Reaction Scheme 11:

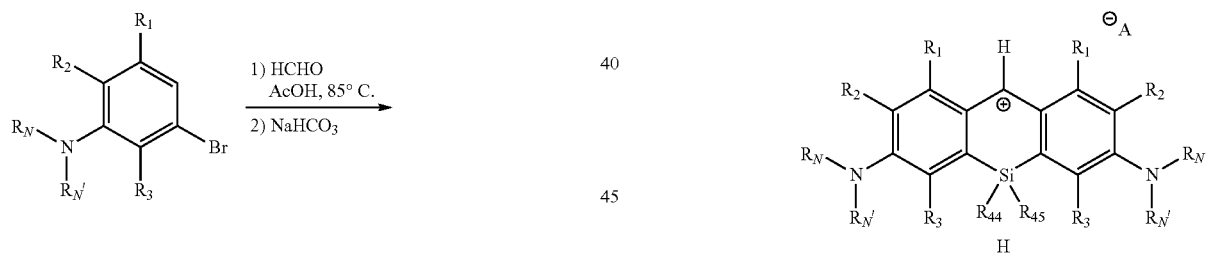

A meta-brominated meta-substituted aniline precursor (either commercially available or not) is engaged in a formaldehyde-mediated dimerization reaction to give the corresponding dibromo diarylmethane [Koide2011]. The bromine atoms are then exchanged in presence of BuLi in order to produce the corresponding dilithium intermediate which is quenched by addition of a disubstituted silicon dichloride reagent [Koide2011]. The resulting bridged diarylmethane is then oxidized with DDQ or p-chloranil (or another suitable oxidant, which is here more particularly a hydride abstraction reagent) to directly produce the desired carbenium. A final step of metathesis is required to obtain the desired counteranion ($A^-$).

General Procedure I:

Compounds of the formula I ($CMe_2$-bridged para-amino ortho-substituted diphenylcarbenium) can be prepared by the following Reaction Scheme 12:

Reaction Scheme 12

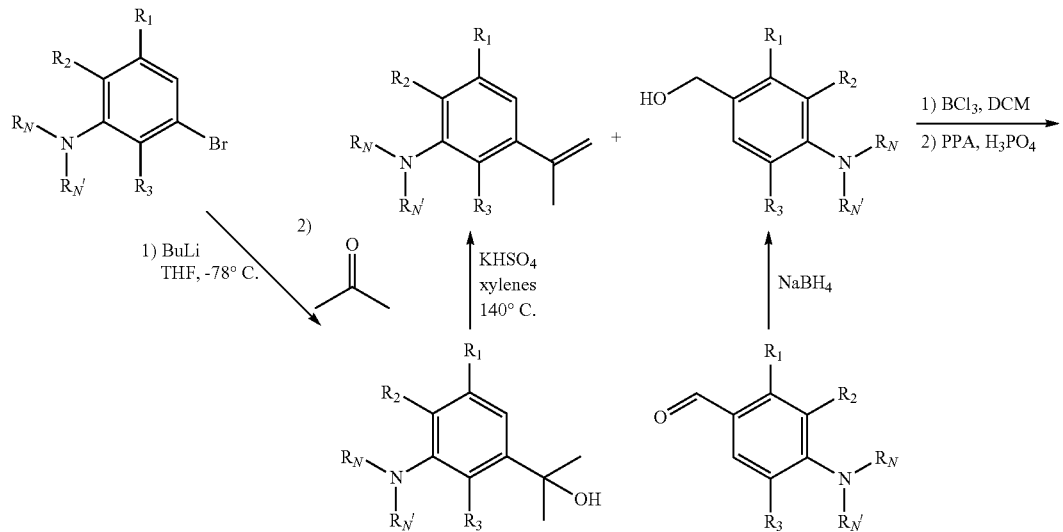

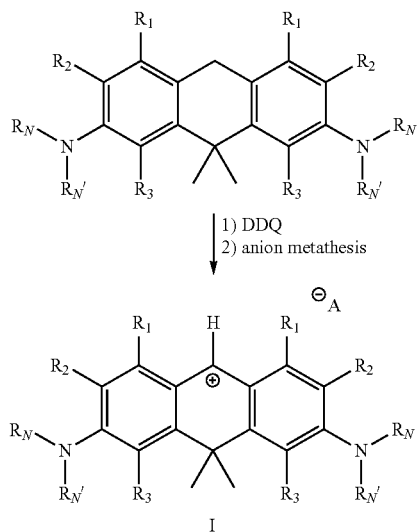

A meta-bromo N,N-disubstituted aniline precursor (either commercially available or not) is engaged in a halogen-metal exchange reaction to produce the corresponding lithiated intermediate which is quenched by addition of dry acetone. The resulting tertiary alcohol is then dehydrated by heating in presence of $KHSO_4$ to give a methylene exo compound. The latter molecule is engaged with a closely related counterpart (but bearing a benzylic alcohol moiety) in a sequence of reactions allowing coupling and bridging of these two parts [Pastierik2014]. The resulting bridged diarylmethane is then oxidized with DDQ or p-chloranil (or another suitable oxidant, which is here more particularly a hydride abstraction reagent) to directly produce the desired carbenium. A final step of metathesis is required to obtain the desired counteranion ($A^-$).

General Procedure J:

Compounds of the formula J (three and more atoms-bridged para-amino ortho-substituted diphenylcarbenium) can be prepared by the following Reaction Scheme 13:

Reaction Scheme 13

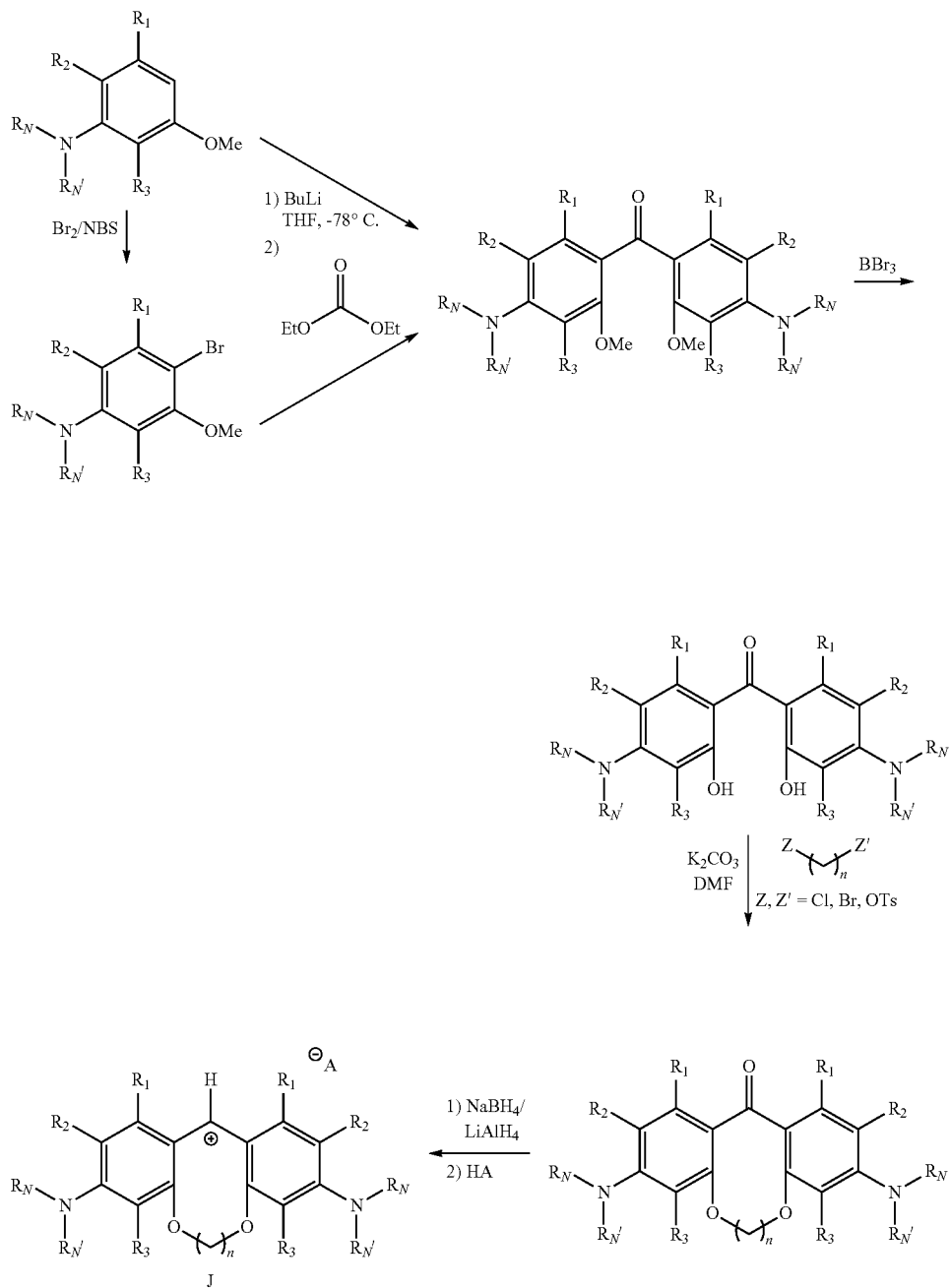

A meta-methoxylated N,N-disubstituted aniline precursor meta-substituted electrodonating precursor (either commercially available or not) is engaged in a lithiation reaction. Depending on the nature of the starting material, a prior step of para bromination may be necessary, employing either $Br_2$ or NBS as reactive species [Zysman2009]. The lithiated intermediate is quenched with diethyl carbonate yielding a dimethoxy benzophenone, which methoxy groups are subsequently demethylated by using $BBr_3$. The resulting phenol moieties are then bridged together through an aliphatic chain of length controlled by the nature of the reagent employed (e.g.: $CH_2BrCl$ for n=1, TsO—$(CH_2)_2$-OTs for n=2) [Sorrell1997]. The resulting bridged benzophenone can then be reduced (by either $NaBH_4$ or $LiAlH_4$) yielding the corresponding carbinol intermediate that can be itself easily dehydrated to produce the desired carbenium when reacted with acidic species (HA), the nature of which determines the identity of carbenium counteranion ($A^-$). The latter can be changed afterward by anion metathesis.

General Procedure Jbis:

Compounds of the formula J (three and more atoms-bridged para-amino ortho-substituted diphenylcarbenium) can alternatively be prepared by the following Reaction Scheme 13bis:

Reaction Scheme 13bis

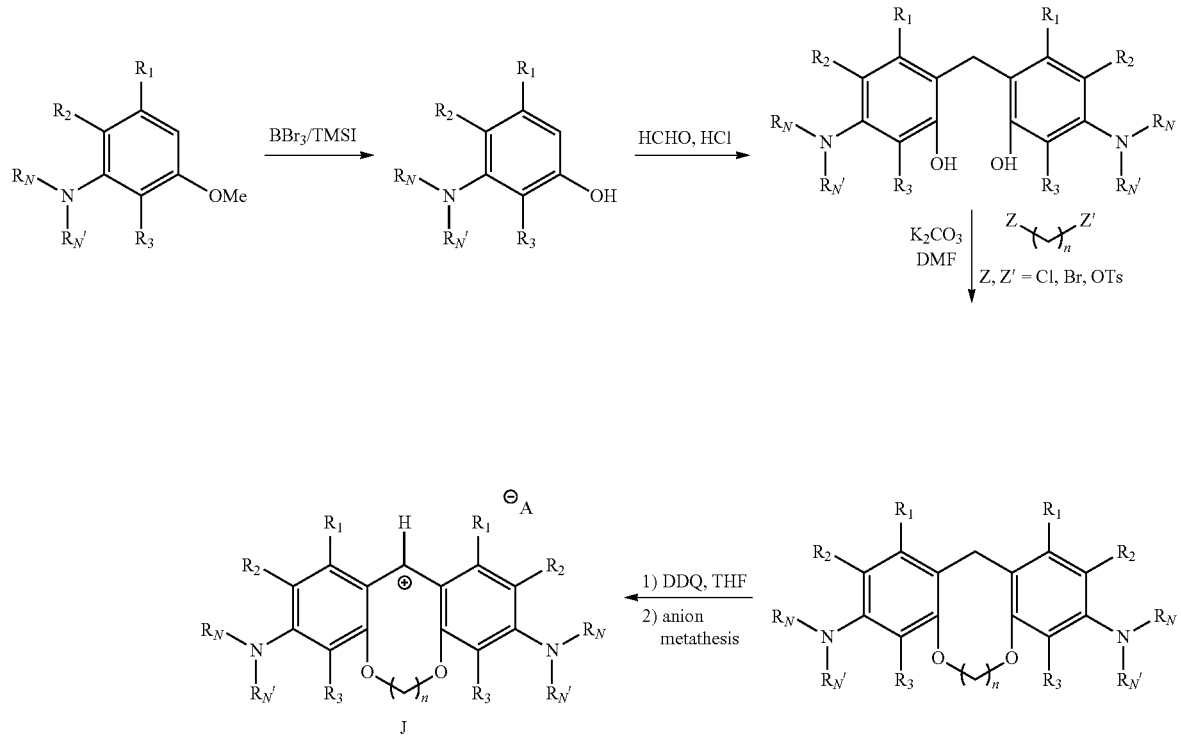

A meta-methoxylated N,N-disubstituted aniline precursor (either commercially available or not) is engaged in the presence of a demethylating agent (e.g. BBr₃ or TMSI) to give the corresponding phenol. The resulting compound is then dimerized at its para position, in the presence of formaldehyde under acidic conditions (notably HCl, H₂SO₄ or AcOH), to give a diphenolmethane. The hydroxyl groups are then bridged together through an aliphatic chain of length controlled by the nature of the reagent employed (e.g.: CH₂BrCl for n=1, TsO—(CH₂)₂-OTs for n=2) [Sorrell1997]. The resulting bridged methylene can then be oxidized with DDQ (or another suitable oxidant, which is here more particularly a hydride abstraction reagent) to directly produce the desired carbenium. A final step of metathesis may optionally be required to obtain the desired counteranion (A⁻).

General Procedure K:

Compounds of the formula K (hindered ipso-alkyl para-amino ortho-substituted diphenylcarbenium) can be prepared by the following Reaction Scheme 14:

Reaction Scheme 14

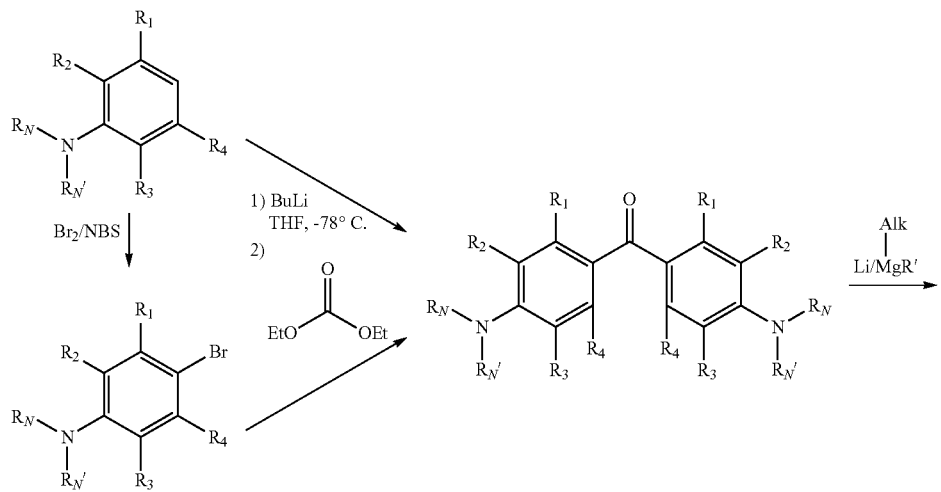

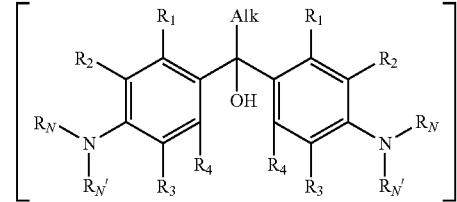

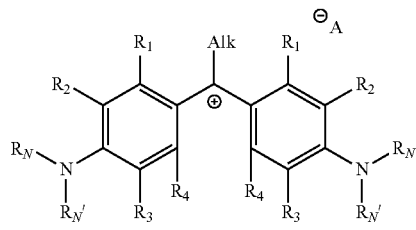

K

A meta-disubstituted N,N-disubstituted aniline precursor (either commercially available or not) is engaged in a lithiation reaction. Depending on the nature of the starting material, a prior step of para bromination may be necessary, employing either $Br_2$ or NBS as reactive species [Zysman2009]. The lithiated intermediate is quenched with diethyl carbonate yielding a benzophenone which is further engaged in presence of an alkyl (either linear, branched or cyclic) organometallics. The tertiary alcohol intermediate thus obtained is itself easily dehydrated to produce the desired carbenium when reacted with acidic species (HA), the nature of which determines the identity of carbenium counteranion ($A^-$). The latter can be changed afterward by anion metathesis.

General Procedure L:

Compounds of the formula L (hindered ipso-cyano para-amino ortho-substituted diphenylcarbenium) can be prepared by the following Reaction Scheme 15:

Reaction Scheme 15

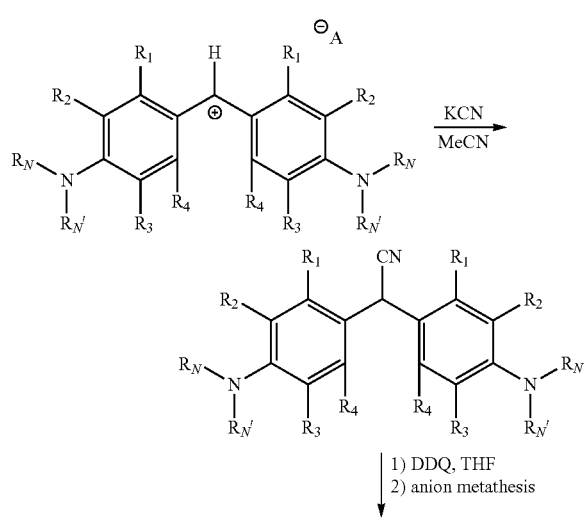

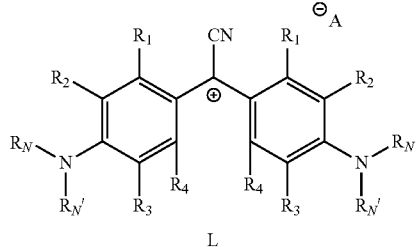

L

A bis(para-aminophenyl)methylium compound is engaged in a cyanation reaction, employing either KCN or another cyanide salt. The resulting neutral cyano compound can then be oxidized with DDQ (or another suitable oxidant, which is here more particularly a hydride abstraction reagent) to directly produce the desired carbenium. A final step of metathesis may optionally be required to obtain the desired counteranion ($A^-$).

REFERENCES CITED IN THE ABOVE DESCRIBED GENERAL PROCEDURES

[Zysman2009]: Zysman-Colman, E., Arias, K., Siegel, J. S. Can. J. Chem., 2009, 87, 440-447. [Patents]: CA 2311064; U.S. Pat. No. 6,670,512

[Takahashi2002]: Takahashi, H., Kashiwa, N., Hashimoto, Y., Nagasawa, K. Tetrahedron Lett. 2002, 43, 2935-2938.

[Velasco2009] Velasco, D., Jankauskas, V., Stumbraite, J., Grazulevicius, J. V., Getautis, V. Synth. Met., 2009, 159, 654-658.

[Rajan2012] Rajan, Y. C., Shellaiah, M., Huang, C.-T., Lin, H.-C., Lin, H.-C. Tetrahedron, 2012, 68, 7926-7931.

[Egawa2011] Egawa, T., Koide, Y., Hanaoka, K., Komatsu, T., Terai, T., Nagano, T. Chem. Commun., 2011, 47, 4162-4164.

[Balagurusamy1997] Balagurusamy, V. S. K., Ungar, G., Percec, V., Johansson, G. J. Am. Chem. Soc., 1997, 119, 1539-1555.

[Torricelli2013]: Torricelli, F., Bosson, J., Besnard, C., Chekini, M., Burgi, T., Lacour, J. Angew. Chem. Int. Ed. 2013, 52, 1796-1800.

[Koide2011]: Koide, Y., Urano, Y., Hanaoka, K., Terai, T., Nagano, T. ACS Chem. Biol. 2011, 6, 600-608.

[Pastierik2014]: Pastierik, T., Sebej, P., Medalovi, J., tacko, P., Klin, P. J. Org. Chem. 2014, 79,3374-3382.

[Sorrell1997]: Sorrell, T. N., Yuan, H. J. Org. Chem. 1997, 62, 1899-1902.

[Best2013] Best, Q. A., Sattenapally, N., Dyer, D. J., Scott, C. N., McCarroll, M. E. J. Am Chem. Soc. 2013, 135, 13365-13370.

[Pastierik2014]: Pastierik, T., Sebej, P., Medalovi, J., tacko, P., Klin, P. J. Org. Chem. 2014, 79,3374-3382.

[Sorrell1997]: Sorrell, T. N., Yuan, H. J. Org. Chem. 1997, 62, 1899-1902.

[Singh2014] Singh, D., Chaudhari, U. V., Deota P. T. Tetrahedron, 2014, 70, 4485-4493.

I-2. Examples of Syntheses of Compounds According to the Invention

Method 1: General Procedure for Synthesis of Diarylmethylene Precursors

In a two-necked 50 mL round-bottom flask fitted with a reflux condenser, was placed a properly substituted aniline (6.7 mmol) diluted by addition of methanol (8 mL). Hydrochloric acid (0.34 mL, 37%) was then added dropwise to this solution, before addition of formalin (0.25 mL, 37% in water), and the resulting mixture was refluxed overnight under argon atmosphere. After completion of the reaction followed by TLC, the mixture was allowed to cool to room temperature and neutralized by slow addition of a 1M aqueous solution of NaHCO$_3$ until pH 8 was reached. The mixture was then poured into 20 mL of distilled water and the resulting aqueous layer extracted three times with chloroform (3×40 mL). The organic layers were then combined, dried over MgSO$_4$ and filtered before removal of the solvent under reduced pressure. The residue was finally purified by flash chromatography to give the target methylene compound that often easily crystallizes.

Compound 1 Precursor-1 (Procedure Abis):

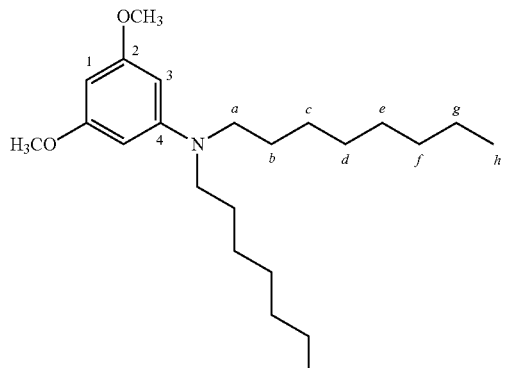

3,5-dimethoxy-N,N-dioctylaniline

To a suspension of K$_2$CO$_3$ (10.83 g, 78.5 mmol) in MeCN (80 mL) was added 3,5-dimethoxyaniline (2.0 g, 13.06 mmol) under argon, and the reaction mixture was stirred for 1 h at room temperature. After iodooctane (12.53 g, 52.2 mmol) was added, the mixture was refluxed for 24 h under stirring. The reaction mixture was then allowed to cool to room temperature, filtered through a pad of celite and concentrated under reduced pressure. The crude mixture was purified via the Biotage Isolera One (silica-packed snap cartridge; 0-20% CH$_2$Cl$_2$/petroleum ether) to afford the expected product as a greenish oil (4.26 g, 87%). $^1$H NMR (400 MHz, CDCl$_3$) δ 5.84 (br s, 3H, H$_1$+H$_3$), 3.77 (s, 6H, OCH$_3$), 3.24-3.18 (m, 4H, H$_a$), 1.62-1.53 (m, 4H, H$_b$), 1.36-1.23 (m, 20H, H$_{c-g}$), 0.92-0.85 (m, 6H, H$_h$). $^{13}$C NMR (100 MHz, CDCl$_3$) δ 161.8 (C$_2$), 150.1 (C$_4$), 91.3 (C$_3$), 87.3 (C), 55.1 (OCH$_3$), 51.3 (Ca), 31.9 (C$_b$), 29.6 (CC), 29.4 (C$_d$), 27.5 (Ce), 27.3 (C$_f$), 22.7 (C$_g$), 14.1 (C$_h$). HRMS: m/z: calcd for C$_{24}$H$_{44}$NO$_2$: 378.3367 [M+H]$^+$; found: 378.3359 [M+H]$^+$.

Compound 1 Precursor-2 (Procedure Abis):

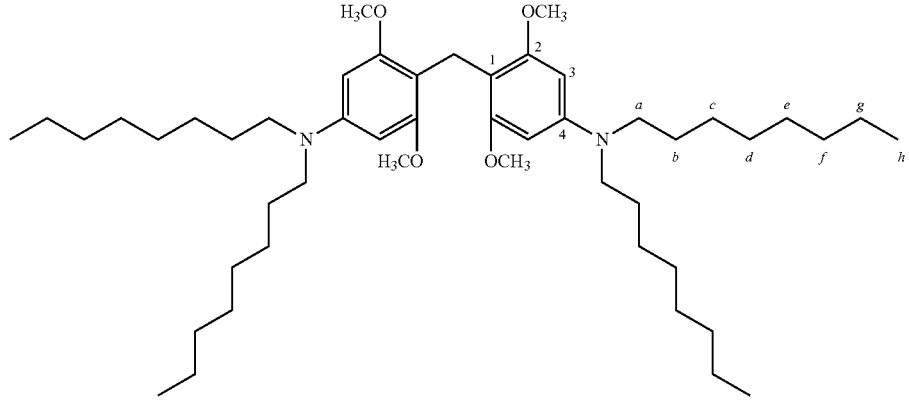

4,4'-methylenebis(3,5-dimethoxy-N,N-dioctylaniline)

The method 1 was applied to 3,5-dimethoxy-N,N-dioctylaniline (4.17 g, 11.04 mmol). The title compound was purified via the Biotage Isolera One (silica-packed snap cartridge; 0-10% CH$_2$Cl$_2$/cyclohexane) to afford a greenish oil (2.96 g, 69.5%). $^1$H NMR (400 MHz, CDCl$_3$) δ 5.85 (s, 4H, H$_3$), 3.76 (s, 2H, CH$_2$), 3.69 (s, 12H, OCH$_3$), 3.22-3.16

(m, 8H, $H_a$), 1.61-1.55 (m, 8H, $H_b$), 1.32-1.27 (m, 40H, $H_{c-g}$), 0.90-0.87 (m, 12H, $H_h$). $^{13}$C NMR (100 MHz, CDCl$_3$) δ 159.7 ($C_2$), 147.5 ($C_4$), 108.7 ($C_1$), 91.0 ($C_3$), 56.4 (OCH$_3$), 51.5 ($C_a$), 32.0 ($C_b$), 29.7 ($C_c$), 29.5 ($C_d$), 27.6 ($C_e$), 27.4 ($C_f$), 22.8 ($C_g$), 16.5 (CH$_2$), 14.2 ($C_h$). HRMS: m/z: calcd for $C_{49}H_{87}N_2O_4$: 767.6660 [M+H]$^+$; found: 767.6662 [M+H]$^+$.

Compound 5 Precursor-1 (Procedure Abis):

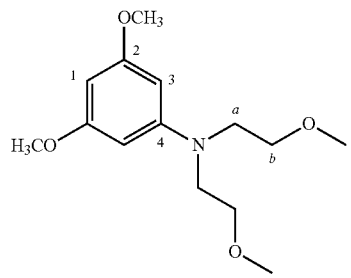

3,5-dimethoxy-N,N-bis(2-methoxyethyl)aniline

To a suspension of K$_2$CO$_3$ (10.06 g, 72.47 mmol) and NaI (1.09 g, 7.25 mmol) in DMF (55 mL) was added under argon 3,5-dimethoxyaniline (5.05 g, 32.94 mmol), and 2-chloroethyl methyl ether (6.06 mL, 66.54 mmol). The mixture was heated at 90° C. for 12 h under stirring. The reaction mixture was then allowed to cool to room temperature, filtered through a pad of celite and concentrated under reduced pressure. The title compound was purified via the Biotage Isolera One (silica-packed snap cartridge; 0-5% EtOAc/cyclohexane) to afford the expected product as a colorless oil (5.7 g, 64.3%). $^1$H NMR (400 MHz, CDCl$_3$) δ 5.91 (d, $^4J_{3-1}$=2.0 Hz, 2H, $H_3$), 5.88 (t, $^3J_{1-3}$=2.0 Hz, 1H, $H_1$), 3.77 (s, 6H, $^2$OCH$_3$), 3.54 (m, 8H, $H_{a,b}$), 3.35 (s, 6H, $^b$OCH$_3$). $^{13}$C NMR (100 MHz, CDCl$_3$) δ 161.9 ($C_2$), 149.9 ($C_4$), 91.6 ($C_3$), 88.4 ($C_1$), 70.4 ($C_b$), 59.1 ($^b$OCH$_3$), 55.3 ($^2$OCH$_3$), 51.4 (Ca). HRMS: m/z: calcd for $C_{14}H_{23}NO_4Na$: 292.1519 [M+Na]$^+$; found: 292.1520 [M+Na]$^+$.

Compound 5 Precursor-2 (Procedure Abis):

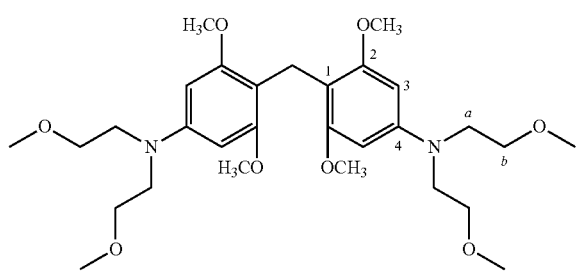

4,4'-methylenebis(N,N-bis(2-methoxyethyl)-3,5-dimethoxyaniline)

The method 1 was applied to 3,5-dimethoxy-N,N-bis(2-methoxyethyl)aniline (2.21 g, 8.22 mmol). The title compound was purified via the Biotage Isolera One (silica-packed snap cartridge; 0-20% EtOAc/cyclohexane) (1.44 g, 64%). $^1$H NMR (300 MHz, CDCl$_3$) δ 5.92 (s, 4H, $H_3$), 3.78 (s, 2H, CH$_2$), 3.69 (s, 12H, $^2$OCH$_3$), 3.54-3.49 (m, 16H, $H_{a,b}$), 3.35 (s, 12H, $^b$OCH$_3$). $^{13}$C NMR (75 MHz, CDCl$_3$) δ 159.7 ($C_2$), 147.1 ($C_4$), 109.3 ($C_1$), 90.9 ($C_3$), 70.6 (OCH$_2$), 59.1 ($^b$OCH$_3$), 56.4 ($^2$OCH$_3$), 51.5 (NCH$_2$), 16.4 (CH$_2$). HRMS: m/z: calcd for $C_{29}H_{47}N_2O_8$: 551.3327 [M+H]$^+$; found: 551.3324 [M+H]$^+$.

Compound 11 Precursor (Procedure Abis):

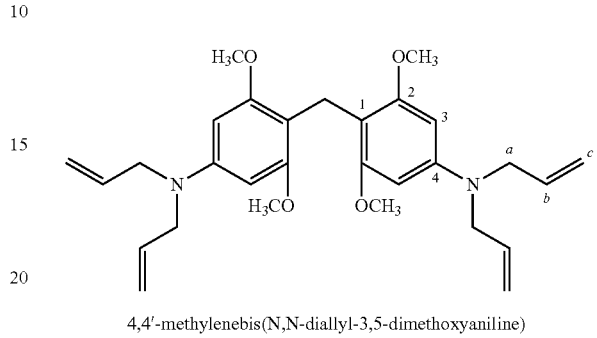

4,4'-methylenebis(N,N-diallyl-3,5-dimethoxyaniline)

The method 1 was applied to N,N-diallyl-3,5-dimethoxyaniline [Yang1999] (3.0 g, 12.85 mmol). The title compound was purified via the Biotage Isolera One (silica-packed snap cartridge; 0-10% CH$_2$Cl$_2$/cyclohexane) (2.06 g, 67%). $^1$H NMR (300 MHz) δ 5.98 (s, 4H, $H_3$), 5.96-5.87 (m, 4H, $H_b$), 5.26-5.16 (m, 8H, $H_c$), 3.91 (d, $^3J_{a-b}$=5.4 Hz, 8H, $H_a$), 3.85 (s, 2H, CH$_2$), 3.72 (s, 12H, OCH$_3$). $^{13}$C NMR (75 MHz) δ 159.4 ($C_2$), 148.0 ($C_4$), 134.9 ($C_b$), 116.0 ($C_c$), 109.3 ($C_1$), 91.3 ($C_3$), 56.2 (OCH$_3$), 53.4 ($C_a$), 16.5 (CH$_2$). HRMS: m/z: calcd for $C_{29}H_{39}N_2O_4$: 479.2904 [M+H]$^+$; found: 479.2891 [M+H]$^+$.

Compound 12 Precursor (Procedure Abis):

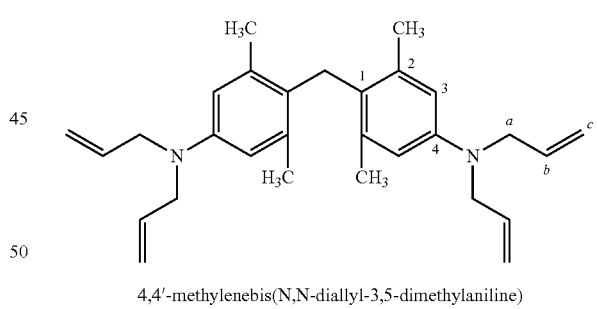

4,4'-methylenebis(N,N-diallyl-3,5-dimethylaniline)

The method 1 was applied to N,N-diallyl-3,5-dimethylaniline [Saitoh2004] (5.00 g, 24.84 mmol). The title compound was purified via the Biotage Isolera One (silica-packed snap cartridge; 10-50% CH$_2$Cl$_2$/cyclohexane) (3.25 g, 63%). $^1$H NMR (300 MHz, CD$_3$CN) δ 6.37 (s, 4H, $H_3$), 5.94-5.81 (m, 4H, $H_b$), 5.22-5.13 (m, 8H, $H_c$), 3.92-3.85 (m, 10H, $H_a$+CH$_2$), 2.10 (s, 12H, CH$_3$). $^{13}$C NMR (75 MHz, CD$_3$CN) δ 146.6 ($C_4$), 137.6 ($C_2$), 134.7 ($C_b$), 126.9 ($C_1$), 116.0 ($C_3$), 113.2 ($C_c$), 52.7 ($C_a$), 30.0 (CH$_2$), 21.6 (CH$_3$). HRMS: m/z: calcd for $C_{29}H_{39}N_2$: 415.3108 [M+H]$^+$; found: 415.3124 [M+H]$^+$.

Compound 33 Precursor-1 (Procedure Abis):

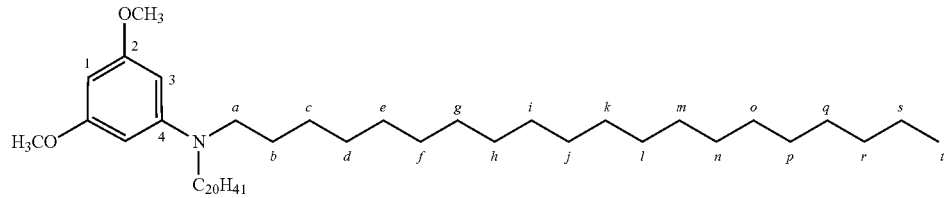

3,5-dimethoxy-N,N-dieicosylaniline

To a suspension of K$_2$CO$_3$ (6.0 g, 43.5 mmol) in dry MeCN (50 mL) was added 3,5-dimethoxyaniline (1.0 g, 6.53 mmol) under argon, and the reaction mixture was stirred for 2 h at room temperature. After eicosyl bromide (9.44 g, 26.11 mmol) was added, the mixture was refluxed for 24 h under stirring. Another portion of K$_2$CO$_3$ (6.0 g, 43.5 mmol) and eicosyl bromide (9.44 g, 26.11 mmol) were then added and the mixture was refluxed under stirring for another 24 h. The reaction mixture was then allowed to cool to room temperature and poured into a saturated NaCl solution. The resulting aqueous layer was extracted three times with methylene chloride. The organic layers were washed with distilled water, combined, dried over MgSO$_4$ and filtered before removal of the solvent under reduced pressure. The crude mixture was purified via the Biotage Isolera One (silica-packed snap cartridge; 10-40% CH$_2$Cl$_2$/petroleum ether) to afford the expected product as a white solid (1.72 g, 37%). $^1$H NMR (400 MHz, CDCl$_3$) δ 5.83 (br s, 3H, H$_1$+H$_3$), 3.77 (s, 6H, OCH$_3$), 3.23-3.18 (m, 4H, H$_a$), 1.30-1.25 (m, 72H, H$_b$-s), 0.90-0.86 (m, 6H, H$_t$). $^3$C NMR (100 MHz, CDCl$_3$) δ 161.8 (C$_2$), 150.1 (C$_4$), 91.3 (C$_3$), 87.3 (C$_1$), 55.2 (OCH$_3$), 51.4 (C$_a$), 32.1 (C$_b$), 29.9, 29.7, 29.5 (C$_{c-p}$), 27.5 (C$_q$), 27.3 (C$_r$), 22.8 (C$_s$), 14.3 (C$_r$).

Compound 33 Precursor-2 (Procedure Abis):

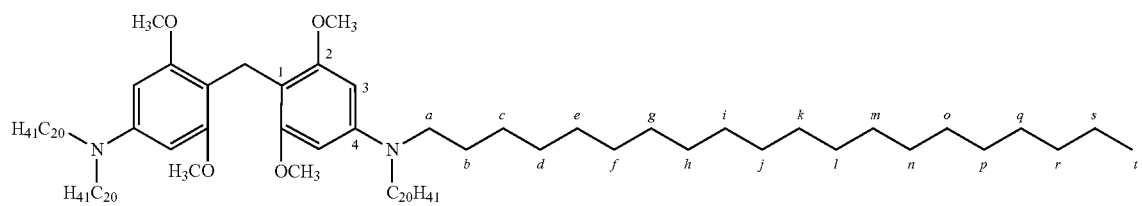

4,4'-methylenebis(3,5-dimethoxy-N,N-dieicosylaniline)

The method 1 was applied to 3,5-dimethoxy-N,N-dieicosylaniline (1.60 g, 2.24 mmol). The title compound was purified via the Biotage Isolera One (silica-packed snap cartridge; 50-100% CH$_2$Cl$_2$/petroleum ether) to afford a white microcrystalline solid (0.70 g, 44%). $^1$H NMR (400 MHz, CDCl$_3$) δ 5.84 (s, 4H, H$_3$), 3.78 (s, 2H, CH$_2$), 3.69 (s, 12H, OCH$_3$), 3.18 (t, $^3J_{a-b}$=7.4 Hz, 8H, H$_a$), 1.30-1.25 (m, 144H, H$_b$s), 0.88 (t, $^3J_{t-s}$=6.8 Hz, 12H, H). $^{13}$C NMR (100 MHz, CDCl$_3$) δ 160.0 (C$_2$), 148.0 (C$_4$), 109.7 (C$_1$), 92.1 (C$_3$), 56.5 (OCH$_3$), 51.8 (C$_a$), 32.1 (C$_b$), 29.9, 29.7, 29.5 (C$_{c-p}$), 27.8 (C$_q$), 27.5 (C$_r$), 22.8 (C$_s$), 16.8 (CH$_2$), 14.1 (C$_t$).

Compound 34 Precursor-1 (Procedure Abis):

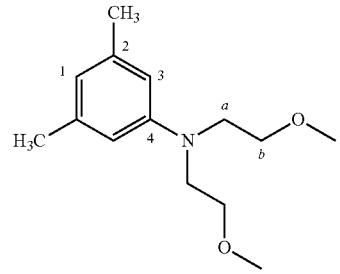

3,5-dimethyl-N,N-bis(2-methoxyethyl)aniline

To a suspension of K$_2$CO$_3$ (13.50 g, 89.87 mmol) and NaI (0.621 g, 4.14 mmol) in DMF (55 mL) was added under argon 3,5-dimethylaniline (4.00 mL, 32.08 mmol), and 2-chloroethyl methyl ether (6.40 mL, 70.40 mmol). The mixture was heated at 90° C. for 48 h under stirring. The reaction mixture was then allowed to cool to room temperature, filtered through a pad of celite and concentrated under reduced pressure. The title compound was purified via the Biotage Isolera One (silica-packed snap cartridge; 0-5% EtOAc/cyclohexane) to afford the expected product (4.215 g, 55.3%). $^1$H NMR (300 MHz, CDCl$_3$) δ 6.40-6.35 (m, 3H, H$_{1,3}$), 3.57-3.53 (m, 8H, H$_{a,b}$), 3.37 (s, 6H, OCH$_3$), 2.28 (s, 6H, CH$_3$). $^{13}$C NMR (75 MHz, CDCl$_3$) δ 145.3 (C$_4$), 138.5 (C$_2$), 118.3 (C$_1$), 110.3 (C$_3$), 70.2 (OCH$_2$), 59.1 (OCH$_3$), 50.9 (NCH$_2$), 21.8 (CH$_3$).

Compound 34 Precursor-2 (Procedure Abis):

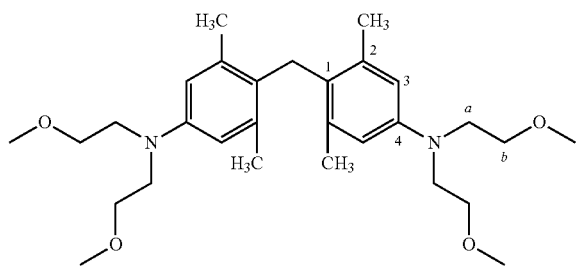

4,4'-methylenebis(N,N-bis(2-methoxyethyl)-3,5-dimethylaniline)

The method 1 was applied to 3,5-dimethyl-N,N-bis(2-methoxyethyl)aniline (4.215 g, 17.76 mmol). The title compound was purified via the Biotage Isolera One (silica-packed snap cartridge; 0-30% $CH_2Cl_2$/cyclohexane) (2.58 g, 60%). $^1$H NMR (300 MHz, $CDCl_3$) δ 6.38 (s, 4H, $H_3$), 3.91 (s, 2H, $CH_2$), 3.57-3.54 (m, 16H, $H_{a,b}$), 3.39 (s, 12H, $OCH_3$), 2.13 (s, 12H, $CH_3$). $^{13}$C NMR (75 MHz, $CDCl_3$) δ 145.5 ($C_4$), 137.7 ($C_2$), 126.7 ($C_1$), 112.5 ($C_3$), 70.3 ($OCH_2$), 59.0 ($OCH_3$), 50.9 ($NCH_2$), 29.8 ($CH_2$), 21.5 ($CH_3$).

Compound 35-precursor:

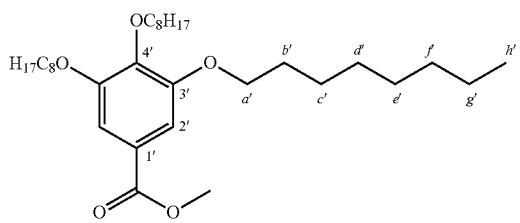

Methyl 3,4,5-trioctyloxybenzoate

To a suspension of $K_2CO_3$ (20.88 g, 150.0 mmol) in DMF (100 mL) was added under argon methyl 3,4,5-trihydroxybenzoate (4.0 g, 21.6 mmol), and 1-bromooctane (11.28 mL, 72.24 mmol). The mixture was heated at 80° C. for 48 h under stirring. The reaction mixture was then allowed to cool to room temperature, before pouring into a large amount of water. The resulting mixture was then extracted with dietyl ether. The organic layers were washed with distilled water, combined, dried over $MgSO_4$ and filtered before removal of the solvent under reduced pressure. The expected product was obtained as a white solid (7.35 g, 65.5%). $^1$H NMR (400 MHz, $CD_3CN$) δ 7.23 (s, 2H, $H_2$'), 4.00-3.94 (m, 6H, $H_{a'}$), 3.83 (s, 3H, $OCH_3$), 1.78-1.72 (m, 6H, $H_{b'}$), 1.36-1.23 (m, 24H, $H_{c'-g'}$), 0.90-0.86 (s, 9H, $H_{h'}$). $^{13}$C NMR (100 MHz, $CDCl_3$) δ 167.1 ($CO_2Me$), 152.9 ($C_3$'), 142.5 ($C_4$'), 124.8 ($C_1$'), 108.1 ($C_2$'), 69.3 ($C_{a'}$), 52.2 ($OCH_3$), 32.0, 30.5, 29.6, 29.4, 26.2, 22.8, 14.2 ($C_{h'}$).

Method 2: General Procedure for Synthesis of Target Diarylmethyliums

To a vigorously stirred solution of the proper methylene compound in a minimum amount of THF was dropwise added a solution of oxidant (here more particularly a hydride abstraction reagent) in THF, preferably 2,3-dichloro-5,6-dicyano-1,4-benzoquinone (DDQ) (1.0 equivalent). After stirring for approximately 2.5 h at room temperature, the reaction mixture was concentrated under reduced pressure and then dropwise added (after previous filtration through a pipette plugged with cotton wool) to a saturated solution of the desired counteranion, e.g. potassium hexafluorophosphate (metathesis of $DDQH^-/PF_6^-$). This suspension was stirred for 20 minutes before filtration of the dark precipitate, which was taken up in $CH_2C_2$. The resulting deeply (blue-) colored organic layer was washed with a minimum amount of distilled water (until giving a colorless aqueous layer) and concentrated under reduced pressure. The residue was finally purified by slow vapor crystallization. Noticingly, the final metathesis may be avoided to afford the methylium compound associated to a counteranion derived from the reduced form of the oxidant sooner utilized, e.g. $DDQH^-$.

Compound 1-$DDQH^-$ (Procedure Abis):

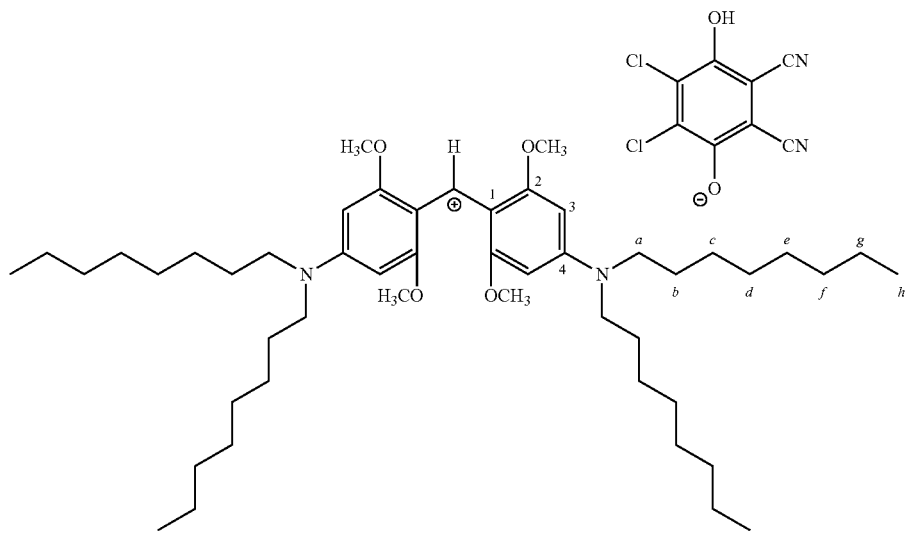

Bis(4-(dioctylamino)-2,6-dimethoxyphenyl)methylium 2,3-dichloro-5,6-dicyano-4-hydroxyphenolate The method 2 was applied to 4,4'-methylenebis(3,5-dimethoxy-N,N-dioctylaniline) (2.94 g, 3.83 mmol). The title compound was purified by a simple washing with cyclohexane and $CH_2Cl_2$ to yield the desired carbenium as a metal-like lacquer, displaying either a magenta or a copper/gold luster whether the round-bottom flask in which evaporation occurred was observed from the outside or not (3.4 g, 89.3%). $^1$H NMR (400 MHz, $CD_3CN$) δ 8.29 (s, 1H, CH$^+$), 5.85 (s, 4H, $H_3$), 3.82 (s, 12H, $OCH_3$), 3.56-3.49 (m, 8H, $H_a$), 1.74-1.64 (m, 8H, H), 1.45-1.22 (m, 40H, $H_{c-g}$), 0.94-0.83 (m, 12H, $H_h$). $^{13}$C NMR (100 MHz, $CD_3CN$) δ 165.1 ($C_2$), 158.7 ($C_4$), 142.5 (CH$^+$), 112.0 ($C_1$), 89.4 ($C_3$), 56.9 ($OCH_3$), 52.5 ($C_a$), 32.5 (C), 30.0 (C), 28.4 ($C_d$), 27.5 (Ce), 27.5 ($C_f$), 23.4 ($C_g$), 14.4 ($C_h$). HRMS (ESI+): m/z: calcd for $C_{49}H_{85}N_2O_4$: 765.6504 [M–DDQH]$^+$; found: 765.6505 [M–DDQH]$^+$. HRMS (ESI+): m/z: calcd for $C_8HCl_2N_2O_2$: 226.9421 [DDQH]$^-$; found: 226.9423 [DDQH]$^-$.

Compound 1-$PF_6^-$ (Procedure Abis):

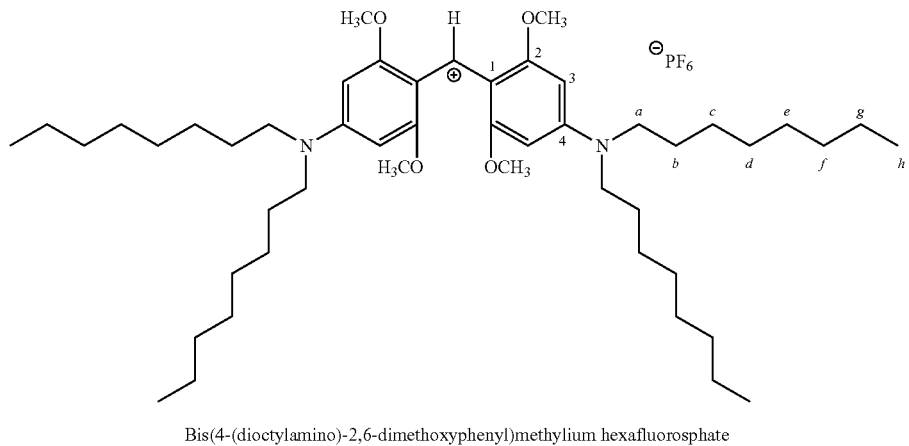 [SMILES: CCCCCCCCN(CCCCCCCC)c1cc(OC)c([CH+]c2c(OC)cc(N(CCCCCCCC)CCCCCCCC)cc2OC)c(OC)c1 ; "PF6"]

Bis(4-(dioctylamino)-2,6-dimethoxyphenyl)methylium hexafluorosphate

Figure 2:
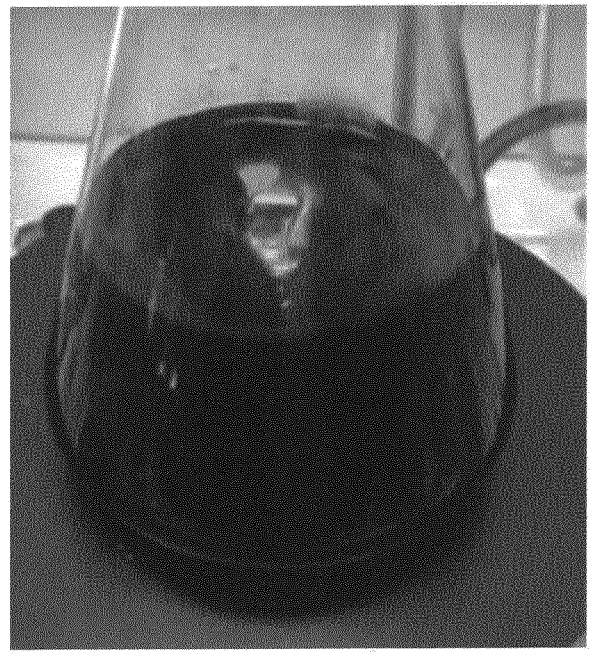

A small quantity of the previously described bis(4-(dioctylamino)-2,6-dimethoxyphenyl)methylium 2,3-dichloro-5,6-dicyano-4-hydroxyphenolate (0.463 g, 0.46 mmol) was engaged in a metathesis step using potassium hexafluorophosphate. It's worth noticing that while dropwise addition of the acetonitrile concentrated solution of 1-DDQH$^-$ into the saturated aqueous solution of $KPF_6$, a highly reflective magenta-colored film self-assembled at the air-liquid interface (as can be seen in FIG. 2). The film was harvested, taken up in $CH_2Cl_2$ and washed with a minimum amount of distilled water to yield the desired carbenium as a metal-like lacquer, displaying either a magenta or a copper/gold luster whether the round-bottom flask in which evaporation occurred was observed from the outside or not (0.356 g, 85.0%). $^1$H NMR (400 MHz, $CD_3CN$) δ 8.29 (s, 1H, CH$^+$), 5.85 (s, 4H, $H_3$), 3.82 (s, 12H, $OCH_3$), 3.56-3.49 (m, 8H, $H_a$), 1.74-1.64 (m, 8H, H), 1.44-1.26 (m, 40H, $H_{eg}$), 0.95-0.88 (m, 12H, $H_h$). $^{13}$C NMR (100 MHz, $CD_3CN$) δ 165.1 ($C_2$), 158.8 ($C_4$), 142.5 (CH$^+$), 111.9 ($C_1$), 89.5 ($C_3$), 56.8 ($OCH_3$), 52.4 ($C_a$), 32.5 ($C_b$), 30.0 ($C_c$), 28.3 ($C_d$), 27.6 ($C_e$), 27.5 ($C_f$), 23.4 ($C_g$), 14.4 ($C_h$). HRMS (ESI+): m/z: calcd for $C_{49}H_{85}N_2O_4$: 765.6504 [M–$PF_6$]$^+$; found: 765.6505 [M–$PF_6$]$^+$. HRMS (ESI-): m/z: calcd for $F_6P$: 144.9647 [$PF_6$]$^-$; found: 144.9650 [$PF_6$]$^-$.

Compound 5-DDQH⁻ (Procedure Abis):

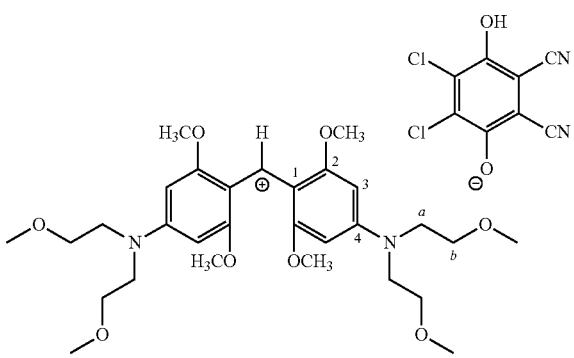

Bis(4-(bis(2-methoxyethyl)amino)-2,6-dimethoxyphenyl)methylium
2,3-dichloro-4,5-dicyano-4-hydroxyphenolate The method 2 was applied to 4,4'-methylenebis(N,N-bis(2-methoxyethyl)-3,5-dimethoxy-aniline) (0.934 g, 1.69 mmol). The title compound was purified by simple washing with Et₂O and CH₂C₂ to yield the desired carbenium as a reddish copper metallic solid (1.2 g, 91.3%). ¹H NMR (300 MHz, CD₃CN) δ 8.34 (s, 1H, CH⁺), 6.02 (s, 4H, H₃), 3.83 (s, 12H, ²OCH₃), 3.81 (t, 8H, NCH₂), 3.65 (t, 8H, OCH₂), 3.33 (s, 12H, OCH₃) ¹³C NMR (75 MHz, CD₃CN) δ 165.1 (C₂), 160.1 (C₄), 143.3 (CH⁺), 112.4 (C₁), 90.3 (C₃), 71.1 (OCH₂), 59.3 (OCH₃), 57.0 (²OCH₃), 52.6 (NCH₂). HRMS (ESI+): m/z: calcd for C₂₉H₄₅N₂O₈: 549.3170 [M–DDQH]⁺; found: 549.3168 [M–DDQH]⁺. HRMS (ESI−): m/z: calcd for C₈HCl₂N₂O₂: 226.9421 [DDQH]⁻; found: 227.2017 [DDQH]⁻.

Compound 5-PF₆⁻ (Procedure Abis):

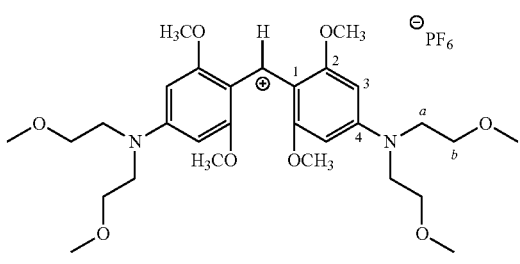

Figure 1:
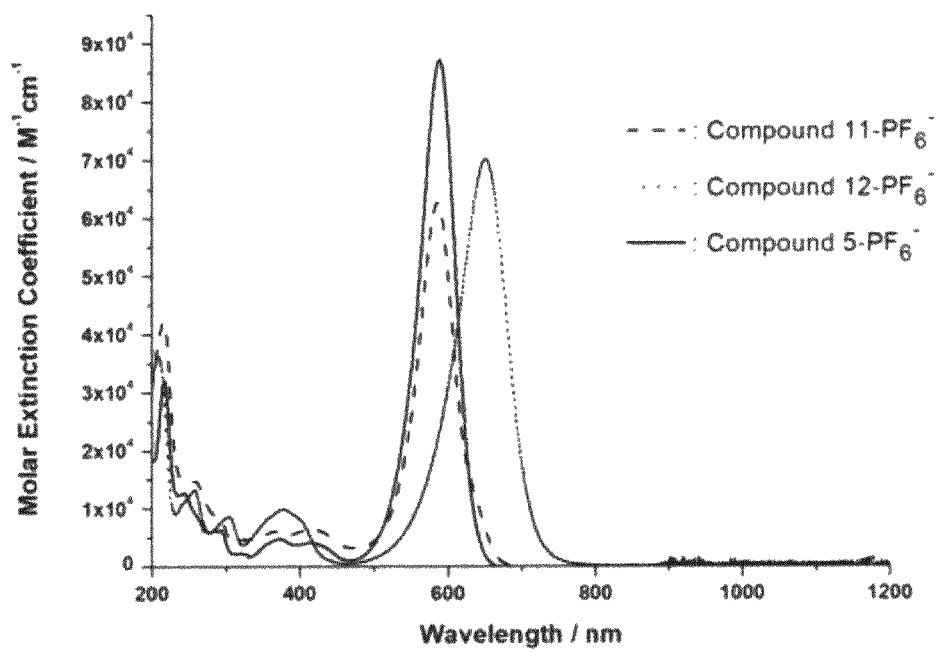

Bis(4-(bis(2-methoxyethyl)amino)-2,6-dimethoxyphenyl)methylium
hexafluorophosphate A small quantity of the previously described bis(4-(bis(2-methoxyethyl)amino)-2,6-dimethoxyphenyl)methylium 2,3-dichloro-5,6-dicyano-4-hydroxyphenolate (0.616 g, 0.79 mmol) was engaged in a metathesis step using potassium hexafluorophosphate. It's worth noticing that while dropwise addition of the acetonitrile concentrated solution of 5-DDQH⁻ into the saturated aqueous solution of KPF₆, a highly reflective gold-colored film self-assembled at the air-liquid interface (as can be seen in FIG. 7). The film was harvested, taken up in CH₂Cl₂ and washed with a minimum amount of distilled water. to yield the desired carbenium as a metal-like lacquer, displaying either a copper/gold or a green luster whether the round-bottom flask in which evaporation occurred was observed from the outside or not (0.465 g, 84.7%). ¹H NMR (300 MHz, CD₃CN) δ 8.34 (s, 1H, CH⁺), 6.02 (s, 4H, H₃), 3.83 (s, 12H, ²OCH₃), 3.81 (t, 8H, NCH₂), 3.65 (t, 8H, OCH₂), 3.33 (s, 12H, OCH₃). ¹³C NMR (75 MHz, CD₃CN) δ 165.1 (C₂), 160.2 (C₄), 143.3 (CH⁺), 112.4 (C₁), 90.3 (C₃), 71.1 (OCH₂), 59.3 (ᵇOCH₃), 57.0 (²OCH₃), 52.6 (NCH₂). HRMS (ESI+): m/z: calcd for C₂₉H₄₅N₂O₈: 549.3170 [M–PF₆]⁺; found: 549.3167 [M–PF₆]⁺. HRMS (ESI−): m/z: calcd for F₆P: 144.9647 [PF₆]⁻; found: 144.9650 [PF₆]⁻. UV-vis-NIR (CH₃CN) λmax/nm (ε/L mol⁻¹ cm⁻¹): 588 (87 178) (as can be seen in FIG. 1).

Compound 11-DDQH⁻ (Procedure Abis):

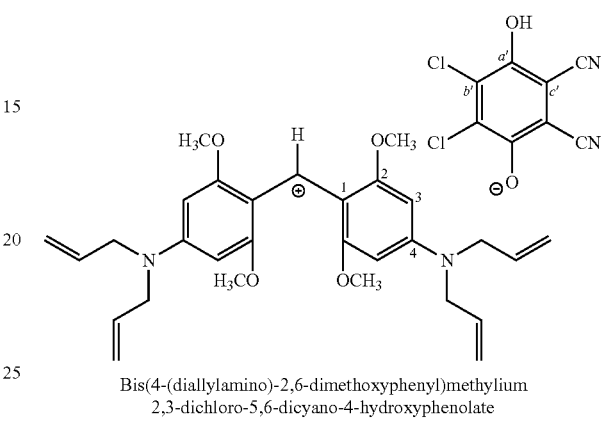

Bis(4-(diallylamino)-2,6-dimethoxyphenyl)methylium
2,3-dichloro-5,6-dicyano-4-hydroxyphenolate The method 2 was applied to 4,4'-methylenebis(N,N-diallyl-3,5-dimethoxyaniline) (3.67 g, 7.67 mmol) to yield the title compound that was simply filtered from the reaction mixture as a microcrystallized lustrous green solid (affording a blue solution) (4.92 g, 91%). ¹H NMR (300 MHz, DMSO-d₆) δ 8.24 (s, 1H, CH⁺), 6.08-5.81 (m, 8H, H_b+H₃), 5.38-5.14 (m, 8H, H_c), 4.40-4.15 (m, 8H, H_a), 3.81 (s, 12H, OCH₃). ¹³C NMR (75 MHz, DMSO-d₆) δ 163.6 (C₂), 158.3 (C₄), 141.5 (CH⁺), 132.5 (C_b), 117.5 (C_c), 110.9 (C₁), 89.1 (C₃), 56.3 (OCH₃), 53.4 (C_a).

Compound 11-PF₆⁻ (Procedure Abis):

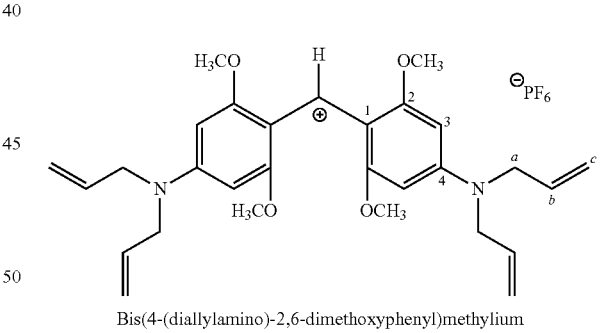

Bis(4-(diallylamino)-2,6-dimethoxyphenyl)methylium
hexafluorophosphate

A small quantity of the previously described bis(4-(diallylamino)-2,6-dimethoxyphenyl)methylium 2,3-dichloro-5,6-dicyano-4-hydroxyphenolate (1.0 g, 1.42 mmol) was engaged in a metathesis step using potassium hexafluorophosphate to give after evaporation a metal-like lacquer, displaying either a copper or a green luster whether the round-bottom flask in which evaporation occurred was observed from the outside or not (as can be seen in FIGS. 13 & 14) (0.75 g, 88%). ¹H NMR (300 MHz, CD₃CN) δ 8.36 (s, 1H, CH⁺), 5.99-5.90 (m, 4H, H_b), 5.89 (s, 4H, H₃), 5.31-5.20 (m, 8H, H_c), 4.23-4.15 (d, ³J_{a-b}=5.1 Hz, 8H, H_a), 3.79 (s, 12H, OCH₃). ¹³C NMR (75 MHz, CD₃CN) δ 165.2 (C₂), 160.0 (C₄), 143.9 (CH⁺), 133.0 (C_b), 118.0 (C_c), 112.5

($C_1$), 90.0 ($C_3$), 57.0 ($OCH_3$), 54.6 ($C_a$). HRMS (ESI+): m/z: calcd for $C_{29}H_{37}N_2O_4$: 477.2748 $[M-PF_6]^+$; found: 477.2767 $[M-PF_6]^+$. HRMS (ESI-): m/z: calcd for $F_6P$: 144.9647 $[PF_6]^-$; found: 145.0754 $[PF_6]^-$. UV-vis-NIR ($CH_3CN$) λmax/nm (ε/L $mol^{-1}$ $cm^{-1}$): 585.5 (62 616) (as can be seen in FIG. 1).

Compound 12-$PF_6^-$ (Procedure Abis):

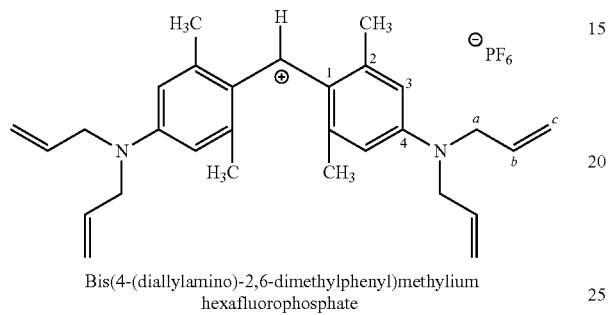

Bis(4-(diallylamino)-2,6-dimethylphenyl)methylium hexafluorophosphate

The method 2 was applied to 4,4'-methylenebis(N,N-diallyl-3,5-dimethylaniline) (1.74 g, 4.21 mmol). The crude product was washed with EtOAc to give after evaporation the title compound as a metal-like lacquer, displaying either a magenta or a bronze luster whether the round-bottom flask in which evaporation occurred was observed from the outside or not (as can be seen in FIGS. 17 & 18) (1.60 g, 68%). $^1$H NMR (300 MHz, $CD_3CN$) δ 8.45 (s, 1H, $CH^+$), 6.66 (s, 4H, $H_3$), 5.98-5.89 (m, 4H, $H_b$), 5.30-5.20 (m, 8H, $H_c$), 3.92-3.85 (d, $^3J_{a-b}$=5.1 Hz, 8H, $H_a$), 2.22 (s, 12H, $CH_3$). $^{13}$C NMR (75 MHz, $CD_3CN$) δ 159.3 ($CH^+$), 157.1 ($C_4$), 148.6 ($C_2$), 132.7 ($C_b$), 130.6 (C), 118.0 (C), 115.5 ($C_3$), 54.2 ($C_a$), 21.9 ($CH_3$). HRMS (ESI+): m/z: calcd for $C_{29}H_{37}N_2$: 413.2951 $[M-PF_6]^+$; found: 413.2949 $[M-PF_6]^+$; calcd for $C_{30}H_{41}N_2O$: 445.3213 $[M-PF_6+MeOH]^+$; found: 445.3225 $[M-PF_6+MeOH]^+$. HRMS (ESI-): m/z: calcd for $F_6P$: 144.9647 $[PF_6]^-$; found: 145.0840 $[PF_6]^-$. UV-vis-NIR ($CH_3CN$) λmax/nm (ε/L $mol^{-1}$ $cm^{-1}$): 650 (70 133) (as can be seen in FIG. 1).

Compound 33-$PF_6^-$ (Procedure Abis):

The method 2 was applied to 4,4'-methylenebis(3,5-dimethoxy-N,N-dieicosylaniline) (0.70 g, 0.486 mmol). The crude product was washed with diethyl ether to give after evaporation the title compound as a metal-like lacquer. (0.70 g, 91%). $^1$H NMR (400 MHz, $CDCl_3$) δ 8.34 (s, 1H, $CH^+$), 5.76 (s, 4H, $H_3$), 3.85 (s, 12H, $OCH_3$), 3.49 (t, $^3J_{a-b}$=7.4 Hz, 8H, $H_a$), 1.70 (m, 8H, $H_b$), 1.40-1.25 (m, 136H, $H_e$ s), 0.88 (t, $^3J_{t-s}$=6.8 Hz, 12H, $H_t$). $^{13}$C NMR (100 MHz, $CDCl_3$) δ 164.8 ($C_2$), 158.3 ($C_4$), 143.4 ($CH^+$), 112.4 ($C_1$), 88.9 ($C_3$), 56.2 ($OCH_3$), 52.3 ($C_a$), 32.1 ($C_b$), 29.9, 29.7, 29.5 ($C_{c-p}$), 28.2 ($C_q$), 27.3 ($C_r$), 22.8 ($C_s$), 14.1 ($C_t$).

Compound 34-$DDQH^-$ (Procedure Abis):

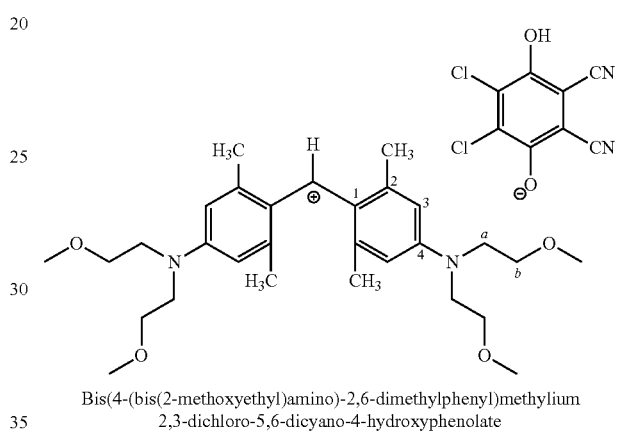

Bis(4-(bis(2-methoxyethyl)amino)-2,6-dimethylphenyl)methylium 2,3-dichloro-5,6-dicyano-4-hydroxyphenolate The method 2 was applied to 4,4'-methylenebis(N,N-bis (2-methoxyethyl)-3,5-dimethylaniline) (1.52 g, 3.12 mmol). The title compound was purified by a simple washing with diethyl ether to yield the desired carbenium as a metal-like pale pink lacquer (1.83 g, 82.0%). $^1$H NMR (300 MHz, $CD_3CN$) δ 8.37 (s, 1H, $CH^+$), 6.71 (s, 4H, $H_3$), 3.79 (t, $^3J_{a-b}$=5.3 Hz, 8H, $NCH_2$), 3.61 (t, $^3J_{a-b}$=5.3 Hz, 8H, $OCH_2$), 3.30 (s, 12H, $OCH_3$), 2.21 (s, 12H, $CH_3$). $^{13}$C NMR (75 MHz, $CD_3CN$) δ 158.3 ($CH^+$), 157.0, 157.5 ($C_4$), 153.2, 148.2 ($C_2$), 130.8, 130.4 ($C_1$), 118.3, 115.5 ($C_3$), 101.4, 70.8 ($OCH_2$), 59.3 ($OCH_3$), 52.4 ($NCH_2$), 22.0 ($CH_3$).

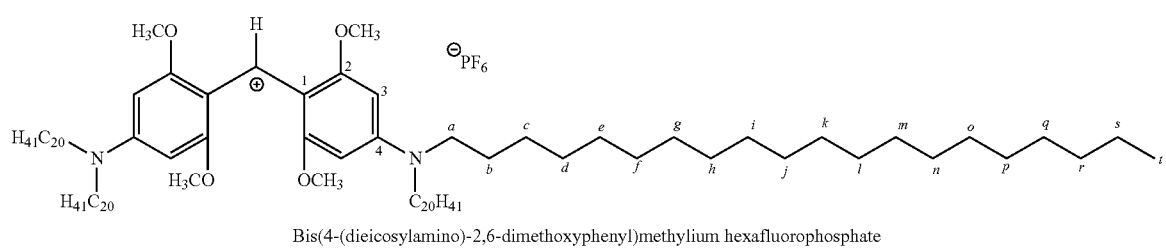

Bis(4-(dieicosylamino)-2,6-dimethoxyphenyl)methylium hexafluorophosphate

Compound 34-PF$_6^-$ (Procedure Abis):

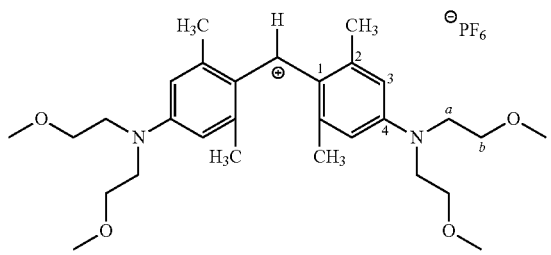

Bis(4-(bis(2-methoxyethyl)amino)-2,6-dimethoxyphenyl)methylium hexafluorophosphate A small quantity of the previously described bis(4-(bis(2-methoxyethyl)amino)-2,6-dimethylphenyl)methylium 2,3-dichloro-5,6-dicyano-4-hydroxyphenolate (0.300 g, 0.42 mmol) was engaged in a metathesis step using potassium hexafluorophosphate. It's worth noticing that while dropwise addition of the acetonitrile concentrated solution of 34-DDQH$^-$ into the saturated aqueous solution of KPF$_6$, a highly reflective magenta-colored film self-assembled at the air-liquid interface (as can be seen in FIG. 21). The film was harvested, taken up in CH$_2$Cl$_2$ and washed with a minimum amount of distilled water to yield the desired carbenium as a metal-like lacquer, displaying either a copper or a magenta/blue luster whether the round-bottom flask in which evaporation occurred was observed from the outside or not (0.260 g, 98%). $^1$H NMR (300 MHz, CD$_3$CN) δ 8.40 (s, 1H, CH$^+$), 6.73 (s, 4H, H$_3$), 3.80 (t, $^3J_{a-b}$=5.5 Hz, 8H, NCH$_2$), 3.62 (t, $^3J_{a-b}$=5.5 Hz, 8H, OCH$_2$), 3.31 (s, 12H, OCH$_3$), 2.23 (s, 12H, CH$_3$). $^{13}$C NMR (75 MHz, CD$_3$CN) δ 158.3 (CH$^+$), 157.5 (C$_4$), 148.2 (C$_2$), 130.4 (C$_1$), 115.5 (C$_3$), 70.8 (OCH$_2$), 59.3 (OCH$_3$), 52.3 (NCH$_2$), 21.9 (CH$_3$).

Compound 35-PF$_6$— (procedure Gbis):

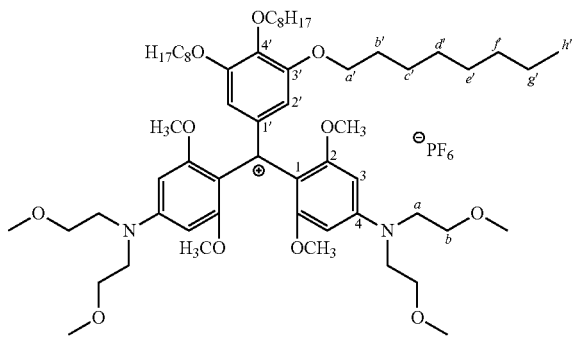

Bis(4-(bis(2-methoxyethyl)amino)-2,6-dimethoxyphenyl)-3',4',5'-tris(octyloxy)phenylmethylium hexafluorophosphate To a flask charged with TMEDA (0.12 mL, 0.80 mmol) and anhydrous THF (2.5 mL) cooled at −78° C. under argon was added n-butyllithium in hexane solution (4.6 mL, 11.5 mmol). The milky solution was stirred for 15 min, before dropwise addition of a THF solution of 3,5-dimethoxy-N,N-bis(2-methoxyethyl)aniline (2.15 g, 8.0 mmol). The vigorously stirred mixture was maintained at −78° C. for another 15 min and then allowed to gradually warm to room temperature. After 3 h, the mixture was then cooled again at −78° C. and diluted with 6 mL of anhydrous THF before addition of methyl 3,4,5-tris(octyloxy)benzoate (2.08 g, 4.0 mmol). The reaction mixture temperature was then maintained at −78° C. for another 15 min and stirred at room temperature for 36 h. To the reaction mixture was added H$_2$O (20 mL). The solvent was removed and the residue was taken up in a minimum amount of methanol before addition of a 60% aqueous HPF$_6$ solution (4.0 mmol). The product was extracted with dichloromethane and the solvent volume was reduced under vacuum. The resulting highly lustrous residue was washed several times with diethyl ether to give the expected compound, which was further purified by recrystallization.

References reporting the preparation and characterization of some starting materials used in the above described general:

[Yang1999]: Yang, S.-C., Hung, C.-W. Synthesis, 1999, 10, 1747-1752.

[Saitoh2004] Saitoh, T., Yoshida, S., Ichikawa, J. Org. Lett., 2004, 6, 4563-4565.

II—Optical Properties of the Compounds According to the Invention

II—1. Absorption Properties

Measurement of the molar extinction coefficients of compounds 5-PF$_6^-$, 11-PF$_6^-$, 12-PF$_6^-$ was carried as follows: for each compound, three independent 10-5 mol·L$^{-1}$ acetonitrile solutions (200 mL) were prepared, and absorbances were measured in a 1 cm optical path quartz cuvettes (against reference 1 cm optical path quartz cuvette containing pure acetonitrile) in a double-beam Cary 500 spectrophotometer (Varian).

As it appears on FIG. 1, the compounds according to the invention are characterized by a single sharp absorption band in the visible region of the electromagnetic spectrum, and a high molar extinction coefficient. Appropriate chemical modulations allow the absorption bands of the compounds according to the invention to span over an extended region of the visible electromagnetic spectrum (hence allowing display of numerous metal-like effects).

Accordingly, chromophoric properties of compounds of the invention are directly observed from these solutions. For example, an intense deep blue color is observed for 5-PF$_6^-$, 11-PF$_6^-$, 12-PF$_6^-$ dissolved in acetonitrile.

II-2. Other Optical Properties

FIG. 2 corresponds to a picture of a magenta-colored liquid mirror obtained by dropwise addition of an acetonitrile solution of compound 1-DDQH$^-$, into a stirred saturated aqueous solution of KPF$_6$. The impressive reflective properties of the film are maintained whether the solution is stirred or not. This feature is of peculiar interest to design liquid mirrors, specifically for astronomy purposes, needing a parabolic surface, usually shaped by rotation.

Figure 3:
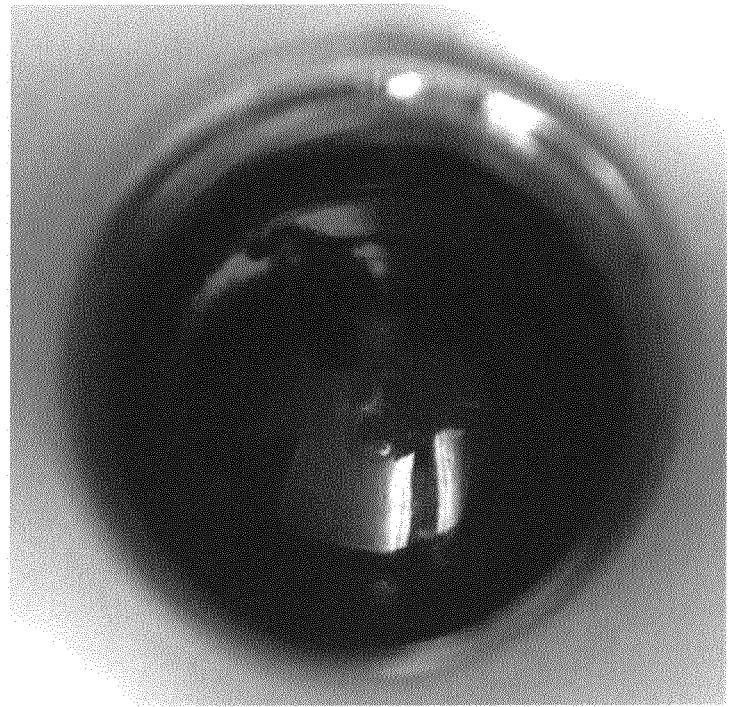

FIG. 3 corresponds to a picture of a magenta-colored mirror of compound 1-PF$_6^-$ that forms on the glass wall of a container, resulting from evaporation of a concentrated acetonitrile solution of chromophoric compound 1-PF$_6^-$. This self-assembled organic material constitutes a real mirror that reflects with fidelity surrounding objects.

Figure 4:
FIG. 4 represents a photograph of a magenta reflective film covering a PTFE magnetic stir bar and its retriever after dipping into the solution displaying at the air-liquid interface the liquid mirror illustrated in FIG. 2.

FIG. 4 represents a photograph of a magenta reflective film covering a PTFE magnetic stir bar and its retriever after dipping into the solution displaying at the air-liquid interface the liquid mirror illustrated in FIG. 2, thus demonstrating the ability of the film to be transferred from the top of a fluid onto other surfaces, while keeping its reflective features.

Figure 5:
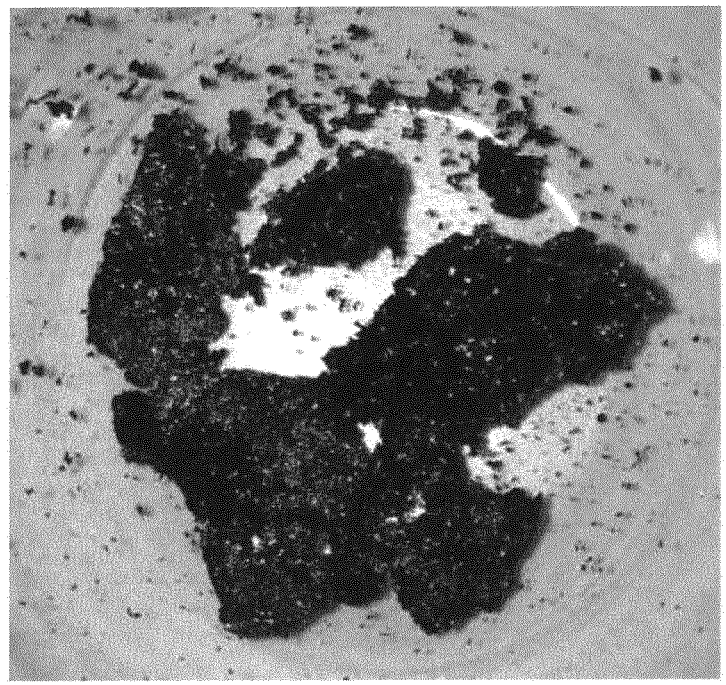
FIG. 5 represents a macroscopic view of compound $5\text{-DDQH}^-$ in its solid form, characterized by its reddish copper flakes appearance.

FIG. 5 represents a macroscopic view of compound 5-DDQH⁻ in its solid form, characterized by its reddish copper flakes appearance, demonstrating the angle-dependency of the reflective properties.

Figure 6:
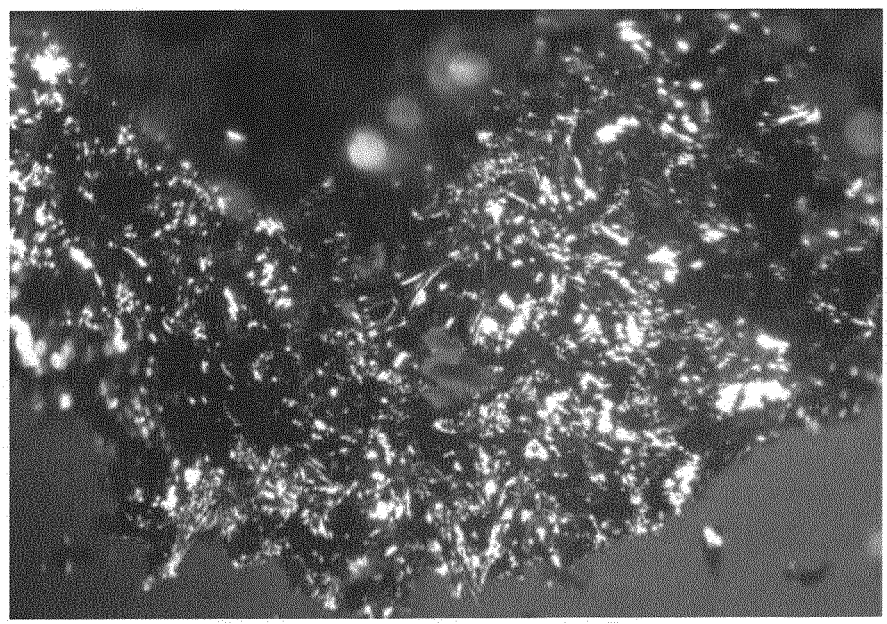
FIG. 6 represents a microscopic view of compound $5\text{-DDQH}^-$ in its solid form, characterized by its metallic and copper/gold flakes appearance, obtained with a Zeiss-Stemi 2000-C microscope.

FIG. 6 represents a microscopic view of compound 5-DDQH⁻ in its solid form, characterized by its metallic and copper/gold flakes appearance, obtained with a Zeiss-Stemi 2000-C microscope, demonstrating impressive reflective properties (metal foil aspect).

FIG. 7 corresponds to a picture of a gold-like liquid mirror obtained by dropwise addition of an acetonitrile solution of compound 5-DDQH⁻ into a stirred saturated aqueous solution of KPF$_6$. The impressive reflective properties of the film are maintained whether the solution is stirred or not. This feature is of peculiar interest to design liquid mirrors, specifically for astronomy purposes, needing a parabolic surface, usually shaped by rotation.

FIG. 8 corresponds to a picture of a self-assembled gold-like liquid mirror observed few minutes after dropwise addition of an acetonitrile solution of compound 5-PF$_6^-$ onto the surface of a saturated aqueous solution of NaCl. This homogeneous low-dimensional organic material constitutes a real mirror that reflects with fidelity surrounding objects.

FIG. 9 corresponds to a picture of a copper/gold-like mirror of compound 5-PF$_6^-$ that forms on the wall of a round-bottom flask, resulting from the evaporation under reduced pressure of a concentrated acetonitrile solution of chromophoric compound 5-PF$_6^-$. This self-assembled organic material constitutes a real mirror that reflects with fidelity surrounding objects.

FIG. 10 represents a macroscopic view of compound 5-PF$_6^-$ in its polycrystalline form, characterized by its green metallic luster appearance, demonstrating the angle-dependency of the reflective properties.

FIG. 11 represents a microscopic view of compound 5-PF$_6^-$ in its polycristalline form, obtained with a Zeiss-Stemi 2000-C microscope, demonstrating the angle-dependency of the reflective properties.

FIG. 12 displays a microscopic view of compound 11-PF$_6^-$ in its microcrystallized form, characterized by its impressive dual metallic (copper/gold & bronze/green) reflective properties, obtained with a Zeiss-Stemi 2000-C microscope.

FIG. 13 represents a photograph of the copper/gold reflective mirror formed on the inner-wall of a round-bottom flask after simple evaporation of a concentrated solution of 11-PF$_6^-$ in acetonitrile, hence showing the propensity of the molecule to self-assemble to yield a well-shaped coating that displays optical properties of interest (e.g. obtaining of a reflective metal-like luster).

FIG. 14 represents a photograph (outside view) of the green-bronze reflective mirror formed on the inner-wall of a round-bottom flask after simple evaporation of a concentrated solution of 11-PF$_6^-$ in acetonitrile, hence showing the propensity of the molecule to self-assemble to yield a well-shaped coating that displays optical properties of interest (e.g. obtaining of a reflective metal-like luster).

FIG. 15 displays a microscopic view of compound 11-DDQH⁻ in its microcrystallized form, characterized by its glittering appearance, obtained with a Zeiss-Stemi 2000-C microscope.

FIG. 16 displays a macroscopic view of compound 12-PF$_6^-$ in its solid form, characterized by its dual magenta/copper luster appearance, in accordance with the dual metallic appearance illustrated in following FIGS. 17 & 18.

FIG. 17 represents a photograph of a magenta reflective mirror of compound 12-PF$_6^-$ that forms on the inner-wall of a round-bottom flask after simple evaporation of a concentrated acetonitrile solution of 12-PF$_6^-$, hence showing the propensity of the molecule to self-assemble to yield a well-shaped coating that displays optical properties of interest (e.g. obtaining of a reflective metal-like luster).

FIG. 18 represents a photograph of the outside view of a copper reflective mirror of compound 12-PF$_6^-$ that forms on the inner-wall of a round-bottom flask after simple evaporation of a concentrated acetonitrile solution of 12-PF$_6^-$, hence showing the propensity of the molecule to self-assemble to yield a well-shaped coating that displays optical properties of interest (e.g. obtaining of a reflective metal-like luster).

FIG. 19 corresponds to a picture of a purple liquid mirror obtained by dropwise addition of an acetonitrile solution of compound 33-DDQH⁻ into a stirred saturated aqueous solution of KPF$_6$. The impressive reflective properties of the film are maintained whether the solution is stirred or not. This feature is of peculiar interest to design liquid mirrors.

FIG. 20 represents a macroscopic view of compound 34-DDQH⁻ in form of a metallic pink lacquer, demonstrating the angle-dependency of the reflective properties.

FIG. 21 corresponds to a picture of a magenta/pink-like liquid mirror obtained by dropwise addition of an acetonitrile solution of compound 34-DDQH⁻ into a stirred saturated aqueous solution of KPF$_6$. The impressive reflective properties of the film are maintained whether the solution is stirred or not. This feature is of peculiar interest to design liquid mirrors.

FIG. 22 represents a photograph of a magenta/pink reflective film covering a PTFE magnetic stir bar and its retriever after dipping into the solution displaying at the air-liquid interface the liquid mirror illustrated in FIG. 21, thus demonstrating the ability of the film to be transferred from the top of a fluid onto other surfaces, while keeping its reflective features.

FIG. 23 displays a macroscopic view of compound 34-PF$_6^-$ in its solid form, characterized by its reddish copper luster appearance, demonstrating the angle-dependency of the reflective properties.

FIG. 24 represents a photograph of a magenta/blue-like mirror of compound 34-PF$_6^-$ that forms on the inner-wall of a round-bottom flask after simple evaporation of a concentrated acetonitrile solution of 34-PF$_6^-$, hence showing the propensity of the molecule to self-assemble to yield a well-shaped coating that displays optical properties of interest (e.g. obtaining of a reflective metal-like luster).

FIG. 25 represents a photograph of the outside view of a copper reflective mirror of compound 34-PF$_6^-$ that forms on the inner-wall of a round-bottom flask after simple evaporation of a concentrated acetonitrile solution of 34-PF$_6^-$, hence showing the propensity of the molecule to self-assemble to yield a well-shaped coating that displays optical properties of interest (i.e. obtaining of a reflective metal-like luster).

FIG. 26 represents a photograph of a reflective layer of compound 35-PF$_6^-$ that forms on the inner-wall of a round-bottom flask after simple evaporation of a concentrated dichloromethane solution of 35-PF$_6^-$, hence showing the propensity of the molecule to self-assemble to yield a well-shaped coating that displays optical properties of interest (e.g. obtaining of a reflective metal-like luster).

III—Films Made of Compounds According to the Invention

III-1. Elaboration and Characterization of Solid Films Made of Compounds of the Invention: Spin Coating and Quantitative Reflectance Measurements The compounds according to the invention are soluble in most organic polar solvents. For example, an acetonitrile ($CH_3CN$) solution of a compound of the invention (for example at a concentration of 5 mg/mL) can be prepared.

This solution is spin-coated onto a substrate, and after solvent evaporation under ambient conditions, a uniform film exhibiting a reflective appearance is obtained.

It has been observed that films obtained with compounds according to the invention are able to cover various surfaces, notably glass (see FIGS. 3, 9, 13 & 14, 17 & 18, 24 & 25, 26).

Films of different thicknesses can be spin-coated by varying the spin-coating speed or acceleration or duration, or by varying the concentration or the volume of the solution that is deposited onto the substrate. Also, several layers of films can be superimposed by repeating successive steps of spin coating as above.

Drop-casting, dip-coating, bar-coating, spraying and doctor blade techniques may also represent alternative efficient modes of preparation of solid films made of compounds of the invention. Optical properties are somewhat angle-dependent and reinforced by the background color of the substrate.

III-2. Elaboration and Characterization of Organic Metal-Like Liquid Films Made of Compounds of the Invention: Dropwise Addition and Quantitative Reflectance Measurements Whether the compound of interest bears rather hydrophilic or lipophilic moieties, it is mandatory to appropriately choose the nature of the deposition fluid in order to obtain a film with optimized optical properties.

A solution of one of the compounds (around 10 mg/mL or more) is dropwise added into a stirred saturated aqueous solution (of $KPF_6$ or NaCl for example). After 30 min-1 h, a homogeneous reflective film covers the liquid surface, that can if needed be carefully transferred onto another surface. In condition that the compound is deposited on an appropriate liquid (regarding its physicochemical properties), such films can be stored at least weeks without visible degradation of their optical properties.

It has been observed that films obtained with compounds according to the invention are able to cover various surfaces (notably glass and PTFE). More precisely, compounds 1-$PF_6^-$, 5-$PF_6^-$ and 34-$PF_6^-$ are particularly prone to deposit on PTFE-coated objects (see FIGS. 4 & 22) which are usually known for their anti-stick properties, what can open new fields of application.

Spraying or more sophisticated techniques may be envisioned to perform an efficient mode of preparation of films made of compounds of the invention (regarding the purpose or the type of liquid on which deposit).

The invention claimed is:

1. A compound of following general formula (I):

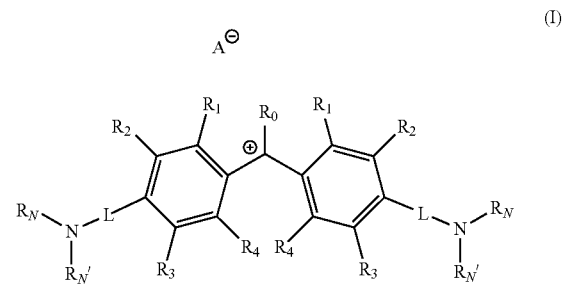

wherein:

$R_0$ represents a hydrogen atom, a halogen atom, a ($C_1$-$C_6$)alkyl, ($C_1$-$C_6$)haloalkyl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $OR_5$, $SR_6$, $NR_7R_8$, $COR_{11}$, $CO_2R_{12}$, $CONR_{13}R_{14}$, $SO_2R_{15}$, CN or $NO_2$, group, or is selected from the group consisting of:

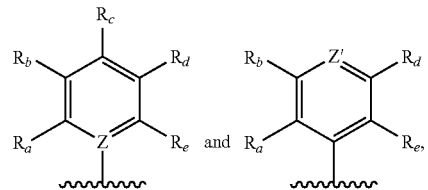

wherein:

Z represents C or $N^+A_z^-$ and Z' represents N or $N^+$—$R_c'$ $A_z^-$, wherein $A_z^-$ represents a monovalent organic or inorganic anion, and $R_c'$ represents a hydrogen atom or a ($C_1$-$C_6$)alkyl group, $R_a$ and $R_e$ each represent, independently of each other, a hydrogen atom, a halogen atom, a ($C_1$-$C_{20}$)alkyl, ($C_1$-$C_{20}$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $OR_{22}$ or $SR_{23}$ group, and $R_b$, $R_c$ and $R_d$ each represent, independently of each other, a hydrogen atom, a halogen atom or a ($C_1$-$C_{20}$)alkyl, ($C_1$-$C_{20}$)haloalkyl, cycloalkyl, heterocycle or O($C_1$-$C_{20}$)alkyl, group;

$R_1$ represents a halogen atom, a ($C_1$-$C_{20}$)alkyl, ($C_2$-$C_{12}$) alkynyl, ($C_1$-$C_{20}$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$) alkyl, $(CH_2)_mOR_{24}$, $(CH_2)m'SR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;

$R_4$ represents a halogen atom, a ($C_1$-$C_{20}$)alkyl, ($C_2$-$C_{12}$) alkynyl, ($C_1$-$C_{20}$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$) alkyl, $(CH_2)_mOR_{24}$, $(CH_2)m'SR_{25,0}R_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;

or both $R_4$ groups form together a bond or a chain selected from the group consisting of $-C(R_{42}R_{43})-$, $-(CH_2)_n-$, $-Si(R_{44}R_{45})-$, $-CH_2-Y-CH_2-$, and $-Y-CH_2-CH_2-Y'-$, wherein:

Y and Y' each represent, independently of each other, O, S or NH, n is equal to 2 or 3, $R_{42}$ and $R_{43}$, each represent, independently of each other, a $(C_1-C_6)$alkyl or an aryl group, and $R_{44}$ and $R_{45}$ each represent, independently of each other, a $(C_1-C_6)$alkyl or an aryl group;

L represents a bond, or a group selected from the group consisting of:

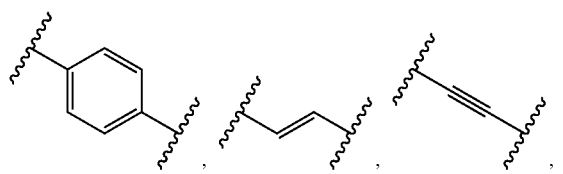
,

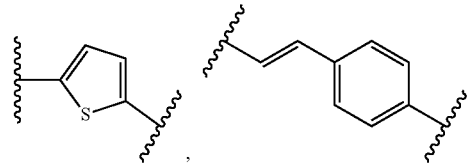
,

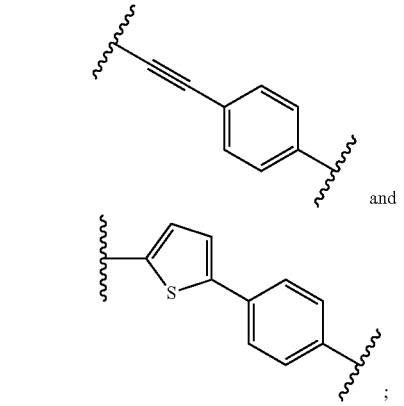

;

$R_2$ and $R_3$ each represent, independently of each other, a hydrogen atom, a halogen atom, a $(C_1-C_6)$alkyl, $(C_1-C_6)$haloalkyl, aryl, heteroaryl, aryl-$(C_1-C6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_{49}$ or $NR_{51}R_{52}$ group;

or

L represents:

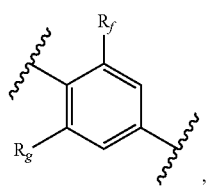
, and $R_f$ and $R_2$, and $R_g$ and $R_3$ form together with the carbon atoms that carry them a cycloalkenyl or aryl group;

$R_N$ and $R_N'$ each represent, independently of each other, a $(C_7-C_{20})$alkyl or $(C_7-C_{20})$haloalkyl group, said group being optionally substituted by one or more groups selected from $OR_{62}$, $SR_{63}$ and $NR_{64}R_{65}$, or a group selected from the group consisting of:

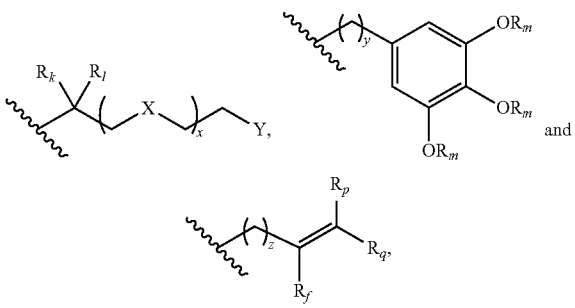

wherein:

X represents O, S or $NR_{57}$,

Y represents $OR_{58}$, $SR_{59}$ or $NR_{60}R_{61}$, x is equal to 0, 1, 2 or 3, y is equal to 0, 1, 2 or 3, z is equal to 0, 1, 2 or 3, $R_k$ and $R_l$ each represent, independently of each other, a hydrogen atom or a $(C_1-C_6)$alkyl group, $R_m$ represents a $(C_1-C_{20})$alkyl group, $R_r$ represents a hydrogen atom or a $(C_1-C_6)$alkyl group, $R_p$ and $R_q$ each represent, independently of each other, a hydrogen atom, a $(C_1-C_6)$alkyl, an aryl or heteroaryl group, $R_{57}$ to $R_{65}$ each represent, independently of each other, a hydrogen atom or a $(C_1-C_6)$alkyl group;

$R_5$ to $R_8$, $R_{11}$ to $R_{15}$, $R_{24}$, $R_{25}$, $R_{28}$, $R_{29}$, $R_{32}$, $R_{36}$, $R_{38}$, $R_{39}$, $R_{49}$, $R_{51}$ and $R_{52}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{64}$, $SR_{65}$ and $NR_{66}R_{67}$ group, wherein $R_{64}$ to $R_{67}$ each represent, independently of each other, a hydrogen atom or a $(C_1-C_6)$alkyl group;

$R_{22}$, $R_{23}$, $R_{26}$ and $R_{27}$ each represent, independently of each other a hydrogen atom, a $(C_1-C_{20})$alkyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group, wherein $R_{66}$ to $R_{69}$ each represent, independently of each other, a hydrogen atom or a $(C_1-C_6)$alkyl group;

and $A^-$ represents a monovalent, organic or inorganic anion, with the proviso that when $R_1$ and $R_4$ are the same, and $R_0$ is:

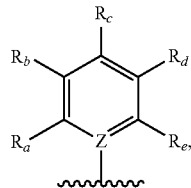

wherein Z represents C, at least one of $R_a$ and $R_e$ is not the same as $R_1$.

2. The compound according to claim 1, wherein $R_N=R_N'$.

3. The compound according to claim 1, wherein $R_0$ represents a hydrogen atom, a halogen atom, a $(C_1-C_6)$alkyl, $(C_1-C_6)$haloalkyl, cycloalkyl, heterocycle, $OR_5$, $SR_6$, $NR_7R_8$, CN, or $NO_2$ group, or is selected from the group consisting of:

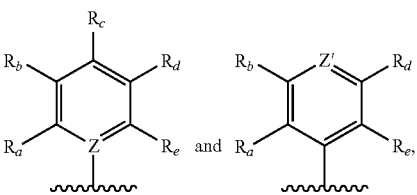

wherein:

Z represents C or $N^+A_z^-$ and Z' represents N or $N^+$—$R_c'$ $A_z^-$, wherein $A_z^-$ represents a monovalent organic or inorganic anion, and $R_c'$ represents a hydrogen atom or a $(C_1-C_6)$alkyl group, $R_a$ and $R_e$ each represent, independently of each other, hydrogen atom, a halogen atom, a $(C_1-C_6)$alkyl, $(C_1-C_6)$haloalkyl, $OR_{22}$ or $SR_{23}$ group, and $R_b$, $R_c$ and $R_d$ each represent, independently of each other, a hydrogen atom, a halogen atom or a $(C_1-C_6)$alkyl or $(C_1-C_6)$haloalkyl group, with the proviso that when $R_1$ and $R_4$ are the same, and $R_0$ is:

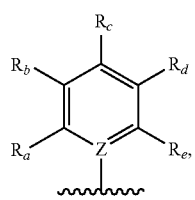

wherein Z represents C, at least one of $R_a$ and $R_e$ is not the same as $R_1$.

4. The compound according to claim 1, wherein $R_0$ represents a hydrogen atom, a halogen atom, a $(C_1-C_6)$alkyl, $(C_1-C_6)$haloalkyl, CN or $NO_2$ group, or is:

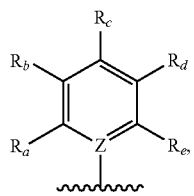

wherein:

Z represents C, $R_a$ and $R_e$ each represent, independently of each other, a hydrogen atom, a halogen atom, a $(C_1-C_6)$alkyl or $(C_1-C_6)$haloalkyl group, and $R_b$, $R_c$ and $R_d$ each represent a hydrogen atom.

5. The compound according to claim 1, wherein $R_1$ represents a halogen atom, a $(C_1-C_{20})$alkyl, $(C_1-C_{20})$haloalkyl, $(CH_2)_mOR_{24}$, $(CH_2)_m'SR_{25}$, $OR_{26}$, $SR_{27}$ or $NR_{28}R_{29}$ group, wherein m and m' are, independently of each other, equal to 1, 2 or 3.

6. The compound according to claim 1, wherein:

$R_4$ represents a halogen atom, a $(C_1-C_{20})$alkyl, $(C_1-C_{20})$haloalkyl, $(CH_2)_mOR_{24}$, $(CH_2)_m'SR_{25}$, $OR_{26}$, $SR_{27}$ or $NR_{28}R_{29}$ group wherein m and m' are, independently of each other, equal to 1, 2 or 3;

or both $R_4$ groups form together a bond or a chain selected from the group consisting of —$C(R_{42}R_{43})$—, —$(CH_2)_n$—, —$Si(R_{44}R_{45})$— and —Y—$CH_2$—$CH_2$—Y'—, wherein:

Y and Y' each represent, independently of each other, O, S or NH, n is equal to 2 or 3, $R_{42}$ and $R_{43}$, each represent, independently of each other, a $(C_1-C_6)$alkyl group, and $R_{44}$ and $R_{45}$ each represent, independently of each other, a $(C_1-C_6)$alkyl group.

7. The compound according to claim 1, wherein L represents a bond.

8. The compound according to claim 1, wherein $R_2$ and $R_3$ each represent, independently of each other, a hydrogen atom, a halogen atom, a $(C_1-C_6)$alkyl or $(C_1-C_6)$haloalkyl group, notably a hydrogen atom or a $(C_1-C_6)$alkyl group.

9. The compound according to claim 1, wherein $R_1=R_4$ and/or $R_2=R_3$ and/or $R_a=R_e$.

10. The compound according to claim 1, wherein it is chosen from the following compounds:

| 101 | 102 | |
|---|---|---|
| 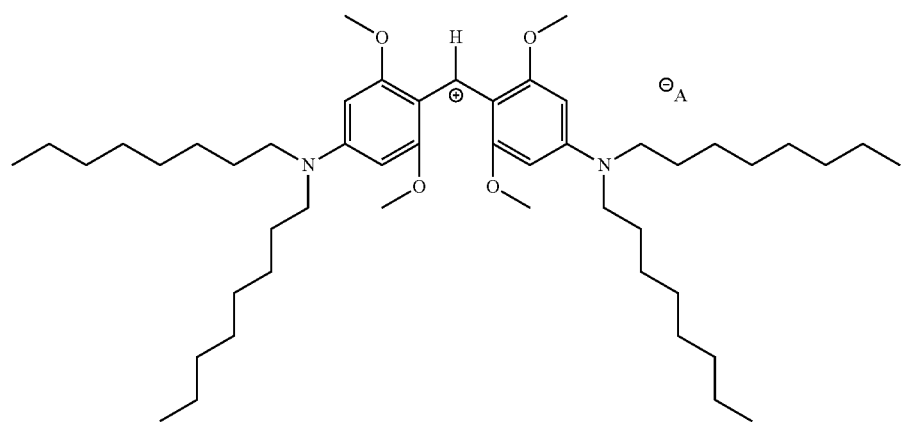 | | 1 |
| 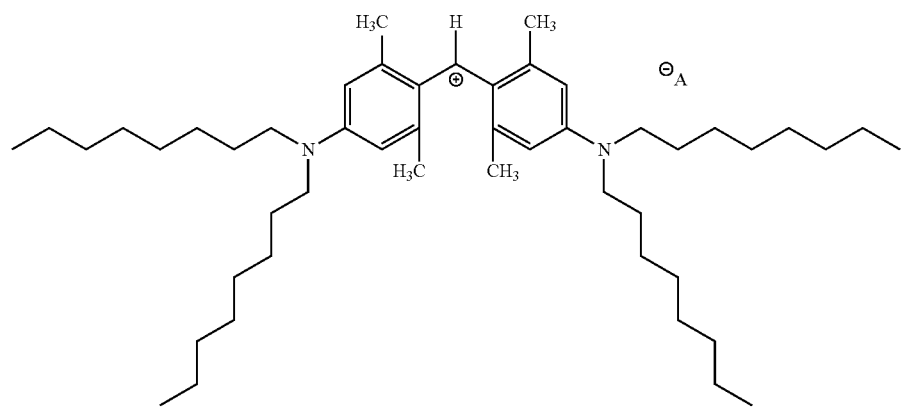 | | 2 |
| 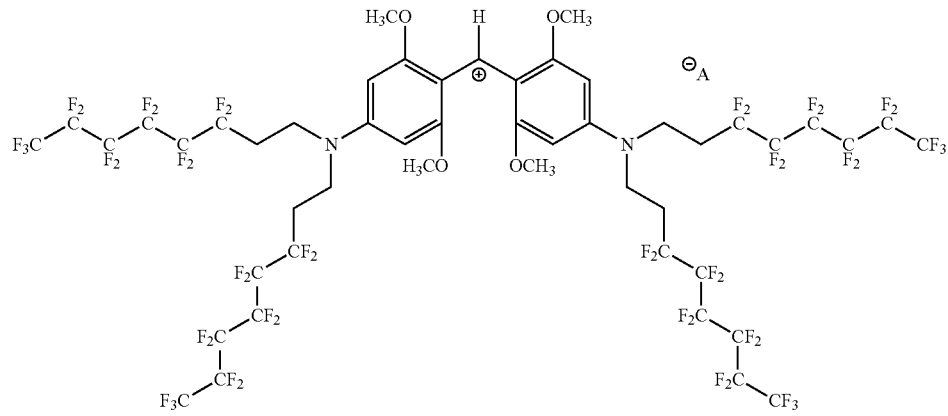 | | 3 |
| 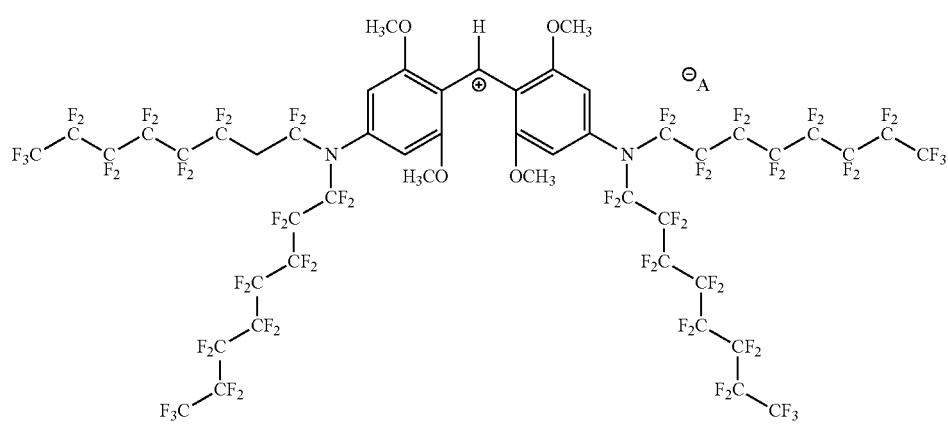 | | 4 |

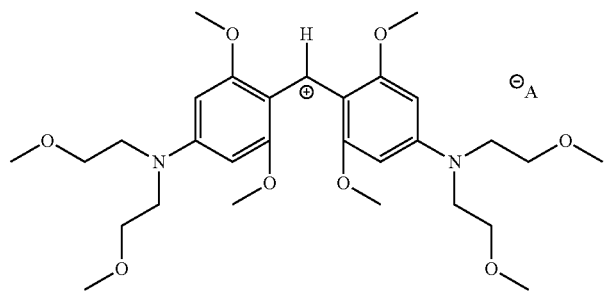
5
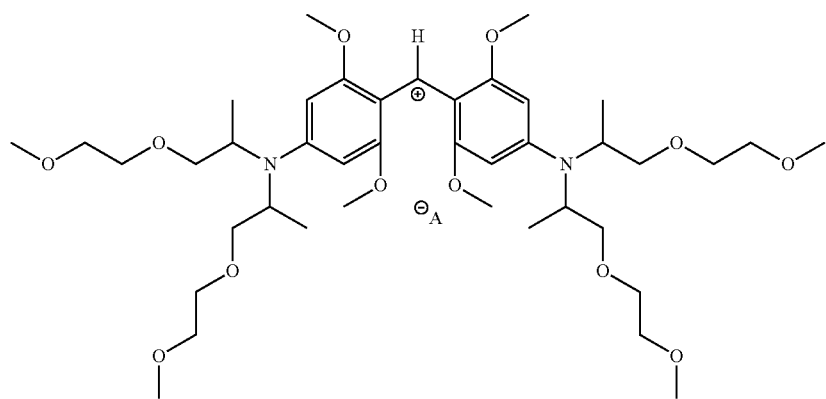
6
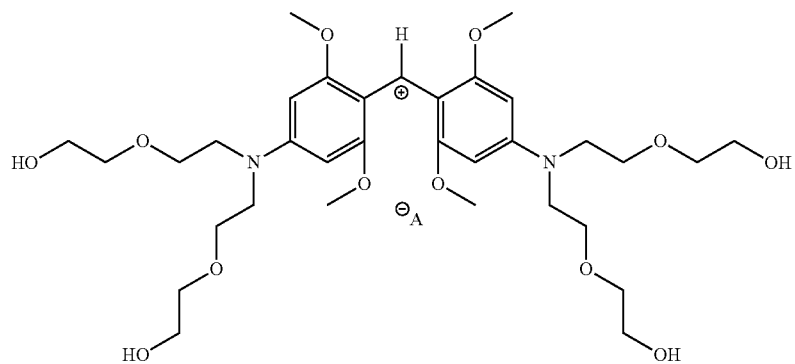
7
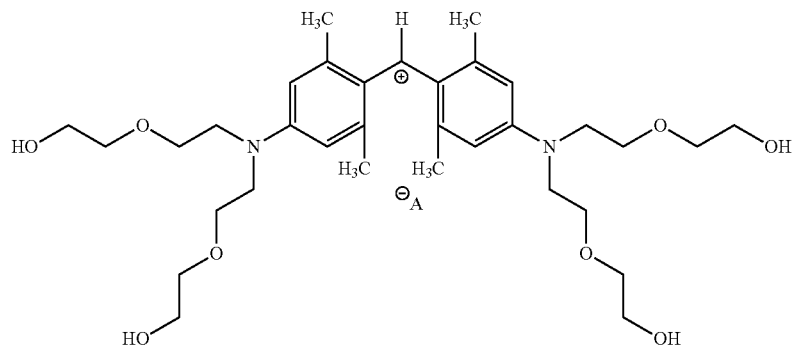
8

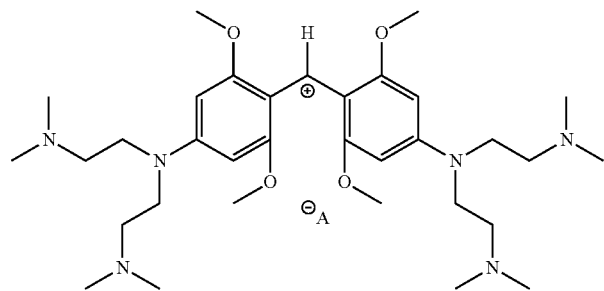
9
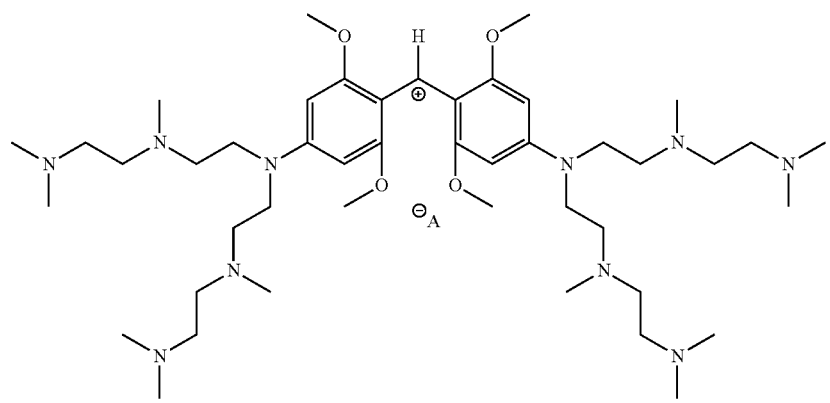
10
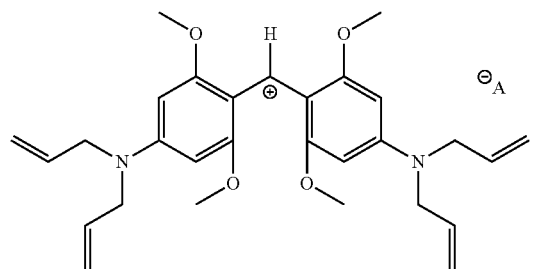
11
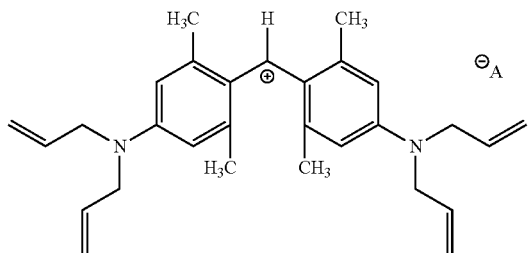
12
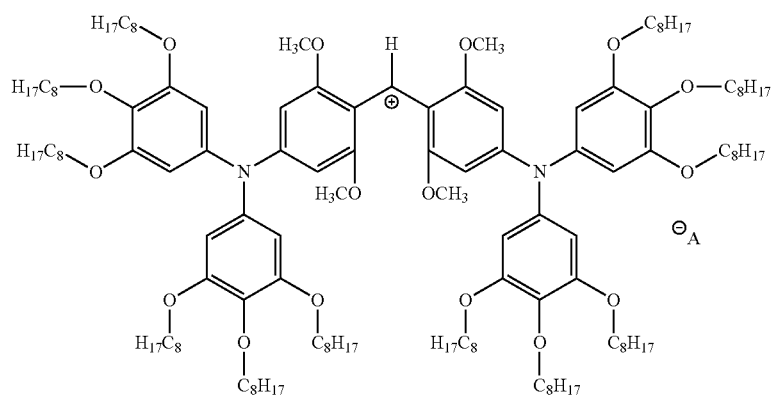
13

-continued
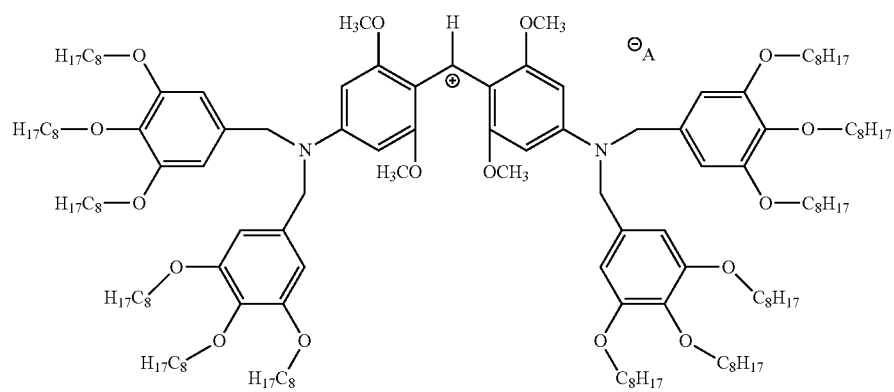
14
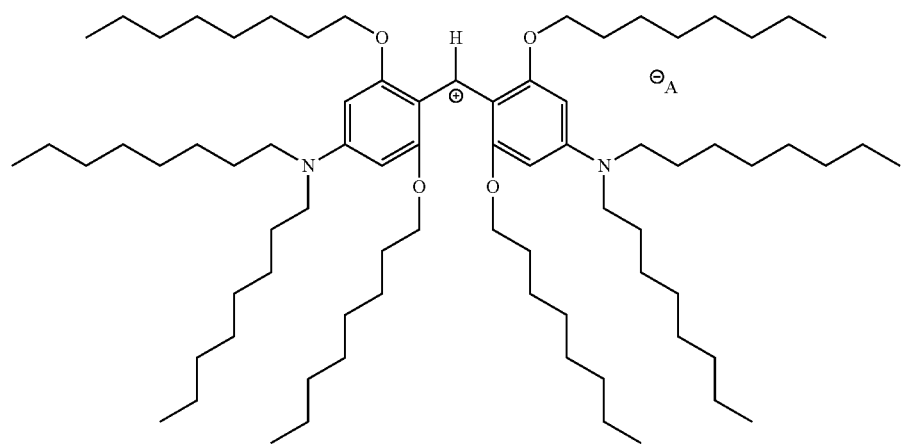
15
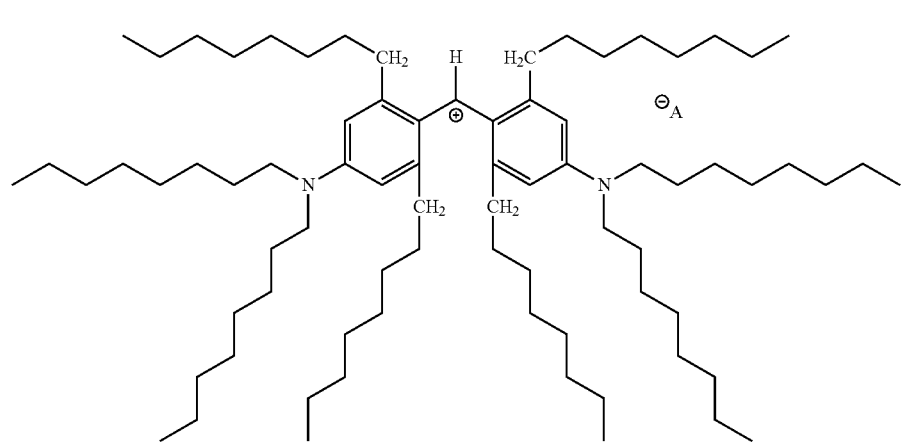
16

-continued
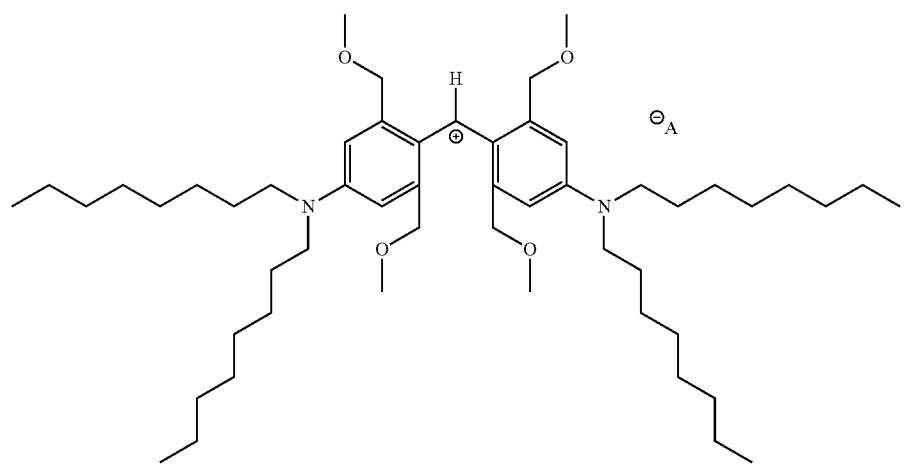
17
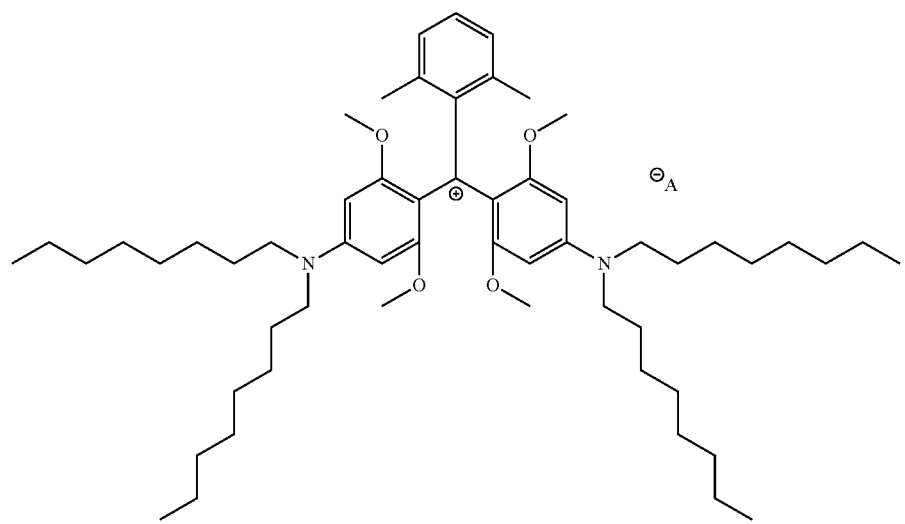
18
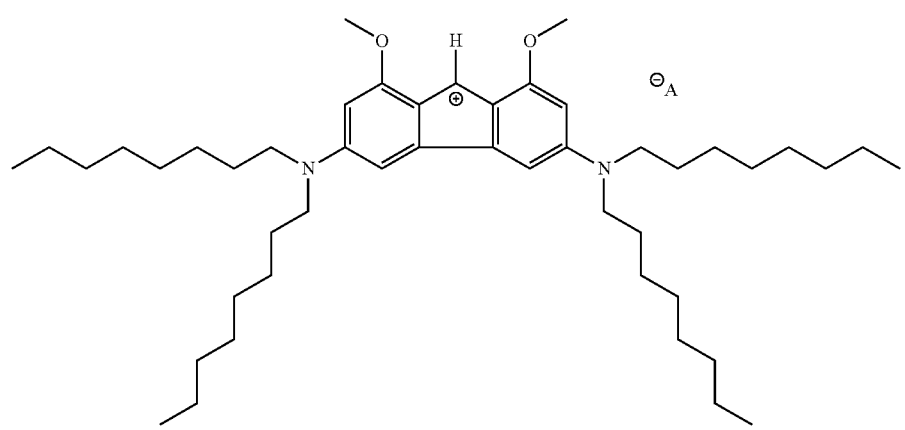
19

-continued
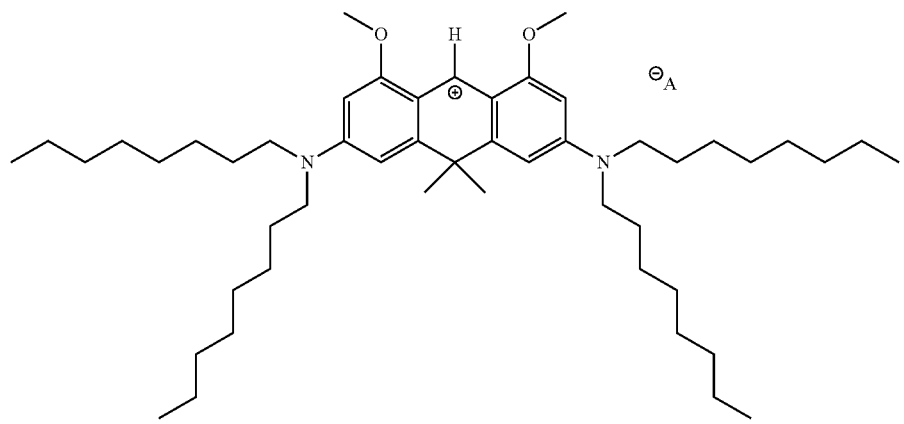
20
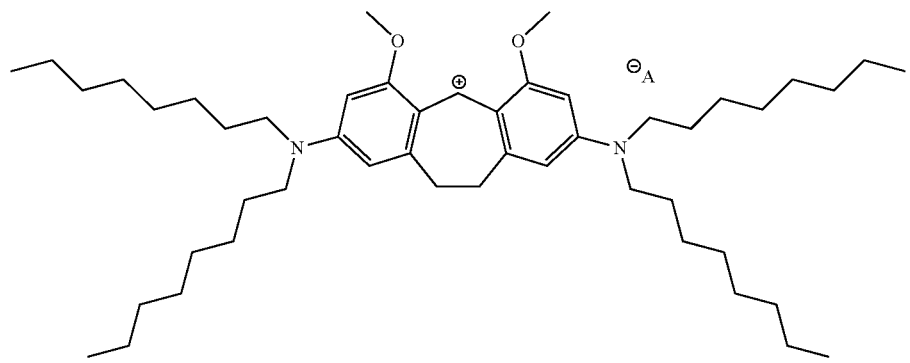
21
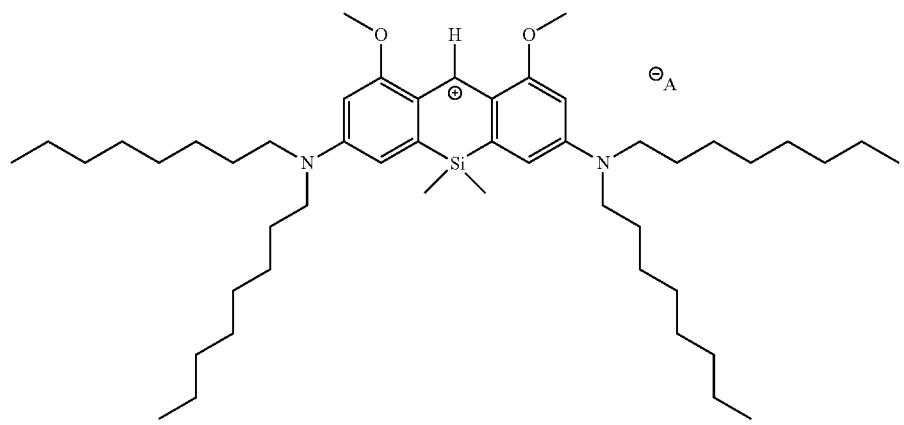
22
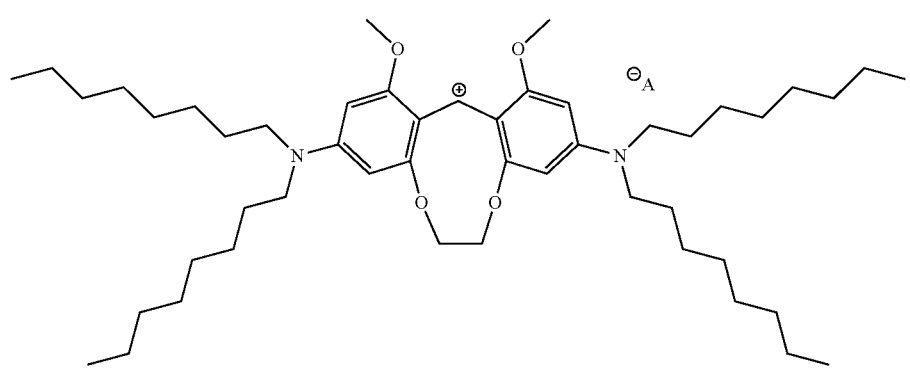
23

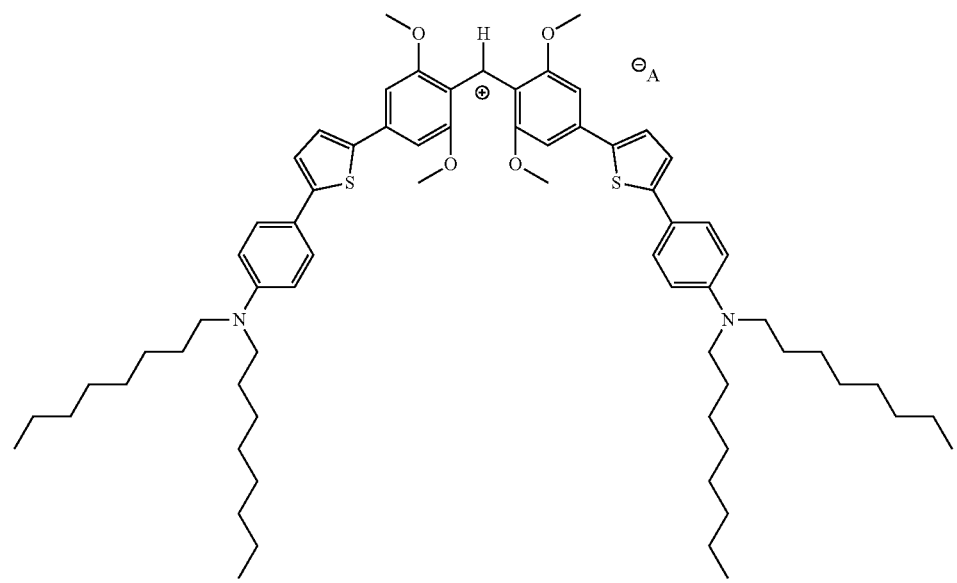
24
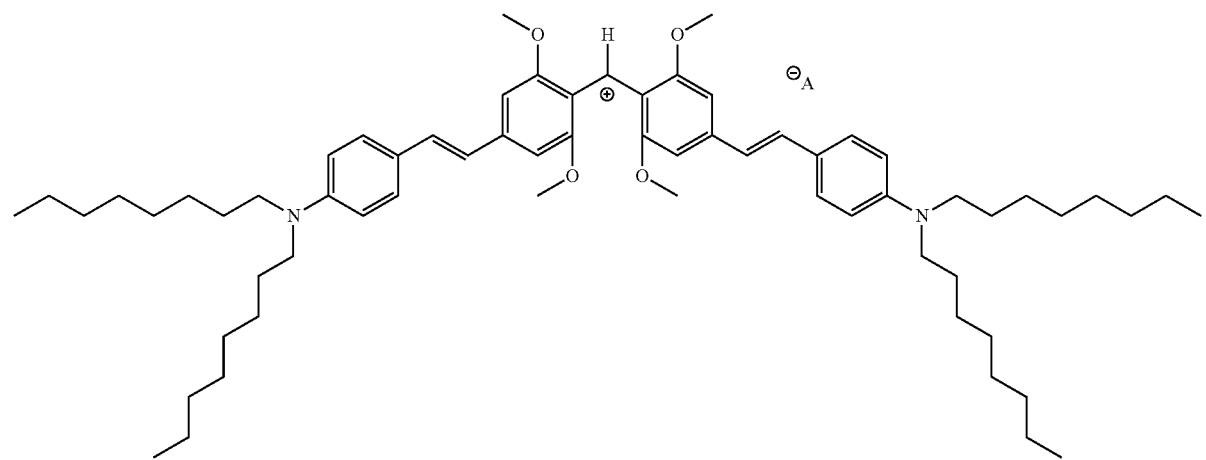
25
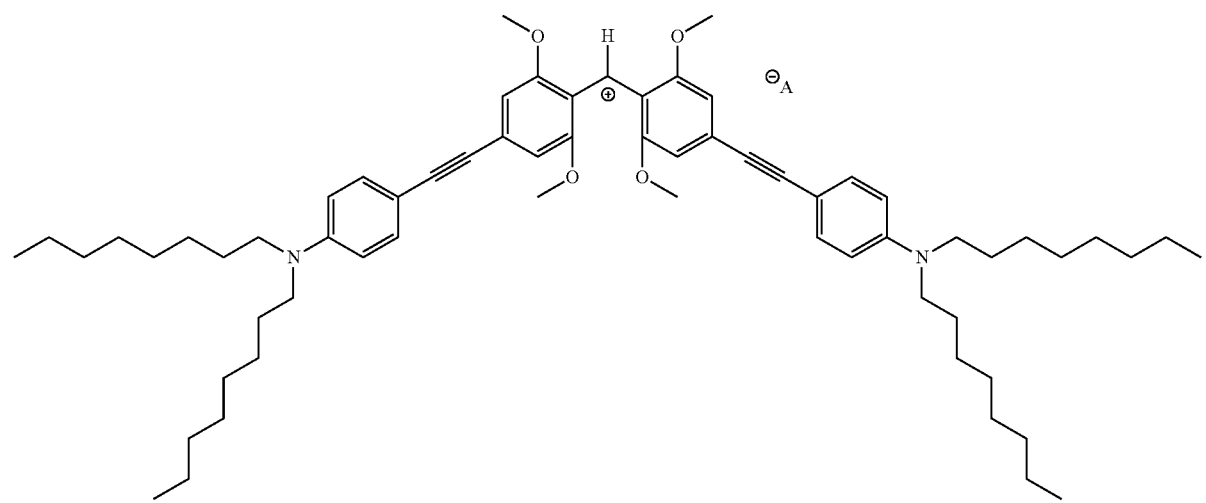
26

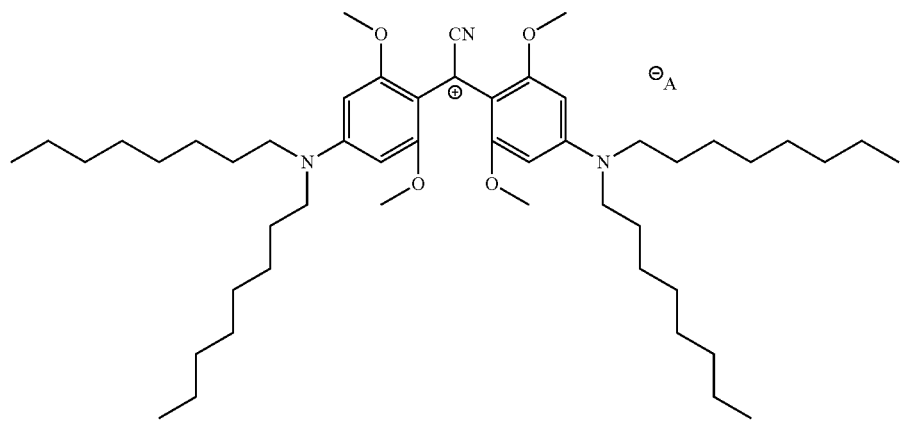
27
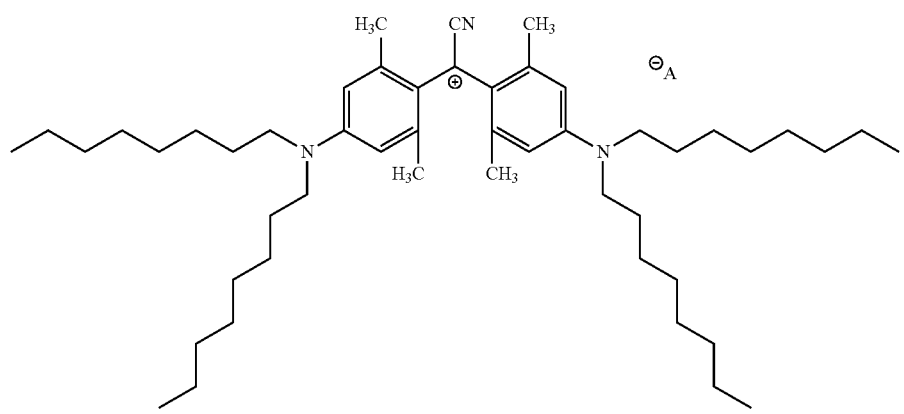
28
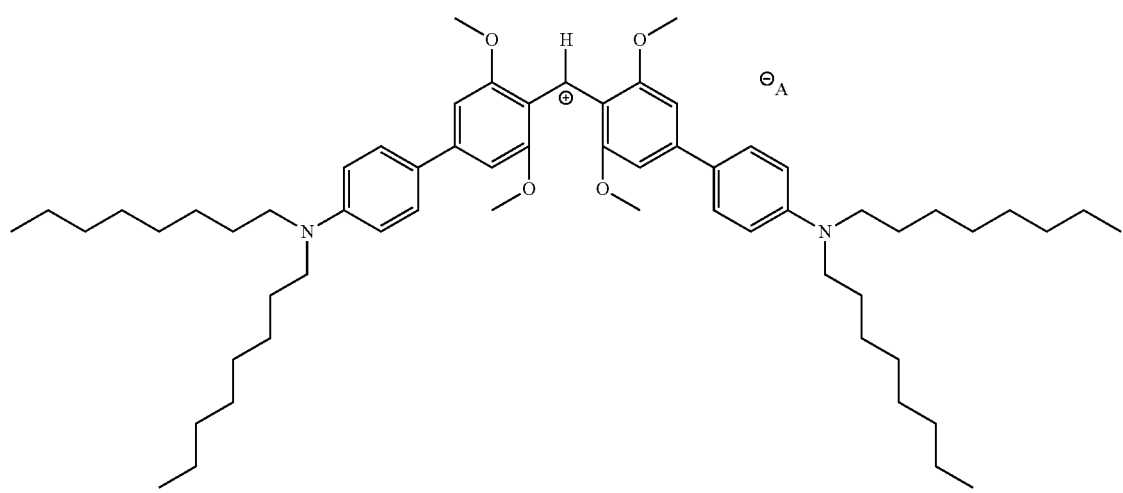
29

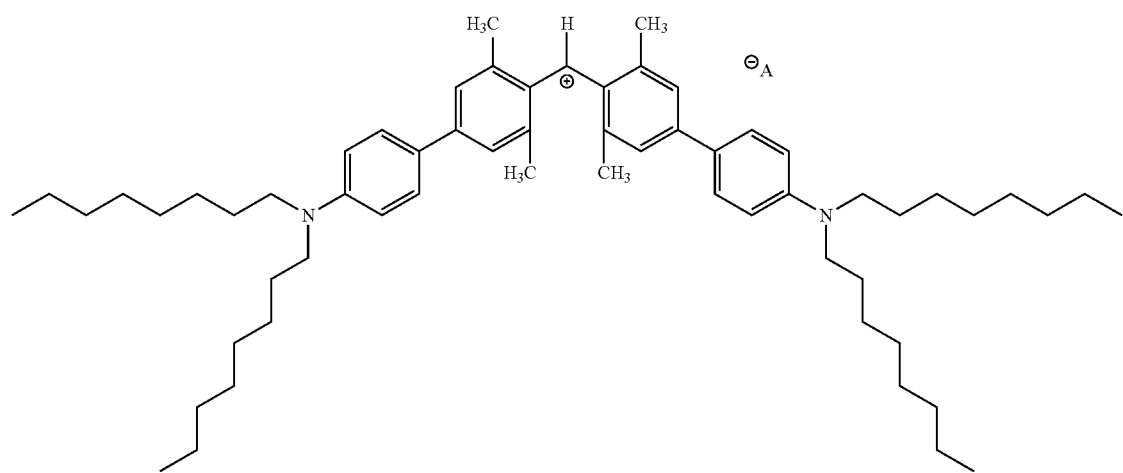
30
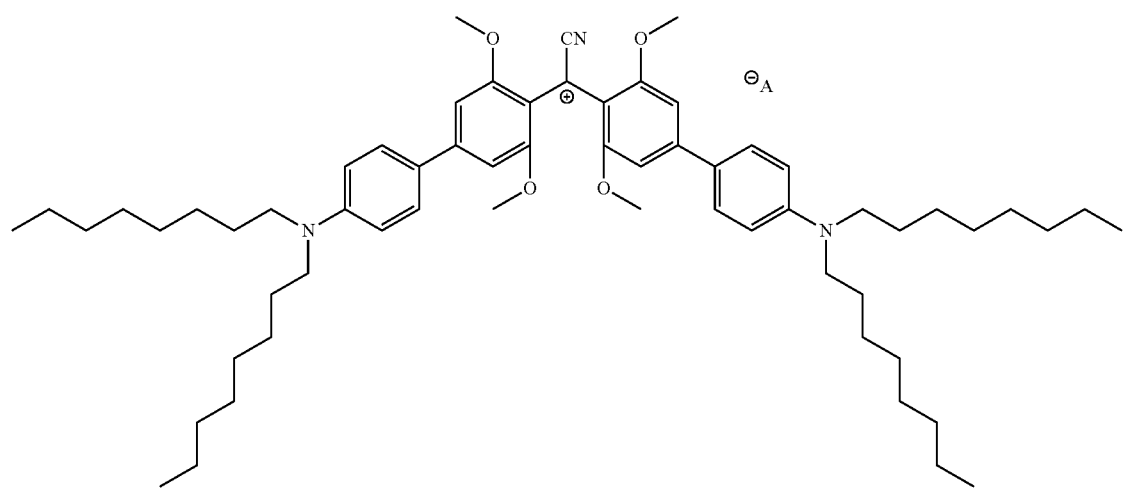
31
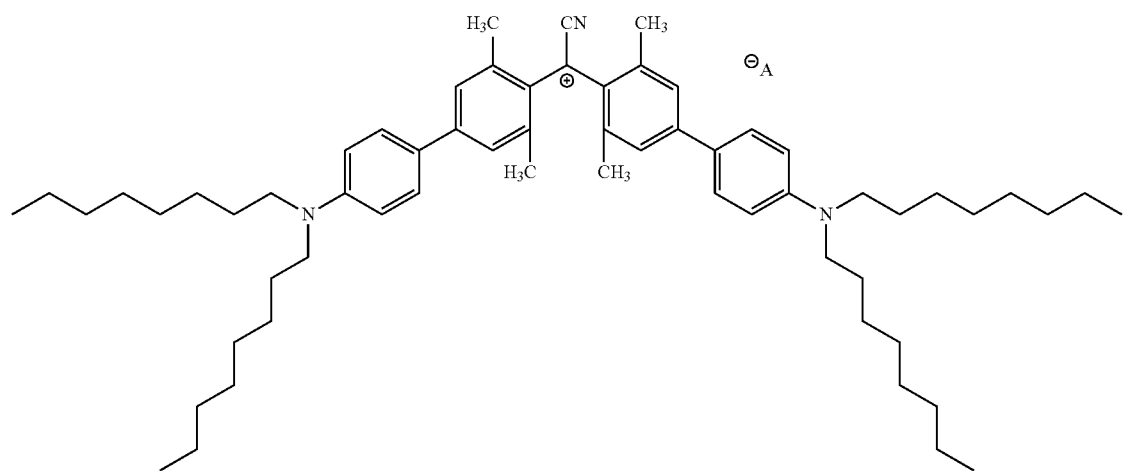
32

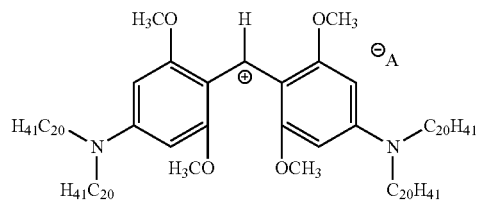
33

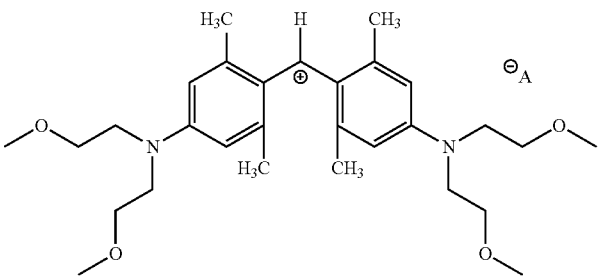
34

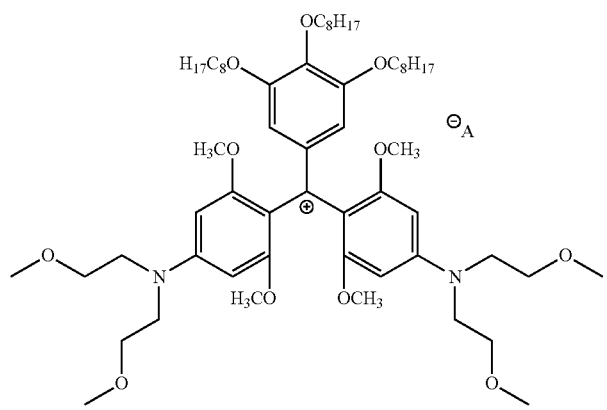
35

11. The compound according to claim 1, wherein $A^-$ represents a hexafluorophosphate, tetrafluoroborate, tetraphenylborate, 2,3-dichloro-5,6-dicyano-4-hydroxyphenolate ($DDQH^-$), halide or triflate anion.

12. A supramolecular material comprising a self-assembly of a compound of following general formula (I):

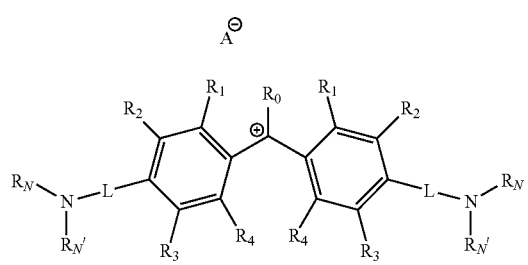

wherein:

$R_0$ represents a hydrogen atom, a halogen atom, a ($C_1$-$C_6$)alkyl, ($C_1$-$C_6$)haloalkyl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $OR_5$, $SR_6$, $NR_7R_8$, $COR_{11}$, $CO_2R_{12}$, $CONR_{13}R_{14}$, $SO_2R_{15}$, CN or $NO_2$, group, or is selected from the group consisting of:

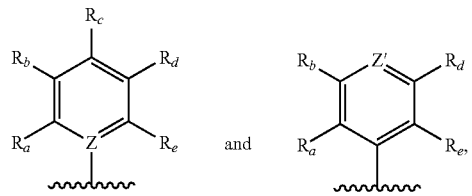

wherein:

Z represents C or $N^+ A_z^-$ and Z' represents N or $N^+$—$R_c'$ $A_z^-$, wherein $A_z^-$ represents a monovalent organic or inorganic anion, and $R_c'$ represents a hydrogen atom or a ($C_1$-$C_6$)alkyl group, $R_a$ and $R_e$ each represent, independently of each other, a hydrogen atom, a halogen atom, a ($C_1$-$C_{20}$)alkyl, ($C_1$-$C_{20}$)haloalkyl, aryl, heteroaryl, aryl-($C_1$-$C_6$)alkyl, cycloalkyl, heterocycle, heterocycle-($C_1$-$C_6$)alkyl, $OR_{22}$ or $SR_{23}$ group, and $R_b$, $R_c$ and $R_d$ each represent, independently of each other, a hydrogen atom, a halogen atom or a ($C_1$-$C_{20}$)alkyl, ($C_1$-$C_{20}$)haloalkyl, cycloalkyl, heterocycle or O($C_1$-$C_{20}$)alkyl group;

$R_1$ represents a halogen atom, a ($C_1$-$C_{20}$)alkyl, ($C_2$-$C_{12}$) alkynyl, ($C_1$-$C_{20}$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$) alkyl, $(CH_2)_m OR_{24}$, $(CH_2)_{m'} SR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;

$R_4$ represents a halogen atom, a ($C_1$-$C_{20}$)alkyl, ($C_2$-$C_{12}$) alkynyl, ($C_1$-$C_{20}$)haloalkyl, aryl, heteroaryl, aryl-($C_1$-

$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $(CH_2)_m OR_{24}$, $(CH_2)_{m'} SR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;

or both $R_4$ groups form together a bond or a chain selected from the group consisting of —C($R_{42}R_{43}$)—, —(CH$_2$)$_n$—, —Si($R_{44}R_{45}$)—, —CH$_2$—Y—CH$_2$—, and -Y—CH$_2$—CH$_2$—Y'—, wherein:

Y and Y' each represent, independently of each other, O, S or NH, n is equal to 2 or 3, $R_{42}$ and $R_{43}$, each represent, independently of each other, a ($C_1$-$C_6$)alkyl or an aryl group, and $R_{44}$ and $R_{45}$ each represent, independently of each other, a ($C_1$-$C_6$)alkyl or an aryl group;

L represents a bond, or a group selected from the group consisting of:

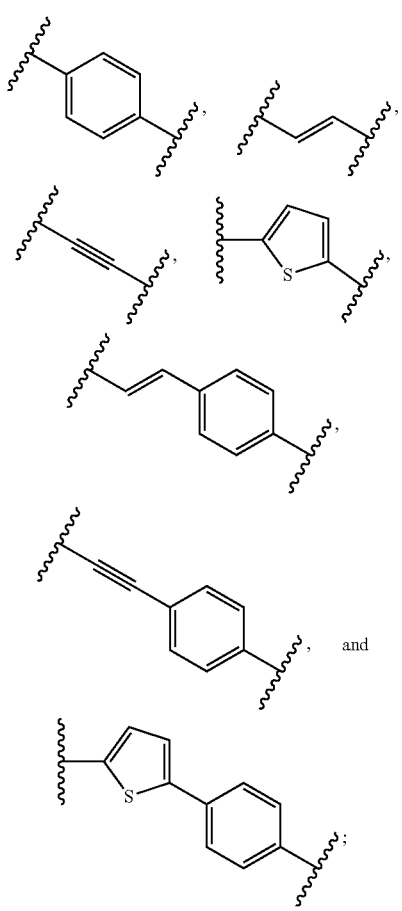

$R_2$ and $R_3$ each represent, independently of each other, a hydrogen atom, a halogen atom, a ($C_1$-$C_6$)alkyl, ($C_1$-$C_6$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle, heterocycle-($C_1$-$C_6$)alkyl, $OR_{49}$ or $NR_{51}R_{52}$ group;

or

L represents:

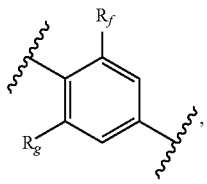

and $R_f$ and $R_2$, and $R_g$ and $R_3$ form together with the carbon atoms that carry them a cycloalkenyl or aryl group;

$R_{N}$ and $R_{N}'$ each represent, independently of each other, a ($C_7$-$C_{20}$)alkyl or ($C_7$-$C_{20}$)haloalkyl group, said group being optionally substituted by one or more groups selected from $OR_{62}$, $SR_{63}$ and $NR_{64}R_{65}$, or a group selected from the group consisting of:

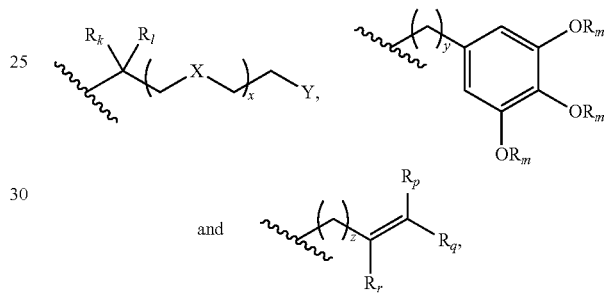

wherein:

X represents O, S or $NR_{57}$,

Y represents $OR_{58}$, $SR_{59}$ or $NR_{60}R_{61}$, x is equal to 0, 1, 2 or 3, y is equal to 0, 1, 2 or 3, z is equal to 0, 1, 2 or 3, $R_k$ and $R_l$ each represent, independently of each other, a hydrogen atom or a ($C_1$-$C_6$)alkyl group, $R_m$ represents a ($C_1$-$C_{20}$)alkyl group, $R_r$ represents a hydrogen atom or a ($C_1$-$C_6$)alkyl group, $R_p$ and $R_q$ each represent, independently of each other, a hydrogen atom, a ($C_1$-$C_6$)alkyl, an aryl or heteroaryl group, $R_{57}$ to $R_{65}$ each represent, independently of each other, a hydrogen atom or a ($C_1$-$C_6$)alkyl group;

$R_5$ to $R_8$, $R_{11}$ to $R_{15}$, $R_{24}$, $R_{25}$, $R_{28}$, $R_{29}$, $R_{32}$, $R_{36}$, $R_{38}$, $R_{39}$, $R_{49}$, $R_{51}$ and $R_{52}$ each represent, independently of each other, a hydrogen atom, a ($C_1$-$C_6$)alkyl, ($C_1$-$C_6$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle or heterocycle-($C_1$-$C_6$)alkyl group, said group being optionally substituted by one or more groups selected from a halogen atom, a ($C_1$-$C_6$)alkyl, ($C_1$-$C_6$)haloalkyl, $OR_{64}$, $SR_{65}$ and $NR_{66}R_{67}$ group, wherein $R_{64}$ to $R_{67}$ each represent, independently of each other, a hydrogen atom or a ($C_1$-$C_6$)alkyl group;

$R_{22}$, $R_{23}$, $R_{26}$ and $R_{27}$ each represent, independently of each other a hydrogen atom, a ($C_1$-$C_{20}$)alkyl, ($C_1$-$C_{20}$)haloalkyl, aryl, heteroaryl, aryl-($C_1$-$C_6$)alkyl, heteroaryl-($C_1$-$C_6$)alkyl, cycloalkyl, cycloalkyl-($C_1$-$C_6$)alkyl, heterocycle or heterocycle-($C_1$-$C_6$)alkyl group, said group being optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group, wherein $R_{66}$ to $R_{69}$ each represent, independently of each other, a hydrogen atom or a $(C_1-C_6)$alkyl group; and $A^-$ represents a monovalent, organic or inorganic anion, with the proviso that when $R_1$ and $R_4$ are the same, and $R_0$ is:

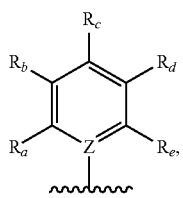

wherein Z represents C,
at least one of $R_a$ and $R_e$ is not the same as $R_1$.

13. A reflective or photonic or nanophotonic or optoelectronic device, comprising at least one compound of following general formula (I):

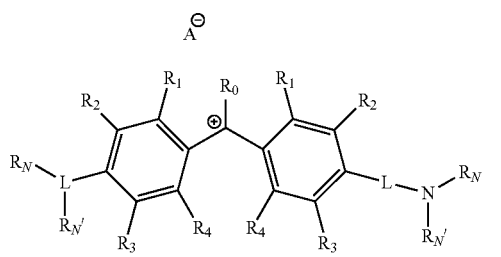

(I)

wherein:

$R_0$ represents a hydrogen atom, a halogen atom, a $(C_1-C_6)$alkyl, $(C_1-C_6)$haloalkyl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $OR_5$, $SR_6$, $NR_7R_8$, $COR_{11}$, $CO_2R_{12}$, $CONR_{13}R_{14}$, $SO_2R_{15}$, CN or $NO_2$, group, or is selected from the group consisting of:

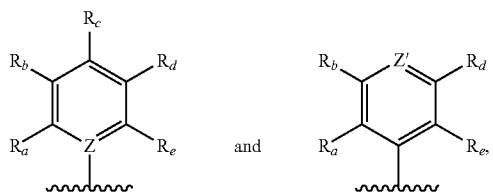

and wherein:

Z represents C or $N^+ A_z^-$ and $Z'$ represents N or $N^+-R_c' A_z^-$, wherein $A_z^-$ represents a monovalent organic or inorganic anion, and $R_c'$ represents a hydrogen atom or a $(C_1-C_6)$alkyl group, $R_a$ and $R_e$ each represent, independently of each other, a hydrogen atom, a halogen atom, a $(C_1-C_{20})$alkyl, $(C_1-C_{20})$haloalkyl, aryl, heteroaryl, aryl-$(C_1-C_6)$alkyl, cycloalkyl, heterocycle, heterocycle-$(C_1-C_6)$alkyl, $OR_{22}$ or $SR_{23}$ group, and $R_b$, $R_c$ and $R_d$ each represent, independently of each other, a hydrogen atom, a halogen atom or a $(C_1-C_{20})$alkyl, $(C_1-C_{20})$haloalkyl, cycloalkyl, heterocycle or $O(C_1-C_{20})$alkyl group;

$R_1$ represents a halogen atom, a $(C_1-C_{20})$alkyl, $(C_2-C_{12})$alkynyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_m OR_{24}$, $(CH_2)_{m'}SR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;

$R_4$ represents a halogen atom, a $(C_1-C_{20})$alkyl, $(C_2-C_{12})$alkynyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle, heterocycle-$(C_1-C_6)$alkyl, $(CH_2)_m OR_{24}$, $(CH_2)_{m'}SR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;

or both $R_4$ groups form together a bond or a chain selected from the group consisting of $-C(R_{42}R_{43})-$, $-(CH_2)_n-$, $-Si(R_{44}R_{45})-$, $-CH_2-Y-CH_2-$, and $-Y-CH_2-CH_2-Y'-$, wherein:

Y and Y' each represent, independently of each other, O, S or NH, n is equal to 2 or 3, $R_{42}$ and $R_{43}$, each represent, independently of each other, a $(C_1-C_6)$alkyl or an aryl group, and $R_{44}$ and $R_{45}$ each represent, independently of each other, a $(C_1-C_6)$alkyl or an aryl group;

L represents a bond, or a group selected from the group consisting of:

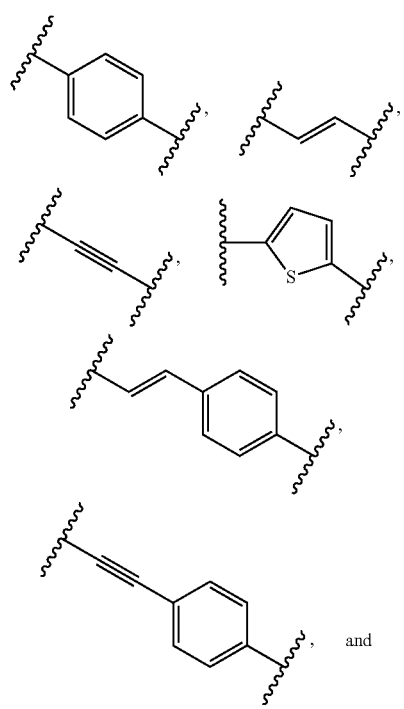

and

-continued

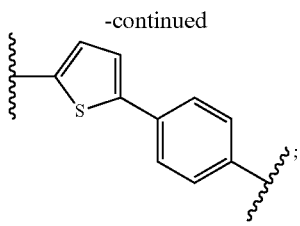

R$_2$ and R$_3$ each represent, independently of each other, a hydrogen atom, a halogen atom, a (C$_1$-C$_6$)alkyl, (C$_1$-C$_6$)haloalkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle, heterocycle-(C$_1$-C$_6$)alkyl, OR$_{49}$ or NR$_{51}$R$_{52}$ group;

or

L represents:

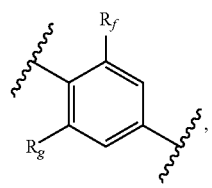

and

R$_f$ and R$_2$, and R$_g$ and R$_3$ form together with the carbon atoms that carry them a cycloalkenyl or aryl group;

R$_N$ and R$_N$' each represent, independently of each other, a (C$_7$-C$_{20}$)alkyl or (C$_7$-C$_{20}$)haloalkyl group, said group being optionally substituted by one or more groups selected from OR$_{62}$, SR$_{63}$ and NR$_{64}$R$_{65}$, or a group selected from the group consisting of:

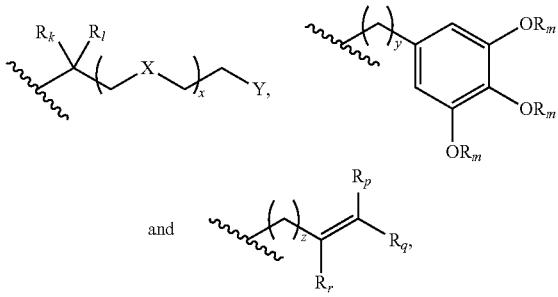

wherein:

X represents O, S or NR$_{57}$,

Y represents OR$_{58}$, SR$_{59}$ or NR$_{60}$ R$_{61}$, x is equal to 0, 1, 2 or 3, y is equal to 0, 1, 2 or 3, z is equal to 0, 1, 2 or 3, R$_k$ and R$_l$ each represent, independently of each other, a hydrogen atom or a (C$_1$-C$_6$)alkyl group, R$_m$ represents a (C$_1$-C$_{20}$)alkyl group, R$_r$ represents a hydrogen atom or a (C$_1$-C$_6$)alkyl group, R$_p$ and R$_q$ each represent, independently of each other, a hydrogen atom, a (C$_1$-C$_6$)alkyl, an aryl or heteroaryl group, R$_{57}$ to R$_{65}$ each represent, independently of each other, a hydrogen atom or a (C$_1$-C$_6$)alkyl group;

R$_5$ to R$_8$, R$_{11}$ to R$_{15}$, R$_{24}$, R$_{25}$, R$_{28}$, R$_{29}$, R$_{32}$, R$_{36}$, R$_{38}$, R$_{39}$, R$_{49}$, R$_{51}$ and R$_{52}$ each represent, independently of each other, a hydrogen atom, a (C$_1$-C$_6$)alkyl, (C$_1$-C$_6$)haloalkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle or heterocycle-(C$_1$-C$_6$)alkyl group, said group being optionally substituted by one or more groups selected from a halogen atom, a (C$_1$-C$_6$)alkyl, (C$_1$-C$_6$)haloalkyl, OR$_{64}$, SR$_{65}$ and NR$_{66}$R$_{67}$ group, wherein R64 to R67 each represent, independently of each other, a hydrogen atom or a (C$_1$-C$_6$)alkyl group;

R$_{22}$, R$_{23}$, R$_{26}$ and R$_{27}$ each represent, independently of each other a hydrogen atom, a (C$_1$-C$_{20}$)alkyl, (C$_1$-C$_{20}$)haloalkyl, aryl, heteroaryl, aryl-(C$_1$-C$_6$)alkyl, heteroaryl-(C$_1$-C$_6$)alkyl, cycloalkyl, cycloalkyl-(C$_1$-C$_6$)alkyl, heterocycle or heterocycle-(C$_1$-C$_6$)alkyl group, said group being optionally substituted by one or more groups selected from a halogen atom, a (C$_1$-C$_6$)alkyl, (C$_1$-C$_6$)haloalkyl, OR$_{66}$, SR$_{67}$ and NR$_{68}$R$_{69}$ group, wherein R$_{66}$ to R$_{69}$ each represent, independently of each other, a hydrogen atom or a (C$_1$-C$_6$)alkyl group; and A$^-$ represents a monovalent, organic or inorganic anion, with the proviso that when R$_1$ and R$_4$ are the same, and R$_0$ is:

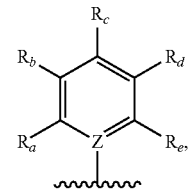

wherein Z represents C, at least one of R$_a$ and R$_e$ is not the same as R$_1$.

14. The supramolecular material according to claim 12, wherein the supramolecular material is an organic-based metal-like liquid film (OMELLF).

15. The supramolecular material according to claim 12, wherein the supramolecular material is a metal-like reflective coating or a metal-like particle.

16. The compound according to claim 1, wherein R$_{22}$, R$_{23}$, R$_{26}$ and R$_{27}$ each represent, independently of each other a hydrogen atom or a (C$_1$-C$_{20}$)alkyl, (C$_1$-C$_{12}$)alkyl or a (C$_1$-C$_6$)alkyl group.

17. The compound according to claim 1, wherein R$_5$ to R$_8$, R$_{11}$ to R$_{15}$, R$_{24}$, R$_{25}$, R$_{28}$, R$_{29}$, R$_{32}$, R$_{36}$, R$_{38}$, R$_{39}$, R$_{49}$; R$_{51}$ and R$_{52}$ each represent, independently of each other, a hydrogen atom or a (C$_1$-C$_6$)alkyl group.

18. The compound according to claim 1, wherein R$_0$ represents a hydrogen atom, a (C$_1$-C$_6$)alkyl or a CN group, notably a hydrogen atom or a CN group.

19. The compound according to claim 1, wherein R$_2$ and R$_3$ both represent a hydrogen atom.

20. The supramolecular material according to claim 12, wherein the supramolecular material is a pigment.

21. A chromophore comprising a compound of following general formula (I):

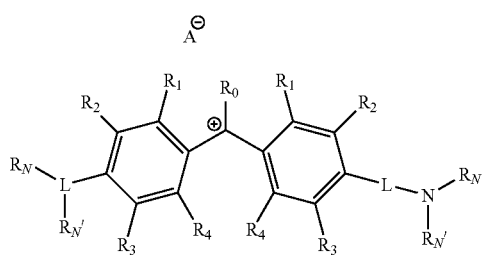

(I)

wherein:
$R_0$ represents a hydrogen atom, a halogen atom, a $(C_1$-$C_6)$alkyl, $(C_1$-$C_6)$haloalkyl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $OR_5$, $SR_6$, $NR_7R_8$, $COR_{11}$, $CO_2R_{12}$, $CONR_{13}R_{14}$, $SO_2R_{15}$, CN or $NO_2$, group, or is selected from the group consisting of:

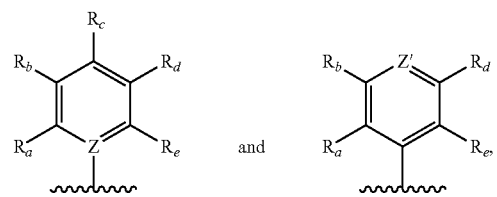

and wherein:
Z represents C or $N^+A_z^-$ and Z' represents N or $N^+$—$R_c$' $A_z^-$, wherein
$A_z^-$ represents a monovalent organic or inorganic anion, and
$R_c$' represents a hydrogen atom or a $(C_1$-$C_6)$alkyl group,
$R_a$ and $R_e$ each represent, independently of each other, a hydrogen atom, a halogen atom, a $(C_1$-$C_{20})$alkyl, $(C_1$-$C_{20})$haloalkyl, aryl, heteroaryl, aryl-$(C_1$-$C_6)$alkyl, cycloalkyl, heterocycle, heterocycle-$(C_1$-$C_6)$alkyl, $OR_{22}$ or $SR_{23}$ group, and
$R_b$, $R_c$ and $R_d$ each represent, independently of each other, a hydrogen atom, a halogen atom or a $(C_1$-$C_{20})$alkyl, $(C_1$-$C_{20})$haloalkyl, cycloalkyl, heterocycle or $O(C_1$-$C_{20})$alkyl group;
$R_1$ represents a halogen atom, a $(C_1$-$C_{20})$alkyl, $(C_2$-$C_{12})$ alkynyl, $(C_1$-$C_{20})$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$ alkyl, $(CH_2)_mOR_{24}$, $(CH_2)_m$'$SR_{25}$, $OR_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;
$R_4$ represents a halogen atom, a $(C_1$-$C_{20})$alkyl, $(C_2$-$C_{12})$ alkynyl, $(C_1$-$C_{20})$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$ alkyl, $(CH_2)_mOR_{24}$, $(CH_2)_m$'$SR_{25,0}R_{26}$, $SR_{27}$, $NR_{28}R_{29}$, $COR_{32}$, $OCOR_{36}$ or $NR_{38}COR_{39}$ group, wherein m and m' are, independently of each other, equal to 1, 2 or 3;
or
both $R_4$ groups form together a bond or a chain selected from the group consisting of —$C(R_{42}R_{43})$—, —$(CH_2)_n$—, —$Si(R_{44}R_{45})$— and —Y—$CH_2$—$CH_2$—Y'—, wherein:

Y and Y' each represent, independently of each other, O, S or NH,
n is equal to 2 or 3,
$R_{42}$ and $R_{43}$, each represent, independently of each other, a $(C_1$-$C_6)$alkyl or an aryl group, and
$R_{44}$ and $R_{45}$ each represent, independently of each other, a $(C_1$-$C_6)$alkyl or an aryl group;
L represents a bond, or a group selected from the group consisting of:

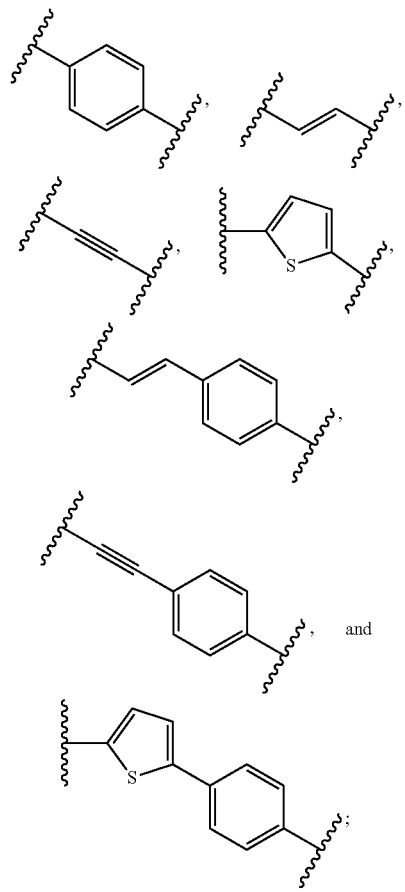

$R_2$ and $R_3$ each represent, independently of each other, a hydrogen atom, a halogen atom, a $(C_1$-$C_6)$ alkyl, $(C_1$-$C_6)$haloalkyl, aryl, heteroaryl, aryl-$(C_1$-$C_6)$alkyl, heteroaryl-$(C_1$-$C_6)$alkyl, cycloalkyl, cycloalkyl-$(C_1$-$C_6)$alkyl, heterocycle, heterocycle-$(C_1$-$C_6)$alkyl, $OR_{49}$ or $NR_{51}R_{52}$ group;
or
L represents:

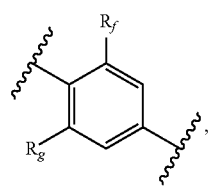

and $R_f$ and $R_2$, and $R_g$ and $R_3$ form together with the carbon atoms that carry them a cycloalkenyl or aryl group;

$R_N$ and $R_{N'}$ each represent, independently of each other, a $(C_7-C_{20})$alkyl or $(C_7-C_{20})$haloalkyl group, said group being optionally substituted by one or more groups selected from $OR_{62}$, $SR_{63}$ and $NR_{64}R_{65}$, or a group selected from the group consisting of:

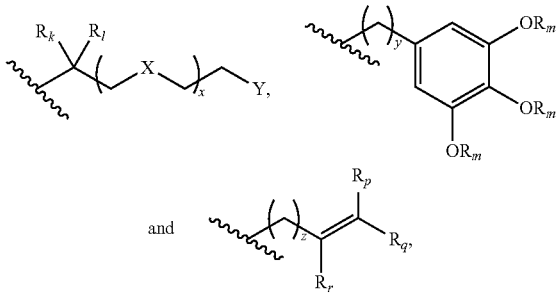

and wherein:
X represents O, S or $NR_{57}$,
Y represents $OR_{58}$, $SR_{59}$ or $NR_{60}R_{61}$,
x is equal to 0, 1, 2 or 3,
y is equal to 0, 1, 2 or 3,
z is equal to 0, 1, 2 or 3,
$R_k$ and $R_l$ each represent, independently of each other, a hydrogen atom or a $(C_1-C_6)$alkyl group,
$R_m$ represents a $(C_1-C_{20})$alkyl group,
$R_r$ represents a hydrogen atom or a $(C_1-C_6)$alkyl group,
$R_p$ and $R_q$ each represent, independently of each other, a hydrogen atom, a $(C_1-C_6)$alkyl, an aryl or heteroaryl group,
$R_{57}$ to $R_{65}$ each represent, independently of each other, a hydrogen atom or a $(C_1-C_6)$alkyl group;
$R_5$ to $R_8$, $R_{11}$ to $R_{15}$, $R_{24}$, $R_{25}$, $R_{28}$, $R_{29}$, $R_{32}$, $R_{36}$, $R_{38}$, $R_{39}$, $R_{49}$, $R_{51}$ and $R_{52}$ each represent, independently of each other, a hydrogen atom, a $(C_1-C_6)$alkyl, $(C_1-C_6)$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{64}$, $SR_{65}$ and $NR_{66}R_{67}$ group, wherein $R_{64}$ to $R_{67}$ each represent, independently of each other, a hydrogen atom or a $(C_1-C_6)$alkyl group;
$R_{22}$, $R_{23}$, $R_{26}$ and $R_{27}$ each represent, independently of each other a hydrogen atom, a $(C_1-C_{20})$alkyl, $(C_1-C_{20})$haloalkyl, aryl, heteroaryl, aryl-$(C_1-C_6)$alkyl, heteroaryl-$(C_1-C_6)$alkyl, cycloalkyl, cycloalkyl-$(C_1-C_6)$alkyl, heterocycle or heterocycle-$(C_1-C_6)$alkyl group, said group being optionally substituted by one or more groups selected from a halogen atom, a $(C_1-C_6)$alkyl, $(C_1-C_6)$haloalkyl, $OR_{66}$, $SR_{67}$ and $NR_{68}R_{69}$ group, wherein $R_{66}$ to $R_{69}$ each represent, independently of each other, a hydrogen atom or a $(C_1-C_6)$alkyl group; and
$A^-$ represents a monovalent, organic or inorganic anion, with the proviso that when $R_1$ and $R_4$ are the same, and $R_0$ is:

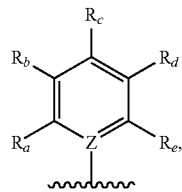

wherein Z represents C,
at least one of $R_a$ and $R_e$ is not the same as $R_1$.

22. The chromophore according to claim 21, wherein the chromophore is a dye.

* * * * *